(12) United States Patent
Mack et al.

(10) Patent No.: US 10,866,246 B2
(45) Date of Patent: *Dec. 15, 2020

(54) DEVICES, METHODS AND KITS FOR SAMPLE CHARACTERIZATION

(71) Applicant: Intabio, Inc., Newark, CA (US)

(72) Inventors: Scott Mack, Boulder Creek, CA (US); Erik Gentalen, Fremont, CA (US)

(73) Assignee: INTABIO, INC., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/781,436

(22) Filed: Feb. 4, 2020

(65) Prior Publication Data
US 2020/0191796 A1 Jun. 18, 2020

Related U.S. Application Data

(63) Continuation of application No. 16/261,382, filed on Jan. 29, 2019, now Pat. No. 10,591,488.
(Continued)

(51) Int. Cl.
*G01N 33/68* (2006.01)
*G01N 1/40* (2006.01)
(Continued)

(52) U.S. Cl.
CPC ...... *G01N 33/6851* (2013.01); *B01L 3/50273* (2013.01); *B01L 3/502715* (2013.01);
(Continued)

(58) Field of Classification Search
CPC ...... G01N 33/6851; G01N 30/00; G01N 1/40; G01N 2001/4038; H01J 49/165;
(Continued)

(56) References Cited

U.S. PATENT DOCUMENTS

| 5,110,434 A | 5/1992 | Zhu et al. |
| 5,183,489 A | 2/1993 | Brehm et al. |

(Continued)

FOREIGN PATENT DOCUMENTS

| AT | 548347 T | 3/2012 |
| DE | 05705627 T1 | 5/2007 |

(Continued)

OTHER PUBLICATIONS

Nordman et al. (N Nordman, S Lauren, T Kotiaho, S Franssila, R Kostiainen, T Sikanen, Interfacing microchip isoelectric focusing with on-chip electrospray ionization mass spectrometry, J. Chromatography A 1398 (2015) 121-126) (Year: 2015).*

(Continued)

*Primary Examiner* — Maris R Kessel
*Assistant Examiner* — Joshua L Allen
(74) *Attorney, Agent, or Firm* — Wilson Sonsini Goodrich & Rosati

(57) ABSTRACT

Devices and methods for characterization of samples are provided. Samples may comprise one or more analytes. Some methods described herein include performing enrichment steps on a device. Some methods described herein include performing mobilization of analytes. Analytes may then be further processed and characterized.

29 Claims, 17 Drawing Sheets

US 10,866,246 B2
Page 2

Related U.S. Application Data

(60) Provisional application No. 62/623,492, filed on Jan. 29, 2018.

(51) Int. Cl.
| | | |
|---|---|---|
| *B01L 3/00* | (2006.01) | |
| *H01J 49/16* | (2006.01) | |
| *H01J 49/04* | (2006.01) | |
| *G01N 30/00* | (2006.01) | |

(52) U.S. Cl.
CPC .............. *G01N 1/40* (2013.01); *G01N 30/00* (2013.01); *G01N 33/6848* (2013.01); *H01J 49/0404* (2013.01); *H01J 49/165* (2013.01); B01L 2300/0645 (2013.01); B01L 2300/0654 (2013.01); B01L 2300/0816 (2013.01); B01L 2300/0887 (2013.01); B01L 2400/0406 (2013.01); B01L 2400/0421 (2013.01); G01N 2001/4038 (2013.01)

(58) Field of Classification Search
CPC ............ H01J 49/0404; B01L 3/502715; B01L 3/50273; B01L 2300/0887; B01L 2300/0816; B01L 2300/0654; B01L 2300/0645; B01L 2400/0406; B01L 2400/0421

See application file for complete search history.

(56) References Cited

U.S. PATENT DOCUMENTS

| | | | |
|---|---|---|---|
| 5,259,939 A | 11/1993 | Chen | |
| 5,395,502 A | 3/1995 | Pawliszyn | |
| 5,423,964 A | 6/1995 | Smith et al. | |
| 5,468,359 A | 11/1995 | Pawliszyn | |
| 5,779,868 A | 7/1998 | Parce et al. | |
| 5,784,154 A | 7/1998 | Pawliszyn | |
| 5,800,690 A | 9/1998 | Chow et al. | |
| 5,842,787 A | 12/1998 | Kopf-Sill et al. | |
| 5,858,195 A * | 1/1999 | Ramsey | B01F 13/0076 204/601 |
| 5,876,675 A | 3/1999 | Kennedy | |
| 5,880,071 A | 3/1999 | Parce et al. | |
| 5,957,579 A | 9/1999 | Kopf-Sill et al. | |
| 5,958,203 A | 9/1999 | Parce et al. | |
| 5,965,001 A | 10/1999 | Chow et al. | |
| 5,972,187 A | 10/1999 | Parce et al. | |
| 5,985,121 A | 11/1999 | Wu et al. | |
| 6,001,229 A | 12/1999 | Ramsey | |
| 6,010,607 A | 1/2000 | Ramsey | |
| 6,010,608 A | 1/2000 | Ramsey | |
| 6,033,546 A | 3/2000 | Ramsey | |
| 6,042,709 A | 3/2000 | Parce et al. | |
| 6,048,498 A | 4/2000 | Kennedy | |
| 6,080,295 A | 6/2000 | Parce et al. | |
| 6,110,343 A * | 8/2000 | Ramsey | B01L 3/50273 204/450 |
| 6,149,787 A | 11/2000 | Chow et al. | |
| 6,167,910 B1 | 1/2001 | Chow | |
| 6,186,660 B1 | 2/2001 | Kopf-Sill et al. | |
| 6,231,737 B1 | 5/2001 | Ramsey et al. | |
| 6,287,520 B1 | 9/2001 | Parce et al. | |
| 6,321,791 B1 | 11/2001 | Chow | |
| 6,413,401 B1 | 7/2002 | Chow et al. | |
| 6,430,512 B1 | 8/2002 | Gallagher | |
| 6,482,364 B2 | 11/2002 | Parce et al. | |
| 6,494,230 B2 | 12/2002 | Chow et al. | |
| 6,517,234 B1 | 2/2003 | Kopf-Sill et al. | |
| 6,547,942 B1 | 4/2003 | Parce et al. | |
| 6,611,768 B2 | 8/2003 | Gallagher | |
| 6,632,655 B1 | 10/2003 | Mehta et al. | |
| 6,744,046 B2 | 6/2004 | Valaskovic et al. | |
| 6,803,568 B2 | 10/2004 | Bousse et al. | |
| 6,831,274 B2 | 12/2004 | Smith et al. | |
| 6,974,526 B2 | 12/2005 | Lee et al. | |
| 6,974,527 B2 | 12/2005 | Liu et al. | |
| 6,977,372 B2 | 12/2005 | Valaskovic et al. | |
| 7,001,496 B2 | 2/2006 | Parce et al. | |
| 7,022,214 B2 | 4/2006 | Olech | |
| 7,166,202 B2 | 1/2007 | Bukshpan et al. | |
| 7,243,670 B2 | 7/2007 | Witt et al. | |
| 7,285,411 B1 | 10/2007 | Parce et al. | |
| 7,329,865 B2 | 2/2008 | Kuypers | |
| 7,339,166 B2 | 3/2008 | Tang et al. | |
| 7,381,317 B2 | 6/2008 | Liu et al. | |
| 7,391,020 B2 | 6/2008 | Bousse et al. | |
| 7,425,700 B2 | 9/2008 | Stults et al. | |
| 7,426,442 B2 | 9/2008 | Gallagher | |
| 7,495,210 B2 | 2/2009 | Li | |
| 7,601,251 B2 | 10/2009 | Rooney et al. | |
| 7,642,508 B2 | 1/2010 | Li | |
| 7,655,477 B1 | 2/2010 | Schneider et al. | |
| 7,825,375 B2 | 11/2010 | Sano | |
| 7,871,575 B2 | 1/2011 | Baeuerle et al. | |
| 8,076,152 B2 | 12/2011 | Robotti | |
| 8,097,472 B2 | 1/2012 | Schneider et al. | |
| 8,260,561 B2 | 9/2012 | Gallagher | |
| 8,267,914 B1 | 9/2012 | Chang et al. | |
| 8,613,845 B2 | 12/2013 | Maxwell et al. | |
| 8,728,290 B1 * | 5/2014 | Sommer | G01N 27/44747 204/455 |
| 8,859,296 B2 | 10/2014 | Schneider et al. | |
| 8,940,232 B2 | 1/2015 | Roach et al. | |
| 9,006,648 B2 | 4/2015 | Ramsey et al. | |
| 9,108,195 B2 | 8/2015 | Herr et al. | |
| 9,159,537 B2 | 10/2015 | McGivney et al. | |
| 9,255,905 B1 | 2/2016 | Mellors et al. | |
| 9,347,440 B2 | 5/2016 | Lebl et al. | |
| 9,362,102 B2 | 6/2016 | Dovichi et al. | |
| 9,377,440 B2 | 6/2016 | Wu et al. | |
| 9,465,014 B2 | 10/2016 | Dovichi et al. | |
| 9,502,225 B2 | 11/2016 | Mellors et al. | |
| 9,606,082 B2 | 3/2017 | Mellors et al. | |
| 9,728,387 B2 | 8/2017 | Mellors et al. | |
| 9,778,223 B2 | 10/2017 | Schneider et al. | |
| 10,107,782 B2 | 10/2018 | Huang et al. | |
| 10,209,217 B2 | 2/2019 | Gentalen et al. | |
| 10,209,218 B2 | 2/2019 | Mellors | |
| 10,401,324 B2 | 9/2019 | Gentalen | |
| 10,407,655 B2 | 9/2019 | Hinojosa et al. | |
| 10,514,360 B1 | 12/2019 | Gentalen et al. | |
| 10,591,488 B2 * | 3/2020 | Gentalen | G01N 30/00 |
| 2002/0079220 A1 | 6/2002 | Pawliszyn | |
| 2002/0139751 A1 | 10/2002 | Zhang et al. | |
| 2003/0000835 A1 * | 1/2003 | Witt | G01N 27/44717 137/14 |
| 2003/0089605 A1 | 5/2003 | Timperman | |
| 2004/0091943 A1 | 5/2004 | Schneider | |
| 2004/0112751 A1 | 6/2004 | Han et al. | |
| 2004/0113068 A1 * | 6/2004 | Bousse | B01L 3/502715 250/288 |
| 2004/0202994 A1 | 10/2004 | Timperman | |
| 2005/0021799 A1 | 1/2005 | Imamura et al. | |
| 2005/0047969 A1 | 3/2005 | Zhao et al. | |
| 2005/0072915 A1 | 4/2005 | Stults et al. | |
| 2005/0155861 A1 | 7/2005 | Guzman | |
| 2006/0027744 A1 | 2/2006 | Stults et al. | |
| 2006/0113463 A1 * | 6/2006 | Rossier | H01J 49/167 250/288 |
| 2007/0163884 A1 * | 7/2007 | Strand | G01N 27/44704 204/548 |
| 2008/0035484 A1 * | 2/2008 | Wu | G01N 27/44795 204/548 |
| 2008/0318334 A1 | 12/2008 | Robotti | |
| 2009/0035770 A1 * | 2/2009 | Mathies | B01L 3/502784 435/6.19 |
| 2009/0194419 A1 * | 8/2009 | Huang | C07K 1/36 204/451 |
| 2010/0116659 A1 | 5/2010 | Liu et al. | |
| 2010/0155243 A1 | 6/2010 | Schneider et al. | |
| 2010/0193702 A1 | 8/2010 | Li et al. | |
| 2011/0072914 A1 | 3/2011 | Lebl et al. | |

(56) References Cited

U.S. PATENT DOCUMENTS

| | | | |
|---|---|---|---|
| 2011/0243813 A1 | 10/2011 | Jackinsky et al. | |
| 2012/0080316 A1* | 4/2012 | Schneider | G01N 27/44795 204/603 |
| 2013/0140180 A1 | 6/2013 | Dovichi et al. | |
| 2013/0190212 A1 | 7/2013 | Handique et al. | |
| 2013/0280815 A1 | 10/2013 | Wu et al. | |
| 2013/0319862 A1 | 12/2013 | Kotowski et al. | |
| 2014/0360877 A1 | 12/2014 | Ramsey et al. | |
| 2015/0008130 A1 | 1/2015 | Schneider et al. | |
| 2015/0093757 A1 | 4/2015 | Gavin | |
| 2015/0162177 A1 | 6/2015 | McGivney et al. | |
| 2015/0311056 A1 | 10/2015 | Dovichi et al. | |
| 2015/0340219 A1 | 11/2015 | Mellors et al. | |
| 2015/0362460 A1 | 12/2015 | Ferguson | |
| 2016/0370319 A1 | 12/2016 | Molho et al. | |
| 2017/0025263 A1 | 1/2017 | Mellors et al. | |
| 2017/0045527 A1 | 2/2017 | Muthusamy et al. | |
| 2017/0110307 A1* | 4/2017 | Mellors | G01N 27/4473 |
| 2017/0176386 A1 | 6/2017 | Gentalen | |
| 2017/0299549 A1 | 10/2017 | Schneider et al. | |
| 2017/0363575 A1 | 12/2017 | Huang | |
| 2018/0036729 A1* | 2/2018 | Furtaw | G01N 27/44791 |
| 2018/0036730 A1* | 2/2018 | Furtaw | G01N 27/44756 |
| 2018/0088080 A1 | 3/2018 | Dovichi et al. | |
| 2019/0234961 A1 | 8/2019 | Gentalen | |
| 2019/0367861 A1 | 12/2019 | Swoboda et al. | |
| 2019/0369068 A1 | 12/2019 | Gentalen et al. | |

FOREIGN PATENT DOCUMENTS

| | | |
|---|---|---|
| EP | 1715348 B1 | 2/2011 |
| EP | 1718960 B1 | 3/2012 |
| JP | 4900245 B2 | 3/2012 |
| WO | WO-0015321 A1 | 3/2000 |
| WO | WO-02095362 A2 | 11/2002 |
| WO | WO-2005072121 A2 | 8/2005 |
| WO | WO-2007055293 A1 | 5/2007 |
| WO | WO-2013191908 A1 | 12/2013 |
| WO | WO-2015048458 A2 | 4/2015 |
| WO | WO-2017012397 A1 | 1/2017 |
| WO | WO-2017095813 A1 | 6/2017 |
| WO | WO-2017123970 A1 | 7/2017 |
| WO | WO-2018058131 A1 | 3/2018 |
| WO | WO-2018183622 A1 | 10/2018 |
| WO | WO-2019148198 A1 | 8/2019 |
| WO | WO-2019232397 A1 | 12/2019 |

OTHER PUBLICATIONS

Lalwani et al. (S Lalwani, E Tutu, G Vigh, Isoelectric buffers, part 3: Determination of pKa and pI values of diamino sulfate carrier ampholytes by indirect UV-detection capillary electrophoresis, Electrophoresis 26 (2005) 2503-2510) (Year: 2005).*

Lin et al. (Y Lin, J Wen, X Fan, DW Matson, RD Smith, Laser micromachined isoelectric focusing device on polymer substrate for electrospray mass spectrometry, SPIE Conference on Microfluidic Devices and Systems II, SPIE vol. 3877 (1999) 28-35) (Year: 1999).*

Nordman Supporting Information (N Nordman, S Lauren, T Kotiaho, S Franssila, R Kostiainen, T Sikanen, Interfacing microchip isoelectric focusing with on-chip electrospray ionization mass spectrometry, J. Chromatography A 1398 (2015) 121-126; supporting information) (Year: 2015).*

Cao et al. (J Cao, W Sun, F Gong, W Liu, Charge profiling and stability testing of biosimilar by capillary isoelectric focusing, Electrophoresis, 35 (2014) 1461-1468) (Year: 2014).*

Huhner et al. (J Huhner, M Lammerhofer, C Neusub, Capillary isoelectric focusing-mass spectrometry: coupling strategies and applications, Electrophoresis 36 (2015) 2670-2686) (Year: 2015).*

Wen et al. (J Wen, Y Lin, F Xiang, DW Matson, HR Udseth, RD Smith, Microfabricated isoelectric focusing device for direct electrospray ionization-mass spectrometry, electrophoresis 21 (2000) 191-197) (Year: 2000).*

Hiratsuka et al. (A Hiratsuka, H Kinoshita, Y Maruo, etc., Fully automated two dimensional electrophoresis system for high-throughput protein analysis, Anal. Chem. 79 (2007) 5730-5739) (Year: 2007).*

Mellors et al. (J.S. Mellors, V Gorbounov, R.S. Ramsey, J.M. Ramsey, Fully Integrated Glass Microfluidic Device for Performing High-Efficiency Capillary Electrophoresis and Electrospray Ionization Mass Spectrometry, Anal. Chem. 80 (2008) 6881-6887) (Year: 2008).*

Deng et al. (Y Deng, J Henion, J Li, P Thibault, C Wang, DJ Harrison, Chip-based Capillary Electrophoresis/Mass Spectrometry Determination of Carnitines in Human Urine, Anal. Chem. 73 (2001) 639-646) (Year: 2001).*

Jacobson et al. (SC Jacobson, LB Koutny, R Hergenroder, AW Moore Jr, JM Ramsey, Microchip Capillary Electrophoresis with an Integrated Postcolumn Reactor, Anal. Chem. 66 (1994) 3472-3476) (Year: 1994).*

Nordman et al. (N Nordman, B Barrios-Lopez, S Lauren, P Suvanto, T Kotlaho, S Fransslla, R Kostlalnen, T Slkanen, Shape-anchored porous polymer monoliths for integrated online solid-phase extraction microchip electrophoresis-electrospray ionization mass spectrometry, Electrophoresis 36 (2015) 428-432) (Year: 2015).*

Tang et al. (Q Tang, K Harrata, CS Lee, Capillary isoelectric focusing-electrospray mass spectrometry for protein analysis, Anal. Chem. 67 (1995) 3515-3519) (Year: 1995).*

Baker, C. et al. Online Coupling of Digital Microfluidic Devices with Mass Spectrometry Detection Using an Eductor with Electrospray Ionization. Analytical Chemistry, vol. 84, 2012, 6 pages.

Benz, C. et al. Chip-Based Free-Flow Electrophoresis with Integrated Nanospray Mass-Spectrometry. Angewandte Chemie International Edition, vol. 54, 2015, 5 pages.

Chartogne et al. Capillary electrophoretic separations of proteins using carrier ampholytes. Journal of Chromatography A 959:289-298 (2002).

Chen, et al. Comparison of ampholytes used for slab gel and capillary isoelectric focusing of recombinant tissue-type plasminogen activator glycoforms. J Chromatogr A. Sep. 13, 1996;744(1-2):279-84.

Co-pending U.S. Appl. No. 16/688,141, filed Nov. 19, 2019.

Co-pending U.S. Appl. No. 62/088,353, filed Dec. 5, 2014.

Cui, H. et al. Isoelectric Focusing in a Poly(dimethylsiloxane) Microfluidic Chip. Analytical Chemistry, vol. 77, 2005, 7 pages.

Dai et al. Capillary Isoelectric Focusing-Mass Spectrometry Method for the Separation and Online Characterization of Intact Monoclonal Antibody Charge Variants. Anal Chem. Feb. 6, 2018;90(3):2246-2254.

Deng et al. Chip-Based Capillary Electrophoresis/Mass Spectrometry Determination of Carnitines in Human Urine. Anal Chem 73:639-646 (Feb. 1, 2001).

Dolník, V. Wall coating for capillary electrophoresis on microchips. Electrophoresis. Nov. 2004;25(21-22):3589-601.

Figeys, D. et al. An Integrated Microfluidics-Tandem Mass Spectrometry System for Automated Protein Analysis. Analytical Chemistry, vol. 70, No. 18, Sep. 15, 1998, 7 pages.

Geiser, et al. Potential of formamide and N-methylformamide in nonaqueous capillary electrophoresis coupled to electrospray ionization mass spectrometry. Application to the analysis of beta-blockers. J Chromatogr A. Dec. 6, 2002;979(1-2):389-98.

Gentalen Erik, NIH SBIR Award Abstract #1R44TR002570-01. Award Notice Date: Aug. 10, 2018. 2 pages.

Gentalen Erik, NIH SBIR Award Abstract #4R44TR002570-02. Award Notice Date: Feb. 28, 2019. 2 pages.

Gentalen Erik, NSF SBIR Phase 1 Award Abstract #1747340 (Dec. 18, 2017). 2 pages.

Haselberg, R. et al. Performance of a Sheathless Porous Tip Sprayer for Capillary Electrophoresis-Electrospray Ionization-Mass Spectrometry of Intact Proteins. Journal of Chromatography A, vol. 1217, 2010, 7 pages.

Hühner et al. Capillary isoelectric focusing-mass spectrometry: Coupling strategies and applications. Electrophoresis 36:2670-2686 (2015). First published Aug. 24, 2015. DOI: https://doi.org/10.1002/elps.201500185.

(56) References Cited

OTHER PUBLICATIONS

Hiratsuka et al. Fully Automated Two-Dimensional Electrophoresis System for High-Throughput Protein Analysis. Anal Chem 79(15):5730-5739 (Aug. 1, 2007). Published online Jun. 28, 2007.
Hjertén, Stellan. High-performance electrophoresis : Elimination of electroendosmosis and solute adsorption. Journal of Chromatography A. vol. 347, 1985, pp. 191-198.
Hu, X. et al. Fabrication of a Polystyrene Microfluidic Chip Coupled to Electrospray Ionization Mass Spectrometry for Protein Analysis. Journal of Chromatography B, vol. 990, 2015, 8 pages.
Huang. Finding a Piece of the Protein Characterization Puzzle. The Analytical Chemist, Nov. 2015, pp. 46-48.
International Search Report and Written Opinion dated May 11, 2017 for International PCT Patent Application No. PCT/US2016/064013.
Jacobson et al. Microchip Capillary Electrophoresis with an Integrated Postcolumn Reactor. Anal Chem 66:3472-3476 (Oct. 15, 1994).
Jiang, Y. et al. Integrated Plastic Microfluidic Devices with ESI-MS for Drug Screening and Residue Analysis. Analytical Chemistry, vol. 73, 2001, 6 pages.
Jin et al. Estimation of isoelectric points of human plasma proteins employing capillary isoelectric focusing and peptide isoelectric point markers. Electrophoresis. Sep. 2002;23(19):3385-91.
Karger, et al. High-performance capillary electrophoresis in the biological sciences. J Chromatogr. Aug. 11, 1989;492:585-614.
Lalwani et al. Isoelectric buffers, part 3: Determination of pKa and pI values of diamino sulfate carrier ampholytes by indirect UV-detection capillary electrophoresis. Electrophoresis 26(13):2503-2510 (Jul. 2005). First published Jul. 4, 2005. DOI: https://doi.org/10.1002/elps.200500002.
Li, N. et al. Evaluation of the iCE280 Analyzer as a Potential High-Throughput Tool for Formulation Development. Journal of Pharmaceutical and Biomedical Analysis, vol. 43, 2007, 11 pages.
Li, Y. et al. Integration of Isoelectric Focusing with Parallel Sodium Dodecyl Sulfate Gel Electrophoresis for Multidimensional Protein Separations in a Plastic Microfluidic Network. Analytical Chemistry, vol. 76, 2004, 7 pages.
Lin et al. Laser Micromachined Isoelectric Focusing Device on Polymer Substrate for Electrospray Mass Spectrometry. Part of the SPIE Conference on Microfluidic Devices and Systems II, Santa Clara, CA. SPIE vol. 3877, pp. 28-35 (Sep. 1999).
Mack, et al. A systematic study in CIEF: defining and optimizing experimental parameters critical to method reproducibility and robustness. Electrophoresis. Dec. 2009;30(23):4049-58.
Manabe, et al. Separation of human plasma/serum proteins by capillary isoelectric focusing in the absence of denaturing agents. Electrophoresis. Jun. 1997;18(7):1159-65.
Mao, Q. et al. Demonstration of Isoelectric Focusing on an Etched Quartz Chip with UV Absorption Imaging Detection. Analyst, vol. 124, 1999, 5 pages.
Marasco, C. et al. Real-Time Cellular Exometabolome Analysis With a Microfluidic-Mass Spectrometry Platform. PLOS One, Feb. 27, 2015, 19 pages.
Mellors, J. et al. Fully Integrated Glass Microfluidic Device for Performing High-Efficiency Capillary Electrophoresis and Electrospray Ionization Mass Spectrometry. Analytical Chemistry, vol. 80, 2008, 7 pages.
Michels et al. Imaged Capillary Isoelectric Focusing for Charge-Variant Analysis of Biopharmaceuticals. BioProcess 9(10):48-54 (Nov. 2011).
Michels, et al. Separation Methods and Orthogonal Techniques. State-of-the-Art and Emerging Technologies for Therapeutic Monoclonal Antibody Characterization vol. 2. Biopharmaceutical Characterization: The NISTmAb Case Study. Oct. 15, 2015. Chapter 5, pp. 237-284.
Minarik et al. Dispersion effects accompanying pressurized zone mobilisation in capillary isoelectric focusing of proteins. Journal of Chromatography A. Jun. 1996. 738(1):123-128.
Mohan et al. On-line coupling of capillary isoelectric focusing with transient isotachophoresis-zone electrophoresis: A two-dimensional separation system for proteomics. Electrophoresis 23:3160-3167 (2002).
Mokaddem, et al. Online CIEF-ESI-MS in glycerol—water media with a view to hydrophobic protein applications. Electrophoresis. vol. 30, Issue 23, Dec. 2009. pp. 4040-4048.
Nordman et al. Interfacing Microchip Isoelectric Focusing with On-chip Electrospray: Ionization Mass Spectrometry. Journal of Chromatography A 1398:121-126 (2015). Available online Apr. 23, 2015.
Nordman et al. Interfacing Microchip Isoelectric Focusing with On-chip Electrospray: Ionization Mass Spectrometry, Supplementary Data. Journal of Chromatography A 1398:121-126 (2015). 6 pages. Available online Apr. 23, 2015.
Nordman et al. Shape-anchored porous polymer monoliths for integrated online solid-phase extraction-microchip electrophoresis-electrospray ionization mass spectrometry. Electrophoresis 36:428-432 (2015).
Nordman, N. et al. Rapid Biomolecule Analysis Using Two-Dimensional Electrophoresis-Electrospray Ionization Microchip. 15th International Conference on Miniaturized Systems for Chemistry and Life Science, Oct. 2-6, 2011, Seattle, Washington, 3 pages.
Nordman, N. Microchip Technology in Mass Spectrometry-Based Bioanalysis: Advances in the Analysis of Peptides, Proteins, and Pharmaceuticals. Academic Dissertation, University of Helsinki, Apr. 17, 2015, 144 pages.
PCT/US2019/015701 International Search Report and Written Opinion dated May 31, 2019.
Poitevin, et al. Comparison of different capillary isoelectric focusing methods—use of "narrow pH cuts" of carrier ampholytes as original tools to improve resolution. J Chromatogr A. Jul. 6, 2007;1155(2):230-6.
Procházková et al. Analysis of amino acids by combination of carrier ampholyte-free IEF with ITP. Electrophoresis 28:2168-2173 (2007).
Righetti, et al. Carrier ampholytes for IEF, on their fortieth anniversary (1967-2007), brought to trial in court: the verdict. Electrophoresis. Nov. 2007;28(21):3799-810.
Roy, et al. Surface analysis, hydrophilic enhancement, ageing behavior and flow in plasma modified cyclic olefin copolymer (COC)-based microfluidic devices. Sensors and Actuators B: Chemical. vol. 150, Issue 2, Oct. 28, 2010, pp. 537-549.
Salas-Solano et al. Robustness of iCIEF Methodology for the Analysis of Monoclonal Antibodies: An Interlaboratory Study. Journal of Separation 35:3124-3129 (2012).
Salas-Solano, O. et al. Intercompany Study to Evaluate the Robustness of Capillary Isoelectric Focusing Technology for the Analysis of Monoclonal Antibodies. Chromatographia, vol. 73, 2011, 8 pages.
Scientific Considerations in Demonstrating Biosimilarity to a Reference Product: Guidance for Industry, U.S. Department of Health and Human Services Food and Drug Administration, Apr. 2015. 27 pages. Retrieved Feb. 12, 2019 from URL:<https://www.fda.gov/downloads/drugs/guidances/ucm291128.pdf>.
Shimura, K. et al. Isoelectric Focusing in a Microfluidically Defined Electrophoresis Channel. Analytical Chemistry, vol. 80, 2008, 6 pages.
Sikanen, T. et al. Intact Protein Separations With Inherently Biocompatible Ormocomp Separation Chip With Integrated Electrospray Ionization Emitter. 15th International Conference on Miniaturized Systems for Chemistry and Life Science, Oct. 2-6, 2011, Seattle, Washington, 3 pages.
Sikanen, T. et al. Microchip Capillary Electrophoresis-Electrospray Ionization-Mass Spectrometry of Intact Proteins Using Uncoated Ormocomp Microchips. Analytica Chimica Acta, vol. 711, 2012, 8 pages.
Sikanen, T. et al. Microchip Technology in Mass Spectrometry. Mass Spectrometry Reviews, vol. 29, 2010, 41 pages.
Sung, et al. Chip-based microfluidic devices coupled with electrospray ionization-mass spectrometry. Electrophoresis. vol. 26, Issue 9, No. 9, May 2005. pp. 1783-1791.

(56) References Cited

OTHER PUBLICATIONS

Suzuki, S. et al. High-speed Electrophoretic Analysis of 1-phenyl-3-methyl-5-pyrazolone Derivatives of Monosaccharides on a Quartz Microchip with Whole-Channel UV Detection. Electrophoresis, vol. 24, 2003, 6 pages.
Tan, W. et al. Miniaturized Capillary Isoelectric Focusing in Plastic Microfluidic Devices. Electrophoresis, vol. 23, 2002, 8 pages.
Tang et al. Comparison of Protein Separations in Capillary Zone Electrophoresis and Capillary Isoelectric Focusing Interfacing with Electrospray Mass Spectrometry. Journal of Mass Spectrometry. Nov. 1996. 31(11):1284-1290.
Taylor, P. Matrix Effects: The Achilles Heel of Quantitative High-Performance Liquid Chromatography-Electrospray-Tandem Mass Spectrometry. Clinical Biochemistry, vol. 38, 2005, 7 pages.
Tentori et al. Detection of Isoforms Differing by a Single Charge Unit in Individual Cells. Angew Chem Ed 55 (2016). 6 pages.
Tentori et al. Supporting Information: Detection of Isoforms Differing by a Single Charge Unit in Individual Cells. Angew Chem Ed 55 (2016). 25 pages.
Tentori et al. Performance implications of chemical mobilization after microchannel IEF. Electrophoresis 35:1453-1460 (2014).
Thormann et al. High-resolution computer simulation of electrophoretic mobilization in isoelectric focusing. Electrophoresis 29:1676-1686 (2008).
Týčová et al. Recent advances in CE-MS coupling: Instrumentation, methodology, and applications. Electrophoresis. Jan. 2017;38(1):115-134.
U.S. Appl. No. 15/709,158 Notice of Allowance dated Nov. 30, 2018.
U.S. Appl. No. 15/709,158 Office Action dated Aug. 9, 2018.
U.S. Appl. No. 15/709,158 Office Action dated Dec. 21, 2017.
U.S. Appl. No. 16/224,558 Office Action dated Apr. 12, 2019.
U.S. Appl. No. 15/709,158 Office Action dated Feb. 27, 2018.
"U.S. Appl. No. 15/709,158 Office Action dated Jun. 18, 2018".
Vagenende, et al. Mechanisms of protein stabilization and prevention of protein aggregation by glycerol. Biochemistry. Nov. 24, 2009;48(46):11084-96.
Vlckova, M. et al. Pharmaceutical Applications of Isoelectric Focusing on Microchip With Imaged UV Detection. Journal of Chromatography A, vol. 1181, 2008, 8 pages.
Wakankar, A. et al. Analytical Methods for Physicochemical Characterization of Antibody Drug Conjugates. mAbs, vol. 3, No. 2, Mar./Apr. 2011, 12 pages.
Wang et al. High Resolution Capillary Isoelectric Focusing Mass Spectrometry Analysis of Peptides, Proteins and Monoclonal Antibodies with a Flow-Through Microvial Interface. Anal Chem 90(15):9495-9503 (Jul. 11, 2018).DOI: 10.1021/acs.analchem.8b02175.
Wehr. Chapter 9: Capillary Isoelectric Focusing. Handbook of Isoelectric Focusing and Proteomics, D. Garfin and S. Ahuja, Eds., Elsevier Inc. pp. 181-210 (2005).
Wen, J. et al. Microfabricated Isoelectric Focusing Device for Direct Electrospray Ionization-Mass Spectrometry. Electrophoresis, vol. 21, 2000, 7 pages.

Wu, et al. Secrets of iCE Method Design for Protein Therapeutics. Protein Simple. Presentation Abstract. Tuesday Mar. 27, 2012. URL: <http://events.r20.constantcontact.com/register/event?llr=p9xbiodab&oeidk=a07e5nz3rtw6f41039b>.
Wu, J. et al. Absorption Spectra and Multicapillary Imaging Detection for Capillary Isoelectric Focusing Using a Charge Coupled Device Camera. Analyst, vol. 120, May 1995, 5 pages.
Wu, J. et al. Capillary Isoelectric Focusing with Whole col. Detection and a Membrane Sample Preparation System. Analytica Chimica Acta, vol. 383, 1999, 12 pages.
Wu, J. J et al. Protein Analysis by Isoelectric Focusing in a Capillary Array With an Absorption Imaging Detector. Journal of Chromatography B, vol. 669, 1995, 5 pages.
Yang et al. Capillary isoelectric focusing-electrospray ionization mass spectrometry for transferrin glycoforms analysis. Anal Biochem. Dec. 1, 1996;243(1):140-9.
Zhang, B. et al. Microfabricated Devices for Capillary Electrophoresis-Electrospray Mass Spectrometry. Analytical Chemistry, vol. 71, 1999, 7 pages.
Zhang et al. Stepwise Mobilization of Focused Proteins in Capillary Isoelectric Focusing Mass Spectrometry. Analytical Chemistry 72(7):1462-1468 (Apr. 1, 2000). Published online Mar. 3, 2000. DOI: https://doi.org/10.1021/ac9912653.
Zhong, X, et al. Flow-Through Microvial Facilitating Interface of Capillary Isoelectric Focusing and Electrospray Ionization Mass Spectrometry. Analytical Chemistry, vol. 83, 2011, 8 pages.
Co-pending U.S. Appl. No. 16/799,387, filed Feb. 24, 2020.
Co-pending U.S. Appl. No. 16/808,063, filed Mar. 3, 2020.
Hiroaki Nakanishi, et. al. Fabrication of Quartz Microchips with Optical Slit and Development of a Linear Imaging UV Detector for Microchip Electrophoresis Systems, Electrophoresis (2001), vol. 22, pp. 230-234.
Kitagawa. et al., High-speed Analysis of Proteins by Microchip Isoelectric Focusing with Linear-imaging UV Detection, Analytical Sciences, Aug. 2009, vol. 25, 979-984.
Mitsuhiro Kinoshita, Quality Assurance of Monoclonal Antibody Pharmaceuticals Based on Their Charge Variants Using Microchip Isoelectric Focusing Method, Journal of Chromatography A (2013), vol. 1309 pp. 76-83.
U.S. Appl. No. 16/261,382 Notice of Allowance dated Jan. 29, 2020.
U.S. Appl. No. 16/261,382 Office Action dated May 22, 2019.
U.S. Appl. No. 16/261,382 Office Action dated Oct. 1, 2019.
Zhong et al. Mass Transport in a Micro Flow-Through Vial of a Junction-at-the-Tip Capillary Electrophoresis-Mass Spectrometry Interface. Anal Chem 83(12):4916-4923 (Apr. 29, 2011).
Co-pending U.S. Appl. No. 16/983,293, filed Aug. 3, 2020.
Ross et al. Simple device for multiplexed electrophoretic separations using gradient elution moving boundary electrophoresis with channel current detection. Anal Chem. Dec. 15, 2008;80(24):9467-74.doi: 10.1021/ac801597e.
Herr et al., On-Chip Coupling of Isoelectric Focusing and Free Solution Electrophoresis for Multidimensional Separations, Anal. Chem., Mar. 1, 2003, 75:1180-87.

\* cited by examiner

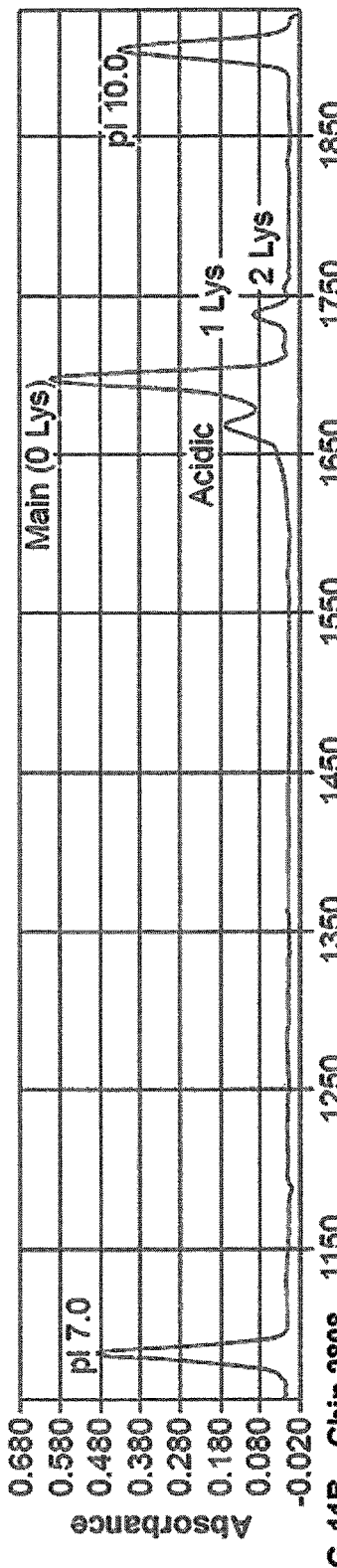
FIG. 11A – Chip 2811
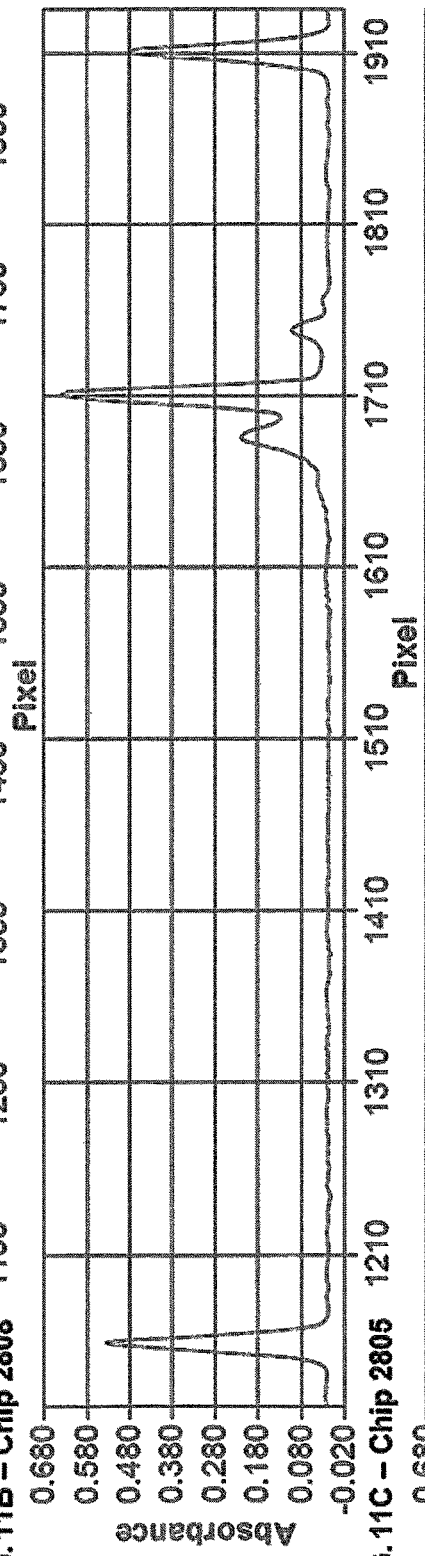
FIG. 11B – Chip 2808
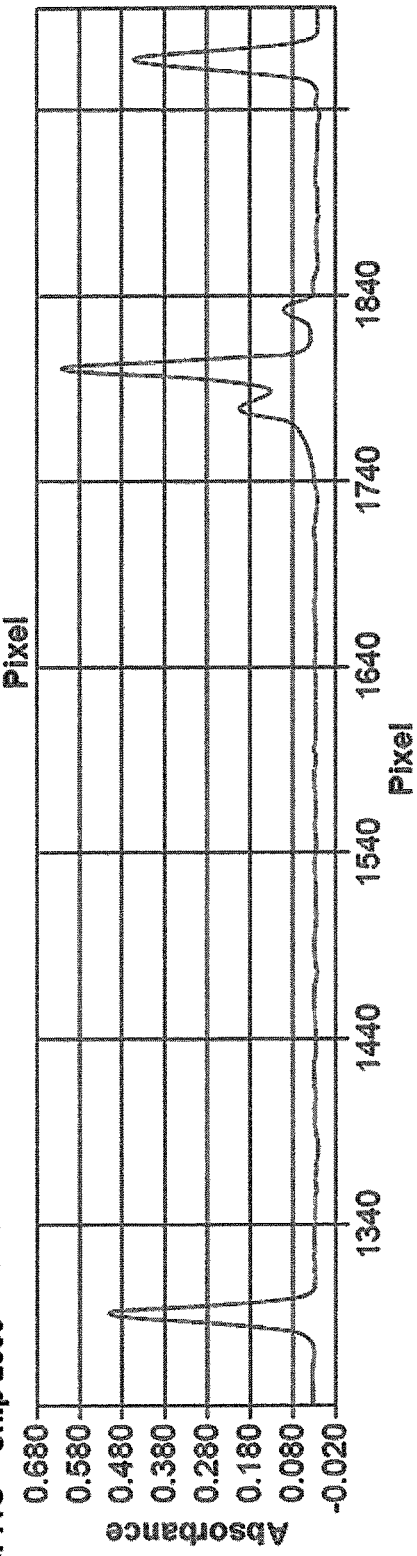
FIG. 11C – Chip 2805

DEVICES, METHODS AND KITS FOR SAMPLE CHARACTERIZATION

CROSS-REFERENCE TO RELATED APPLICATIONS

This application is a continuation application of U.S. patent application Ser. No. 16/261,382, filed Jan. 29, 2019, which claims the benefit of U.S. Provisional Patent Application No. 62/623,492, filed on Jan. 29, 2018, both of which applications are incorporated herein by reference in their entirety.

BACKGROUND

This disclosure relates to devices and methods for sample processing and characterization, and various uses thereof. In particular, this disclosure relates to devices and methods for separation and characterization of analytes in a mixture of analytes.

Separation of analyte components from a more complex analyte mixture on the basis of one or more inherent qualities of the analytes, and optionally providing sets of sample fractions that are enriched for specific analyte components, is a key part of analytical chemistry. Simplifying complex mixtures in this manner reduces the complexity of downstream analysis. In some cases, it can be advantageous to perform two or more enrichment steps that are orthogonal (e.g., based on different and/or unrelated qualities). In many cases, however, the process of performing orthogonal enrichment steps using known methods and/or devices is cumbersome, and can dilute the analyte to a concentration that is beyond the detection sensitivity of the downstream analytical equipment. In addition, complications can arise when attempting to interface known enrichment methods and/or devices with analytical equipment and/or techniques. In some instances, sample separation and/or enrichment may be performed upstream or in parallel with sample analysis. For example, devices for performing sample enrichment may be coupled directly with an analytical instrument.

A variety of methods have been used, for example, to interface protein sample preparation techniques with downstream detection systems such as mass spectrometers. A common method is to prepare samples using liquid chromatography and collect fractions for mass spectrometry. This has the disadvantage of requiring protein samples to be separated into a large number of sample fractions which must be analyzed, and complex data reconstruction must be performed post-run. While certain forms of liquid chromatography can be coupled to a mass spectrometer (LC-MS), for example peptide map reversed-phase chromatography, these known techniques are restricted to using peptide fragments, rather than intact proteins, which limits their utility.

Another method to introduce samples into a mass spectrometer is electrospray ionization (ESI). In ESI, small droplets of sample and solution at a distal end of a capillary or microfluidic device are ionized to induce an attraction to the charged plate of a mass spectrometer. The droplet then stretches in this induced electric field to a cone shape ("Taylor cone"), which then releases small droplets into the mass spectrometer for analysis. Typically this is done in a capillary, which provides a convenient volume and size for ESI. Capillaries however, provide a linear flow path that does not allow for multi-step processing.

Other work has been pursued with microfluidic devices. Microfluidic devices may be produced by various known techniques and provide fluidic channels of defined dimensions that can make up a channel network designed to perform different fluid manipulations. These devices offer an additional level of control and complexity compared to capillaries, making them a better choice for sample prep. However, as with capillary-based systems, these tools often provide limited characterization of separated analyte fractions prior to introduction to a mass spectrometer.

One application for protein mass spectrometry is characterization of proteins during the development and manufacturing of biologic and biosimilar pharmaceuticals. Biologics and biosimilars are a class of drugs which include, for example, recombinant proteins, antibodies, live virus vaccines, human plasma-derived proteins, cell-based medicines, naturally-sourced proteins, antibody-drug conjugates, protein-drug conjugates and other protein drugs.

Regulatory compliance requires extensive testing of biologics during development and manufacture, something that is not required for small molecule drugs. This is because the manufacture of biologics has greater complexity due to, for example, using living material to produce the biologic, the greater complexity of the biologic molecule itself, and greater complexity of the manufacturing process. Characteristics required to be defined include, for example, mass, charge, changes in hydrophobicity, and glycosylation state, as well as efficacy. Currently these tests are performed independently of each other, leading to a very time consuming and expensive process for characterizing biologics.

Methods, devices, and systems for performing analyte separations, improving the accuracy of quantitative separation data, and achieving improved correlation between the quantitative separation data and downstream analytical characterization data, e.g., mass spectrometry characterization data, are described in the present disclosure.

SUMMARY

Disclosed herein are methods, devices, and systems that enable improved quantitative performance for the separation and analysis of analytes in an analyte mixture, with potential applications in biomedical research, clinical diagnostics, and pharmaceutical manufacturing. For example, rigorous characterization of biologic drugs and drug candidates (e.g., proteins) are required by regulatory agencies. The methods and devices described herein may be suitable for characterizing proteins and/or other analytes. In some instances, the methods and devices described herein may relate to characterizing an analyte mixture wherein one or more enrichment steps are performed to separate an analyte mixture into enriched analyte fractions. In some instances, the methods and devices described herein relate to characterizing an analyte mixture wherein one or more enrichment steps are performed to separate an analyte mixture into enriched analyte fractions that are subsequently introduced into a mass spectrometer via an electrospray ionization interface. The disclosed methods and devices may provide improvements in convenience, reproducibility, and/or analytical performance of analyte separation and characterization.

Disclosed herein are methods for introducing a mobilization electrolyte into a separation channel comprising a plurality of separated analytes, the method comprising: using data derived from images of the separated analytes to automatically initiate introduction of the mobilization electrolyte into the separation channel.

In some embodiments, the separation channel is a microchannel in a microfluidic device. In some embodiments, the separation channel is a capillary. In some embodiments, the method further comprises separating the plurality of analytes by isoelectric focusing. In some embodiments, the method further comprises mobilizing the separated analytes towards an electrospray ionization interface with a mass spectrometer. In some embodiments, mobilization electrolyte comprises a zwitterionic buffer. In some embodiments, the mobilization electrolyte comprises acetic acid, formic acid, carbonic acid, or any combination thereof. In some embodiments, the method further comprises acquiring images of all or a portion of the separation channel. In some embodiments, the images are acquired using light transmitted through the separation channel. In some embodiments, the images are UV absorbance images or fluorescence images. In some embodiments, the image-derived data comprises separated analyte peak information selected from the group consisting of peak position, peak width, and peak velocity. In some embodiments, introduction of the mobilization electrolyte is performed electrophoretically. In some embodiments, the electrophoretic introduction of mobilization electrolyte enables more accurate pI determinations for one or more separated analytes.

Also disclosed herein are systems comprising: a) a separation channel for performing isoelectric focusing to separate a mixture of analytes contained therein; b) a mobilization channel that intersects with a distal end of the separation channel for delivery of a mobilization electrolyte to the separation channel; and c) three electrodes comprising a first electrode that is electrically-coupled to a proximal end of the separation channel, a second electrode that is electrically-coupled to the distal end of the separation channel, and a third electrode that is electrically-coupled with the mobilization channel; wherein the electrical-coupling of the second or third electrodes with their respective channels is switchable between on and off states.

In some embodiments, the first electrode is an anode and the second and third electrodes are cathodes. In some embodiments, the switching of the second or third electrodes between on and off states initiates an electrophoretic introduction of the mobilization electrolyte into the separation channel. In some embodiments, the electrophoretic introduction of the mobilization electrolyte leads to improved separation resolution after mobilization compared that attained at the completion of an isoelectric focusing separation. In some embodiments, the system is configured to switch the second or third electrodes between on and off states at a user-specified time following an initiation of an isoelectric focusing separation. In some embodiments, the system is configured to monitor a current flowing through the separation channel during an isoelectric focusing separation reaction and switch the second or third electrodes between on and off states when the current drops below a specified current threshold. In some embodiments, the system further comprises: (i) an imaging unit, and (ii) a processor unit, wherein a series of images captured by the imaging unit as the separation is performed are further processed by the processor unit to generate a trigger signal that triggers the switching of the second and third electrodes between on and off states in an asymmetric manner. In some embodiments, the imaging unit is configured to capture images of all or a portion of the separation channel. In some embodiments, the imaging unit is configured to capture images using light transmitted through a separation channel window. In some embodiments, the imaging unit is configured to capture UV absorbance images or fluorescence images. In some embodiments, the series of images are acquired at a rate of at least 1 image every 15 seconds. In some embodiments, the processor unit is configured to perform an image processing algorithm used to monitor the presence or absence of an analyte peak in the separation channel. In some embodiments, the system is configured to maintain the third electrode in an off state if no analyte peak is detected in the separation channel. In some embodiments, the processor unit is configured to perform an image processing algorithm used to monitor changes in position of separated analyte peaks over time or changes in the width of separated analyte peaks over time. In some embodiments, an absence of change or a reduction in a rate of change in peak position or peak width for one or more separated analyte peaks over a time period of at least 20 seconds triggers the switching of the second and third electrodes between on and off states. In some embodiments, the time period is at least 30 seconds, 40 seconds, 50 seconds, or 30 seconds. In some embodiments, the system further comprises an orifice in fluid communication with the distal end of the separation channel, wherein the orifice is configured to function as an electrospray ionization interface with a mass spectrometer.

Disclosed herein are devices as illustrated in any one of FIG. 1, 4, 5, 7, 8, or 9. In some embodiments, the device may comprise at least one separation or enrichment channel. In some embodiments, the device may be configured to perform isoelectric focusing in at least one separation or enrichment channel. In some embodiments, the device may be configured to perform electrophoretic introduction of a mobilization agent into the separation or enrichment channel following completion of an isoelectric focusing step. In some embodiments, the device may comprise (a) a separation channel for performing isoelectric focusing to separate a mixture of analytes contained therein; (b) a mobilization channel that intersects with a distal end of the separation channel for delivery of a mobilization electrolyte to the separation channel; and (c) three electrodes comprising a first electrode that is electrically-coupled to a proximal end of the separation channel, a second electrode that is electrically-coupled to the distal end of the separation channel, and a third electrode that is electrically-coupled with the mobilization channel; wherein the electrical-coupling of the second or third electrodes with their respective channels is switchable between on and off states.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A: upper layer. FIG. 2B: middle ("fluidics") layer. FIG. 2C: bottom layer. FIG. 2D: assembled device.

FIGS. 11A-C provide a non-limiting example of the repeatability for separation data when separations performed in different microfluidic devices of the same design. FIG. 11A: data for chip number 2811. FIG. 11B: data for chip number 2808. FIG. 11C: data for chip number 2805.

DETAILED DESCRIPTION

Figure 1A:
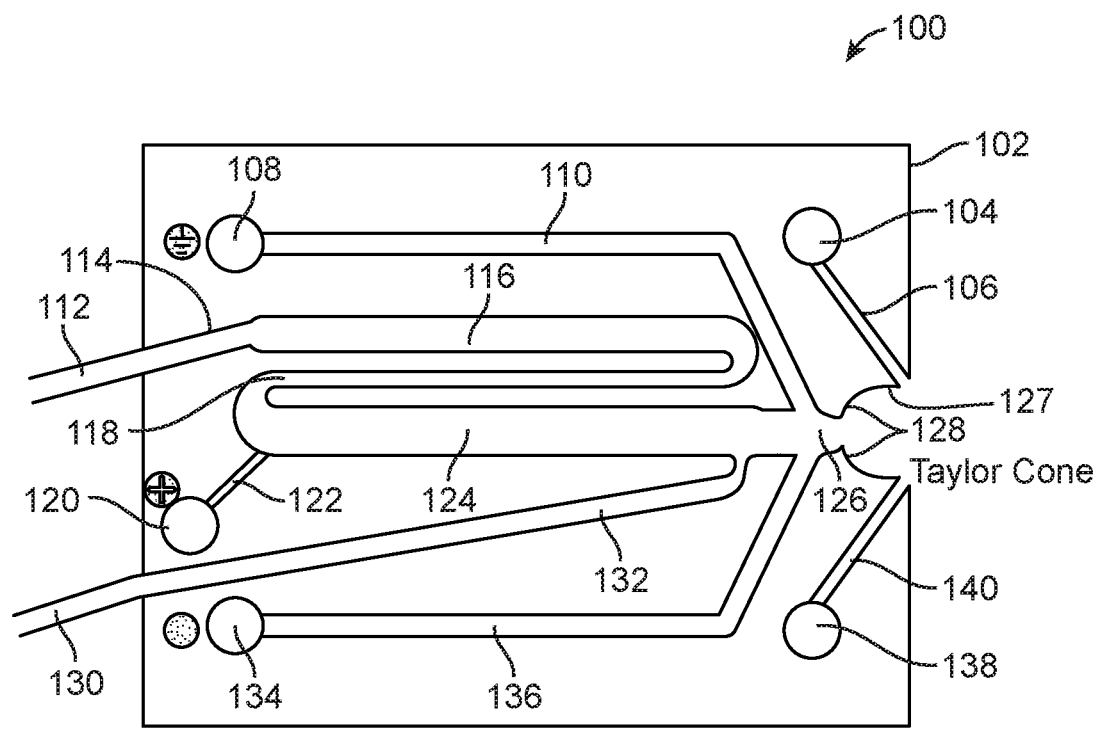
FIGS. 1A and 1B provide schematic illustrations of a microfluidic device for performing two dimensional separations of analytes and subsequent electrospray ionization (ESI) of an automatically loaded sample, according to one aspect of this disclosure.

Disclosed herein are methods, devices, and systems for separating analyte mixtures contained in a sample into their individual components, and characterizing the physical and/or chemical properties thereof with improved reproducibility, accuracy, and precision. In particular, methods and devices for performing sample separation and enrichment using techniques such as isoelectric focusing (IEF), followed by characterization of individual analyte components using analytical instrument such as mass spectrometry are described. The disclosed methods, devices, and systems enable improvements in the reproducibility and quantitative accuracy of the separation data, and also improved correlation between the separation data and downstream analytical characterization data, e.g., that obtained using a mass spectrometer or other analytical instrument.

One key feature of the disclosed methods, devices, and systems is the use of electrodes that are switchable between on and off states to control the electrophoretic introduction of a mobilization buffer or electrolyte into a separation channel following the complete of a separation reaction, e.g., an isoelectric focusing reaction, thereby triggering the mobilization step that causes migration of one or more separated analyte peaks within the separation channel towards an outlet or distal end of the separation channel. In some instances, the time required to reach completion of a separation reaction, e.g., the completion of an isoelectric focusing reaction, is known and the initiation of the mobilization step is set at a user-specified time. In some instances, completion of the separation step is detected by, e.g., monitoring the current through the separation channel when isoelectric focusing is performed. In some instances, completion of the separation reaction is detected using continuous or periodic imaging of all or a portion of the separation channel to monitor the separation reaction as it is performed. In some instances, data derived from processing images of the separation channel is used not only to determine when the separation reaction has been completed, but to generate a trigger signal to automatically trigger the switching of electrodes and thereby initiate electrophoretic introduction of a mobilization electrolyte. In some instances, introduction of a mobilization electrolyte into the separation channel (e.g., using an electric field for electrophoretic introduction of the mobilizing agent and/or hydrodynamic pressure to introduce the mobilizing agent) initiates the mobilization of separated analyte peaks in a manner that minimizes peak broadening during the migration of analyte peaks towards the outlet or distal end of the separation channel. In some instances, the introduction of the mobilization electrolyte into the separation channel using electrophoretic and/or hydrodynamic pressure results in narrowing of the analyte peaks (i.e., thereby yielding improved separation resolution) during the migration of the analyte peaks towards the outlet or distal end of the separation channel.

Another key feature of the disclosed methods, devices, and systems, as indicated above, is the use of imaging to monitor separation reactions in a separation channel for the purpose of detecting the presence of analyte peaks and/or to determine when the separation reaction has reached completion. In some instances, images may be acquired for all or a portion of the separation channel. In some instances, the images may be used to detect the position of enriched analyte peaks within the separation channel. In some instances, the images may be used to detect the presence of one or more markers or indicators, e.g., isoelectric point (pI) standards, within the separation channel and thus determine the pIs for one or more analytes. In some instances, data derived from such images may be used to determine when a separation reaction is complete (e.g., by monitoring peak velocities, peak positions, and/or peak widths) and subsequently trigger a mobilization step. In some instances, the mobilization step may comprise introduction of a mobilization buffer or a mobilization electrolyte into the separation channel. In some instances, the mobilization buffer or mobilization electrolyte may be introduced using hydrodynamic pressure. In some instances, the mobilization buffer or mobilization electrolyte may be introduced by means of electrophoresis. In some instances, the mobilization buffer or mobilization electrolyte may be introduced by means of a combination of electrophoresis and hydrodynamic pressure. In some instances, the mobilization of a series of one or more separated analyte bands may comprise causing the separated analyte bands to migrate towards an outlet or distal end of the separation channel. In some instances, the mobilization of a series of one or more separated analyte bands may comprise causing the separated analyte bands to migrate towards an outlet or distal end of the separation channel that is in fluid communication with a downstream analytical instrument. In some instances, the outlet or distal end of the separation channel may be in fluid communication with an electrospray ionization (ESI) interface such that the migrating analyte peaks are injected into a mass spectrometer. In some instances, the image data used to detect analyte peak positions and determine analyte pIs may also be used to correlate analyte separation date with mass spectrometry data.

In preferred aspects, the disclosed methods may be performed in a microfluidic device format, thereby allowing for processing of extremely small sample volumes and integration of two or more sample processing and separation steps. In another preferred aspect, the disclosed microfluidic devices comprise an integrated interface for coupling to a downstream analytical instrument, e.g., an ESI interface for performing mass spectrometry on the separates analytes. In some instances, the disclosed methods may be performed in a more conventional capillary format.

Various aspects of the disclosed methods, devices, and systems described herein may be applied to any of the particular applications set forth below, or for any other type of sample analysis application. It shall be understood that different aspects of the disclosed methods, devices, and systems can be appreciated individually, collectively, or in combination with each other.

Definitions: Unless otherwise defined, all of the technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated. Similarly, the terms "comprise", "comprises", "comprising", "include", "includes", and "including" are not intended to be limiting.

As used herein, the phrases "including, but not limited to . . . " and "one non-limiting example is . . . " are meant to be inclusive of variations and derivatives of the given example, as commonly understood by one of ordinary skill in the art in the field to which this disclosure belongs.

As used herein, the term 'about' a number refers to that number plus or minus 10% of that number. The term 'about' when used in the context of a range refers to that range minus 10% of its lowest value and plus 10% of its greatest value.

As used herein, the terms "characterization" and "analysis" may be used interchangeably. To "characterize" or "analyze" may generally mean to assess a sample, for example, to determine one or more properties of the sample or components thereof, or to determine the identity of the sample.

As used herein, the terms "chip" and "device" may be used interchangeably herein.

As used herein, the terms "analyte" and "species" may be used interchangeably. An analyte generally means a molecule, biomolecule, chemical, macromolecule, etc., that differs from another molecule, biomolecule, chemical, macromolecule, etc. in a measureable property. For example, two species may have a slightly different mass, hydrophobicity, charge or net charge, isoelectric point, efficacy, or may differ in terms of chemical modifications, protein modifications, etc.

Methods for Sample Analysis

Disclosed herein are methods for sample analysis that include introducing an analyte mixture into a microfluidic device that contains a separation channel. In some instances pressure may be applied across the separation channel to affect a separation of the analyte mixture. In some instances, an electric field may be applied across the separation channel to affect a separation of the analyte mixture. In some instances, the analyte mixture may be imaged during separation via, e.g., a transparent portion of the microfluidic device. For example, a window and/or optical slit may be used to provide optical access to the separation channel such that the whole separation channel or a portion thereof can be imaged while the separation is occurring and/or as the separated analyte fractions are mobilized towards an outlet of the separation channel. In some instances, at least a fraction of the analyte mixture may be expelled from an orifice that is in fluid communication with the separation channel. For example, at least a fraction of the analyte mixture (e.g., one or more separated analyte bands or peaks) may be expelled via ESI. In some instances in which electrospray ionization is used to interface the separation device with a mass spectrometer, the orifice may be disposed on a countersunk surface of the microfluidic device such that a Taylor cone forms within a recess defined by the countersunk surface.

The disclosed methods for analyzing samples may thus comprise one or more of: (i) introducing a sample comprising an analyte mixture into a separation channel, (ii) performing one or more separation or enrichment steps to separate analytes from the mixture of analytes contained in the sample, (iii) periodically or continuously imaging of all or a portion of the separation channel while a separation step and/or a mobilization step is performed, (iv) introduction of a mobilization buffer or mobilization electrolyte into the separation channel, wherein the introduction is triggered automatically based on a user-specified time, the level of current flowing through the separation channel, and/or data derived from images of the separation channel, (v) electrophoretic and/or pressure-induced introduction of a mobilization agent and subsequent mobilization of separated analyte peaks or enriched analyte fractions out of a separation channel towards an outlet or distal end of the separation channel, (vi) transfer of one or more mobilized analyte peaks or enriched analyte fractions to a downstream analytical instrument, or (vii) any combination thereof. Analysis of analytes may comprise any of a variety of methods, such as measuring absorbance or fluorescence signals, imaging to detect the presence, position, and/or peak width of one or more separated analyte peaks or bands, determination of mass, analysis of chemical structure, etc.

Samples: The disclosed methods, devices, systems, and software may be used for separation and characterization of analytes obtained from any of a variety of biological or non-biological samples. Examples include, but are not limited to, tissue samples, cell culture samples, whole blood samples (e.g., venous blood, arterial blood, or capillary blood samples), plasma, serum, saliva, interstitial fluid, urine, sweat, tears, protein samples derived from industrial enzyme or biologic drug manufacturing processes, environmental samples (e.g., air samples, water samples, soil samples, surface swipe samples), and the like. In some embodiments, the samples may be processed using any of a variety of techniques known to those of skill in the art prior to analysis using the disclosed methods and devices for integrated chemical separation and mass spectrometric characterization. For example, in some embodiments the samples may be processed to extract proteins or nucleic acids. Samples may be collected from any of a variety of sources or subjects, e.g., bacteria, virus, plants, animals, or humans.

Sample volumes: In some instances of the disclosed methods and devices, the use of microfluidic devices may enable the processing of very small sample volumes. In some embodiments, the sample volume loaded into the device and used for analysis may range from about 0.1 µl to about 1 ml. In some embodiments, the sample volume loaded into the device and used for analysis may be at least 0.1 µl, at least 1 µl, at least 2.5 µl, at least 5 µl, at least 7.5 µl, at least 10 µl, at least 25 µl, at least 50 µl, at least 75 µl, at least 100 µl, at least 250 µl, at least 500 µl, at least 750 µl, or at least 1 ml. In some embodiments, the sample volume loaded into the device and used for analysis may be at most 1 ml, at most 750 µl, at most 500 µl, at most 250 µl, at most 100 µl, at most 75 µl at most 50 µl at most 25 µl, at most 10 µl, at most 7.5 µl, at most 5 µl, at most 2.5 µl, at most 1 µl or at most 0.1 µl. Any of the lower and upper values described in this paragraph may be combined to form a range included within the present disclosure, for example, in some embodiments the sample volume loaded into the device and used for analysis may range from about 5 µl to about 500 µl. Those of skill in the art will recognize that sample volume used for analysis may have any value within this range, e.g., about 18 µl.

Analytes: In some instances, a sample may comprise a plurality of analyte species. In some instances, all or a portion of the analyte species present in the sample may be enriched prior to or during analysis. In some instances, these analytes can be, for example, glycans, carbohydrates, DNA, RNA, recombinant proteins, intact proteins, protein isoforms, digested proteins, fusion proteins, antibody-drug conjugates, protein-drug conjugates, peptides, metabolites or other biologically relevant molecules. In some instances, these analytes can be small molecule drugs. In some instances, these analytes can be protein molecules in a protein mixture, such as a biologic protein pharmaceutical and/or a lysate collected from cells isolated from culture or in vivo.

Separation and enrichment of analytes: In some instances, the disclosed methods (and devices or systems configured to perform said methods) may comprise one or more separation or enrichment steps in which a plurality of analytes in a mixture are separated and/or concentrated in individual fractions. For example, in some instances the disclosed methods may comprise a first enrichment step, in which fractions containing a subset of the analyte molecules from the original sample or analyte mixture are eluted one fraction at a time; these enriched analyte fractions may then be subjected to another enrichment step. Following a final enrichment step, the enriched analyte fractions are expelled for further analysis.

In some instances, the disclosed methods may comprise one, two, three, four, or five or more separation and/or enrichment steps. In some embodiments, one or more of the separation or enrichment steps will comprise a solid-phase separation technique, e.g., reverse-phase HPLC. In some embodiments, one or more of the separation or enrichment steps will comprise a solution-phase separation technique, e.g., capillary zone electrophoresis (CZE). In some embodiments, a final step, e.g., isoelectric focusing (IEF) is used to concentrate the enriched analyte fractions before expulsion.

The disclosed methods (and devices or systems configured to perform said methods) may comprise any of a variety of analyte separation or enrichment techniques known to those of skill in the art, where the separation or enrichment step(s) are performed in at least a first separation channel that is configured to be imaged so that the separation process may be monitored as it is performed. For example, in some instances the imaged separation may be an electrophoretic separation comprising, e.g., isoelectric focusing, capillary gel electrophoresis, capillary zone electrophoresis, isotachophoresis, capillary electrokinetic chromatography, micellar electrokinetic chromatography, flow counterbalanced capillary electrophoresis, electric field gradient focusing, dynamic field gradient focusing, and the like, that produces one or more separated analyte fractions from an analyte mixture.

Capillary isoelectric focusing (CIEF): In some instances, the separation technique may comprise isoelectric focusing (IEF), e.g., capillary isoelectric focusing (CIEF). Isoelectric focusing (or "electrofocusing") is a technique for separating molecules by differences in their isoelectric point (pI), i.e., the pH at which they have a net zero charge. CIEF involves adding ampholyte (amphoteric electrolyte) solutions to reagent reservoirs containing an anode or a cathode to generate a pH gradient within a separation channel (i.e., the fluid channel connecting the electrode-containing wells) across which a separation voltage is applied. Negatively charged molecules migrate through the pH gradient in the medium toward the positive electrode while positively charged molecules move toward the negative electrode. A protein (or other molecule) that is in a pH region below its isoelectric point (pI) will be positively charged and so will migrate towards the cathode (i.e., the negatively charged electrode). The protein's overall net charge will decrease as it migrates through a gradient of increasing pH (due, for example, to protonation of carboxyl groups or other negatively charged functional groups) until it reaches the pH region that corresponds to its pI, at which point it has no net charge and so migration ceases. As a result, a mixture of proteins separates based on their relative content of acidic and basic residues and becomes focused into sharp stationary bands with each protein positioned at a point in the pH gradient corresponding to its pI. The technique is capable of extremely high resolution with proteins differing by a single charge being fractionated into separate bands. In some embodiments, isoelectric focusing may be performed in a separation channel that has been permanently or dynamically coated, e.g., with a neutral and hydrophilic polymer coating, to eliminate electroosmotic flow (EOF). Examples of suitable coatings include, but are not limited to, polyacrylamide, linear polyacrylamide, hydroxyprolycellulose (HPC), polyvinylalcohol (PVA), or Guarant coating (Alcor Bioseparations, Palo Alto, Calif.). In some embodiments, isoelectric focusing may be performed (e.g., in uncoated separation channel) using additives such as methylcellulose or glycerol in the separation medium to significantly decrease the electroosmotic flow, allow better protein solubilization, and limit diffusion inside the capillary of fluid channel by increasing the viscosity of the electrolyte.

As noted above, the pH gradient used for capillary isoelectric focusing techniques is generated through the use of ampholytes, i.e., amphoteric molecules that contain both acidic and basic groups and that exist mostly as zwitterions within a certain range of pH. That portion of the electrolyte solution on the anode side of the separation channel is known as an "anolyte". That portion of the electrolyte solution on the cathode side of the separation channel is known as a "catholyte". Ampholytes for use in isoelectric focusing may thus comprise the use of acid/base pairs (or anolyte/catholyte pairs). Any of a variety of ampholytes known to those of skill in the art may be used in the disclosed methods and devices including, but not limited to, phosphoric acid/sodium hydroxide, glutamic acid/lysine, formic acid/dimethylamine, commercial carrier ampholytes mixtures (e.g., Servalyt pH 4-9 (Serva, Heildelberg, Germany), Beckman pH 3-10 (Beckman Instruments, Fullerton, Calif., USA), Ampholine 3.5-9.5 and Pharmalyte 3-10 (both from General Electrics Healthcare, Orsay, France)), and the like. Carrier ampholyte mixtures are mixtures of small molecules (about 300-1,000 Da) containing multiple aliphatic amino and carboxylate groups that have closely spaced pI values and good buffering capacity. In the presence of an applied electric field, carrier ampholytes partition into smooth pH gradients that increase linearly from the anode to the cathode.

Any of a variety of pI standards may be used in the disclosed methods and devices for calculating the isoelectric point for separated analyte peaks provided that they can be visualized using an appropriate imaging technique. In general, there are two types of pI markers used in CIEF applications: protein pI markers and synthetic small molecule pI markers. Protein pI markers are based on specific proteins that have commonly accepted pI values. They generally require the adoption of stringent storage conditions, may exhibit poor stability, and thus may yield multiple peaks in CIEF. Synthetic small molecules (preferably non-peptide molecules so that they may be used in enzyme separations) are generally more stable during storage and will focus to a single peak in CIEF. There are a variety of protein pI markers or synthetic small molecule pI markers available, e.g., the small molecule pI markers available from Advanced Electrophoresis Solutions, Ltd. (Cambridge, Ontario, Canada).

Capillary zone electrophoresis (CZE): In some instances, the separation technique may comprise capillary zone electrophoresis, a method for separation of charged analytes in solution in an applied electric field. The net velocity of charged analyte molecules is influenced both by the electroosmotic flow (EOF), $\mu$EOF, exhibited by the separation system and the electrophoretic mobility, $\mu$EP, for the individual analyte (dependent on the molecule's size, shape, and charge), such that analyte molecules exhibiting different size, shape, or charge exhibit differential migration velocities and separate into bands. In contrast to other capillary electrophoresis methods, CZE uses "simple" buffer solutions for separation.

Capillary gel electrophoresis (CGE): In some instances, the separation technique may comprise capillary gel electrophoresis, a method for separation and analysis of macromolecules (e.g., DNA, RNA and proteins) and their fragments based on their size and charge. The method comprises use of a gel-filled separation channel, where the gel acts as an anti-convective and/or sieving medium during electrophoretic movement of charged analyte molecules in an applied electric field. The gel functions to suppress thermal convection caused by application of the electric field, and also acts as a sieving medium that retards the passage of molecules, thereby resulting in a differential migration velocity for molecules of different size or charge.

Capillary isotachophoresis (CITP): In some instances, the separation technique may comprise capillary isotachophoresis, a method for separation of charged analytes that uses a discontinuous system of two electrolytes (known as the leading electrolyte and the terminating electrolyte) within a capillary or fluid channel of suitable dimensions. The leading electrolyte contains ions with the highest electrophoretic mobility, while the terminating electrolyte contains ion with the lowest electrophoretic mobility. The analyte mixture (i.e., the sample) to be separated is sandwiched between these two electrolytes, and application of an electric field results in partitioning of the charged analyte molecules within the capillary or fluid channel into closely contiguous zones in order of decreasing electrophoretic mobility. The zones move with constant velocity in the applied electric field such that a detector, e.g., a conductivity detector, photodetector, or imaging device, may be utilized record their passage along the separation channel. Unlike capillary zone electrophoresis, simultaneous determination or detection of anionic and cationic analytes is not feasible in a single analysis performed using capillary isotachophoresis.

Capillary electrokinetic chromatography (CEC): In some instances, the separation technique may comprise capillary electrokinetic chromatography, a method for separation of analyte mixtures based on a combination of liquid chromatographic and electrophoretic separation methods. CEC offers both the efficiency of capillary electrophoresis (CE) and the selectivity and sample capacity of packed capillary high performance liquid chromatography (HPLC). Because the capillaries used in CEC are packed with HPLC packing materials, the wide variety of analyte selectivities available in HPLC are also available in CEC. The high surface area of these packing materials enables CEC capillaries to accommodate relatively large amounts of sample, making detection of the subsequently eluted analytes a somewhat simpler task than it is in capillary zone electrophoresis (CZE).

Micellar electrokinetic chromatography (MEKC): In some instances, the separation technique may comprise capillary electrokinetic chromatography, a method for separation of analyte mixtures based on differential partitioning between surfactant micelles (a pseudo-stationary phase) and a surrounding aqueous buffer solution (a mobile phase). The basic set-up and detection methods used for MEKC are the same as those used in CZE. The difference is that the buffer solution contains a surfactant at a concentration that is greater than the critical micelle concentration (CMC), such that surfactant monomers are in equilibrium with micelles. MEKC is typically performed in open capillaries or fluid channels using alkaline conditions to generate a strong electroosmotic flow. Sodium dodecyl sulfate (SDS) is one example of a commonly used surfactant in MEKC applications. The anionic character of the sulfate groups of SDS cause the surfactant and micelles to have electrophoretic mobility that is counter to the direction of the strong electroosmotic flow. As a result, the surfactant monomers and micelles migrate quite slowly, though their net movement is still in the direction of the electoosmotic flow, i.e., toward the cathode. During MEKC separations, analytes distribute themselves between the hydrophobic interior of the micelle and hydrophilic buffer solution. Hydrophilic analytes that are insoluble in the micelle interior migrate at the electroosmotic flow velocity, uo, and will be detected at the retention time of the buffer, tM. Hydrophobic analytes that solubilize completely within the micelles migrate at the micelle velocity, uc, and elute at the final elution time, tc.

Flow counterbalanced capillary electrophoresis (FCCE): In some instances, the separation technique may comprise flow counterbalanced capillary electrophoresis, a method for increasing the efficiency and resolving power of capillary electrophoresis that utilizes a pressure-induced counter-flow to actively retard, halt, or reverse the electrokinetic migration of an analyte through a capillary. By retarding, halting, or moving the analytes back and forth across a detection window, the analytes of interest are effectively confined to the separation channel for much longer periods of time than under normal separation conditions, thereby increasing both the efficiency and the resolving power of the separation.

Chromatography: In some instances, the separation technique may comprise a chromatographic technique in which the analyte mixture in the sample fluid (the mobile phase) is passed through a column or channel-packing material (the stationary phase) which differentially retains the various constituents of the mixture, thereby causing them to travel at different speeds and separate. In some instances, a subsequent step of elution or mobilization may be required to displace analytes that have a high binding affinity for the stationary phase. Examples of chromatographic techniques the may be incorporated into the disclosed methods include, but are not limited to, ion exchange chromatography, size-exclusion chromatography, and reverse-phase chromatography.

Imaging of separation channels: In most instances, the disclosed methods (and devices and systems configured to perform said methods) may comprise imaging of all or a portion of at least one separation channel to monitor a separation and/or mobilization reaction while it is performed. In some instances, separation and/or mobilization reactions may be imaged using any of a variety of imaging techniques known to those of skill in the art. Examples include, but are not limited to, ultraviolet (UV) light absorbance, visible light absorbance, fluorescence (e.g., native fluorescence or fluorescence resulting from having labeled one or more analytes with fluorophores), Fourier transform infrared spectroscopy, Fourier transform near infrared spectroscopy, Raman spectroscopy, optical spectroscopy, and the like. In some instances, all or a portion of a separation (or enrichment) channel, a junction or connecting channel that connects an end of the separation channel and a downstream analytical instrument or an electrospray orifice or tip, the electrospray orifice or tip itself, or any combination thereof may be imaged. In some instances the separation (or enrichment) channel may be the lumen of a capillary. In some instances, the separation (or enrichment) channel may be a fluid channel within a microfluidic device.

The wavelength range(s) used for detection of separated analyte bands will typically depend on the choice of imaging technique and the material(s) out of which the device or portion thereof are fabricated. For example, in the case that UV light absorbance is used for imaging all or a portion of the separation channel or other part of the microfluidic device, detection at about 220 nm (due to a native absorbance of peptide bonds) and/or at about 280 nm (due to a native absorbance of aromatic amino acid residues) may allow one to visualize protein bands during separation and/or mobilization provided that at least a portion of the device, e.g., the separation channel or a portion thereof, is transparent to light at these wavelengths. In some instances, the analytes to be separated and characterized via ESI-MS may be labeled prior to separation with, e.g., a fluorophore, chemiluminescent tag, or other suitable label, such that they may be imaged using fluorescence imaging or other suitable imaging techniques. In some instances, e.g., wherein the analytes comprise proteins produced by a commercial manufacturing process, the proteins may be genetically-engineered to incorporate a green fluorescence protein (GFP) domain or variant thereof, so that they may be imaged using fluorescence. Care must be taken when labeling proteins or other analyte molecules to ensure that the label itself doesn't interfere with or perturb the analyte property on which the chosen separation technique is based.

In some instances, imaging (or data derived therefrom) may be used to trigger a mobilization step or other transfer of separated analyte fractions or portions thereof from one separation channel to another, for from a separation channel to another channel that is in fluid communication with an outlet end of a separation channel. For example, in some instances the disclosed methods may comprise injecting an analyte into a microfluidic device containing a first separation channel and a second separation channel. The first separation channel can contain a medium configured to bind an analyte from the analyte mixture. Accordingly, when the analyte mixture is injected into the microfluidic device at least a fraction of the analyte mixture can be bound to the matrix and/or impeded from flowing through the first separation channel. For example, injecting the analyte into the microfluidic device can effect a chromatographic separation in the first separation channel. An eluent can be injected into the microfluidic device such that at least a fraction of the analyte is mobilized from the media. The first separation channel can be imaged while the analyte is mobilized. Imaging the first separation can include whole column (e.g., whole channel) imaging and/or imaging a portion of the channel. An electric field can be applied to the second separation channel when the imaging detects that the fraction is disposed at an intersection of the first separation channel and the second separation channel such that the fraction is mobilized into the second separation channel. For example, in some instances, the first separation channel and the second separation channel can form a T-junction. The imaging can detect when a portion of the fraction (e.g., a portion of interest) is at the junction. Applying the electric field can mobilize the portion of the fraction (and, optionally, not other portions of the fraction that are not located at the junction) into the second separation channel for a second stage of separation. In some instances, at least a portion of the fraction may be expelled from the microfluidic device.

Mobilization of separated analyte species: In some instances of the disclosed methods, e.g., those comprising a chromatographic separation technique such as reverse-phase chromatography, elution of the analyte species retained on the stationary phase (e.g., by changing a buffer that flows through the separation channel) may be referred to as a "mobilization" step. In most instances, the force used to drive the separation reaction (e.g., pressure for reverse-phase chromatography, or an electric field for electrokinetic separation or isoelectric focusing reactions) may be turned off during the mobilization step. In some instances, the force used to drive the separation reaction may be left on during the mobilization step. In some instances of the disclosed methods, e.g., those comprising an isoelectric focusing step, the separated analyte bands may be mobilized (e.g., using hydrodynamic pressure and/or a chemical mobilization technique) such that the separated analyte bands migrate towards an end of the separation channel that is connected to another fluid channel (which may be a second separation channel) or that interfaces with a downstream analytical device, e.g., an electrospray ionization interface with a mass spectrometer. In some embodiments, e.g., in those instances where capillary gel electrophoresis, capillary zone electrophoresis, isotachophoresis, capillary electrokinetic chromatography, micellar electrokinetic chromatography, flow counterbalanced capillary electrophoresis, or any other separation technique that separates components of an analyte mixture by differential velocity is employed, the separation step may be viewed as the mobilization step.

In some instances, mobilization of the analyte bands may be implemented by applying hydrodynamic pressure to one end of the separation channel. In some instances, mobilization of the analyte bands may be implemented by orienting the separation channel in a vertical position so that gravity may be employed. In some instances, mobilization of the analyte bands may be implemented using EOF-assisted mobilization. In some instances, mobilization of the analyte bands may be implemented using chemical mobilization, e.g., by introducing a mobilization electrolyte into the separation channel that shifts the local pH in a pH gradient used for isoelectric focusing. In some instances, any combination of these mobilization techniques may be employed.

In one preferred instance, the mobilization step for isoelectrically-focused analyte bands comprises chemical mobilization. Compared with pressure-based mobilization, chemical mobilization has the advantage of exhibiting minimal band broadening by overcoming the hydrodynamic parabolic flow profile induced by the use of pressure. Chemical mobilization may be implemented by introducing an electrolyte (i.e., a "mobilization electrolyte") into the separation channel to alter the local pH and/or net charge on separated analyte bands (or zwitterionic buffer components) such that they (or the zwitterionic buffer components and associated hydration shells) migrate in an applied electric field. In some instances, the polarity of the applied electric field used to mobilize separated analyte bands may be such that analytes migrate towards an anode that is in electrical communication with the outlet or distal end of the separation channel (anodic mobilization). In some instances, the polarity of the applied electric field used to mobilize separated analyte bands may be such that analytes migrate towards a cathode that is in electrical communication with the outlet or distal end of the separation channel (cathodic mobilization). Mobilization electrolytes comprise either anions or cations that compete with hydroxyls (cathodic mobilization) or hydronium ions (anodic mobilization) for introduction into the separation channel or capillary. Examples of bases that may be used as catholytes for anodic mobilization include, but are not limited to, ammonium, diethylamine, dimethyl amine, piperidine, etc. Examples of acids that may be used as anolytes in cathodic mobilization include, but are not limited to, acetic acid, formic acid, and carbonic acid, etc. In some instances, an anode may be held at ground, and a negative voltage is applied to the cathode. In some instances, a cathode may be held at ground, and a positive voltage is applied to the anode. In some instances, a non-zero negative voltage may be applied to the cathode, and a non-zero positive voltage may be applied to the anode.

In some instances, mobilization of separated analyte bands may be initiated at a user-specified time point that triggers switchable electrodes (e.g., a cathode in electrical communication with the distal end of the separation channel, and a cathode in electrical communication with a proximal end of a mobilization channel (a fluid channel that intersects the separation channel near the outlet or distal end of the separation channel)) between on and off states to control the electrophoretic introduction of a mobilization buffer or electrolyte into a separation channel.

In some instances, a user-specified time for independently triggering a transition of one, two, or three or more switchable electrodes between on and off states may range from about 30 seconds, to about 30 minutes for any of the mobilization schemes. In some instances, the user-specified time may be at least 30 second, at least 1 minute, at least 2 minutes, at least 3 minutes, at least 4 minutes, at least 5 minutes, at least 10 minutes, at least 15 minutes, at least 20 minutes, at least 25 minutes, or at least 30 minutes. In some instances, the user-specified time may be at most 30 minutes, at most 25 minutes, at most 20 minutes, at most 15 minutes, at most 10 minutes, at most 5 minutes, at most 4 minutes, at most 3 minutes, at most 2 minutes, at most 1 minutes, or at most 30 seconds. Any of the lower and upper values described in this paragraph may be combined to form a range included within the present disclosure, for example, in some instances the user-specified time may range from about 2 minutes to about 25 minutes. Those of skill in the art will recognize that the user-specified time may have any value within this range, e.g., about 8.5 minutes.

In some instances, the electric field used to affect mobilization in any of the mobilization scenarios disclosed herein (or to perform electrokinetic separation or isoelectric focusing reactions in those instances where such separation techniques are performed) may range from about 0 V/cm to about 1,000 V/cm. In some instances, the electric field strength may be at least 0 V/cm, at least 20 V/cm, at least 40 V/cm, at least 60 V/cm, at least 80 V/cm, at least 100 V/cm, at least 150 V/cm, at least 200 V/cm, at least 250 V/cm, at least 300 V/cm, at least 350 V/cm, at least 400 V/cm, at least 450 V/cm, at least 500 V/cm, at least 600 V/cm, at least 700 V/cm, at least 800 V/cm, at least 900 V/cm, or at least 1,000 V/cm. In some instances, the electric field strength may be at most 1,000 V/cm, at most 900 V/cm, at most 800 V/cm, at most 700 V/cm, at most 600 V/cm, at most 500 V/cm, at most 450 V/cm, at most 400 V/cm, at most 350 V/cm, at most 300 V/cm, at most 250 V/cm, at most 200 V/cm, at most 150 V/cm, at most 100 V/cm, at most 80 V/cm, at most 60 V/cm, at most 40 V/cm, at most 20 V/cm, or at most 0 V/cm. Any of the lower and upper values described in this paragraph may be combined to form a range included within the present disclosure, for example, in some instances the electric field strength time may range from about 40 V/cm to about 650 V/cm. Those of skill in the art will recognize that the electric field strength may have any value within this range, e.g., about 575 V/cm.

In some instances, mobilization of separated analyte bands may be initiated based on data derived from monitoring the current (or conductivity) of the separation channel where, for example, in the case of isoelectric focusing the current passing through the separation channel may reach a minimum value. In some instances, the detection of a minimum current value, or a current value that remains below a specified threshold for a specified period of time, may be used to determine if an isoelectric focusing reaction has reached completion and may thus be used to trigger the initiation of a chemical mobilization step.

In some instances, the minimum current value or threshold current value may range from about 0 µA to about 100 µA. In some instances, the minimum current value or threshold current value may be at least 0 µA, at least 1 µA, at least 2 µA, at least 3 µA, at least 4 µA, at least 5 µA, at least 10 µA, at least 20 µA, at least 30 µA, at least 40 µA, at least 50 µA, at least 60 µA, at least 70 µA, at least 80 µA, at least 90 µA, or at least 100 µA. In some instances, the minimum current value or threshold current value may be at most 100 µA, at most 90 µA, at most 80 µA, at most 70 µA, at most 60 µA, at most 50 µA, at most 40 µA, at most 30 µA, at most 20 µA, at most 10 µA, at most 5 µA, at most 4 µA, at most 3 µA, at most 2 µA, at most 1 µA, or at most 0 µA. Any of the lower and upper values described in this paragraph may be combined to form a range included within the present disclosure, for example, in some instances the minimum current value or threshold current value may range from about 10 µA to about 90 µA. Those of skill in the art will recognize that the minimum current value or threshold current value may have any value within this range, e.g., about 16 µA.

In some instances, the specified period of time may be at least 5 seconds, at least 10 seconds, at least 15 seconds, at least 20 seconds, at least 25 seconds, at least 30 seconds, at least 35 seconds, at least 40 seconds, at least 45 seconds, at least 50 seconds, at least 55 seconds, or at least 60 seconds.

In some instances, mobilization of separated analyte bands may be initiated based on data derived from images (e.g., by performing automated image processing) of the separation channel as a separation step is performed. The image-derived data may be used to monitor the presence or absence of one or more analyte peaks, the positions of one or more analyte peaks, the widths of one or more analyte peaks, the velocities of one or more analyte peaks, separation resolution, a rate of change or lack thereof in the presence, position, width, or velocity of one or more analyte peaks, or any combination thereof, and may be used to determine whether a separation reaction is complete and/or to trigger the initiation of a mobilization steps. In some cases, completion of a separation step may be determined by monitoring the rate of change of a separation performance parameter (e.g., peak position or peak width) over a period of time (e.g., over a period of 10 to 60 seconds).

In one preferred aspect of the disclosed methods, a chemical mobilization step may be initiated within a microfluidic device designed to integrate CIEF with ESI-MS by changing an electric field within the device to electrophorese a mobilization electrolyte into the separation channel. In some instances, the initiation of the mobilization step may be triggered based on data derived from images of all or a portion of the separation channel. In some instances, the change in electric field may be implemented by connecting or disconnecting one or more electrodes attached to one or more power supplies, wherein the one or more electrodes are positioned in reagent wells on the device or integrated with fluid channels of the device. In some instances, the connecting or disconnecting of one or more electrodes may be controlled using a computer-implemented method and programmable switches, such that the timing and duration of the mobilization step may be coordinated with the separation step, the electrospray ionization step, and/or mass spectrometry data collection. In some instances, changing an electric field within the device may be used to electrophoretically or electro-osmotically flow a mobilization buffer into a separation channel comprising a stationary phase such that retained analytes are released from the stationary phase.

In some instances, three or more electrodes may be connected to the device. For example, a first electrode may be coupled electrically to a proximal end of the separation channel. Similarly, a second electrode may then be coupled to the distal end of the separation channel, and a third electrode may be coupled with a mobilization channel that intersects with the separation channel, e.g., at a distal end of the separation channel, and that connects to or comprises a reservoir containing mobilization buffers. Upon completion of the separation step, as determined by image-based methods, the electric coupling of the second or third electrodes with their respective channels may be switchable between "on" and "off" states. In one such an example, the second electrode that forms the anode or cathode of the separation circuit may switch to an "off" mode, and the third electrode, which may be off during the separation, may switch to an "on" mode, to initiate introduction of mobilization buffer into the channel (e.g., via electrophoresis). In some instances, "on" and "off" states may comprise complete connection or disconnection of the electrical coupling between an electrode and a fluid channel respectively. In some instances, "on" and "off" states may comprise clamping the current passing through a specified electrode to non-zero or zero microamperes respectively.

In some instances, triggering or initiation of a mobilization step may comprise detecting no change or a change of less than a specified threshold for one or more image-derived separation parameters as described above. For example, in some instances a change of less than 20%, 15%, 10%, or 5% in one or more image-derived parameters (e.g., peak position, peak width, peak velocity, etc.) may be used to trigger the mobilization step.

In some instances, triggering or initiation of a mobilization step may comprise detecting no change or a rate of change of less than a specified threshold for one or more image-derived separation parameters as described above. For example, in some instances a change of less than 20%, 15%, 10%, or 5% in one or more image-derived parameters (e.g., peak position, peak width, peak velocity, etc.) over a time period of at least 10 seconds, 15 seconds, 20 seconds, 25 seconds, 30 seconds, 35 seconds, 40 seconds, 45 seconds, 50 seconds, 55 seconds, or 60 seconds (or any combination of these percentage changes and time periods) may be used to trigger the mobilization step.

Separation times and separation resolution: In general, the separation time required to achieve complete separation will vary depending on the specific separation technique and operational parameters (e.g., separation channel length, microfluidic device design, buffer compositions, applied voltages, etc.) utilized. In some instances, the separation time may range from about 0.1 minutes to about 30 minutes. In some instances, the separation time may be at least 0.1 minutes, at least 0.5 minutes, at least 1 minute, at least 5 minutes, at least 10 minutes, at least 15 minutes, at least 20 minutes, at least 25 minutes, or at least 30 minutes. In some instances, the separation time may be at most 30 minutes, at most 25 minutes, at most 20 minutes, at most 15 minutes, at most 10 minutes, at most 5 minutes, at most 1 minute, at most 0.5 minutes, or at most 0.1 minutes. Any of the lower and upper values described in this paragraph may be combined to form a range included within the present disclosure, for example, in some instances the separation time may range from about 1 minute to about 20 minutes. Those of skill in the art will recognize that the separation time may have any value within this range, e.g., about 11.2 minutes.

Similarly, the separation efficiency and resolution achieved using the disclosed methods and devices may vary depending on the specific separation technique and operational parameters (e.g., separation channel length, microfluidic device design, buffer compositions, applied voltages, etc.) utilized, as well as whether one or two dimensions of separation are utilized. In some instances, for example when performing isoelectric focusing, the use of switchable electrodes to trigger electrophoretic introduction of a mobilization electrolyte into the separation channel may result in improved separation resolution. For example, in some instances, the separation resolution of IEF performed using the disclosed methods and devices may provide for a resolution of analyte bands differing in pI ranging from about 0.1 to about 0.0001 pH units. In some instances, the IEF separation resolution may allow for resolution of analyte bands differing in pI by less than 0.1, 0.05, 0.01, 0.005, 0.001, 0.0005, or 0.0001 pH units.

In some instances, the peak capacity may range from about 10 to about 20,000. In some instances, the peak capacity may be at least 10, at least 100, at least 200, at least 300, at least 400, at least 500, at least 600, at least 700, at least 800, at least 900, at least 1,000, at least 2,000, at least 3,000, at least 4,000, at least 5,000, at least 10,000, at least 15,000, or at least 20,000. In some instances, the peak capacity may be at most 20,000, at most 15,000, at most 10,000, a most 5,000, at most 4,000, at most 3,000, at most 2,000, at most 1,000, at most 900, at most 800, at most 700, at most 600, at most 500, at most 400, at most 300, at most 200, at most 100, or at most 10. Any of the lower and upper values described in this paragraph may be combined to form a range included within the present disclosure, for example, in some instances the peak capacity may range from about 400 to about 2,000. Those of skill in the art will recognize that the peak capacity may have any value within this range, e.g., about 285.

In some instances, the use of chemical mobilization in the disclosed devices that are configured to introduce the mobilization electrolyte to the separation channel electrophoretically, the separation resolution achieved during isoelectric focusing has been observed to further improve during the mobilization step. In some instances, the improvement in separation resolution during the mobilization step may range from about 10% to about 100% relative to the separation resolution achieved during the isoelectric focusing step. In some instances, the improvement achieved using chemical mobilization in the disclosed devices configured to introduce the mobilization electrolyte electrophoretically may be at least 10%, at least 20%, at least 30%, at least 40%, at least 50%, at least 60%, at least 70%, at least 80%, at least 90%, or at least 100%. In some instances, the improvement achieved using chemical mobilization in the disclosed devices configured to introduce the mobilization electrolyte electrophoretically may be at most 100%, at most 90%, at most 80%, at most 70%, at most 60%, at most 50%, at most 40%, at most 30%, at most 20%, at most 10%, at most 0%. Any of the lower and upper values described in this paragraph may be combined to form a range included within the present disclosure, for example, in some instances the improvement in separation resolution may range from about 20% to about 60%. Those of skill in the art will recognize that the improvement in separation resolution may have any value within this range, e.g., about 23%.

Expulsion of analytes for downstream analysis: In some embodiments, substantially all of the enriched analyte fractions from the final enrichment step are expelled in a continuous stream. In some embodiments, a portion of the analyte mixture (e.g., a fraction of interest) will be expelled from a capillary or microfluidic device via an outlet configured to interface with an analytical instrument, e.g., a spectrophotometer, a spectrofluorimeter, a mass spectrometer, a flow cytometer, or another instrument configured to perform qualitative, semi-quantitative, or quantitative characterization of the separated analyte fractions. In some instances, other portions of the analyte mixture (e.g., containing fractions other than the fraction of interest) may be expelled via a waste channel.

In some instances, the expulsion one or more analyte fractions is performed using pressure, electric fields, ionization, or a combination of these.

In some instances, the expulsion is performed using electrospray ionization (ESI) into, for example, a mass spectrometer. In some instances a sheath liquid is used as an electrolyte for an electrophoretic separation. In some instances, a nebulizing gas is provided to reduce the analyte fraction to a fine spray. In some instances, other ionization methods may be used, such as inductive coupled laser ionization, fast atom bombardment, soft laser desorption, atmospheric pressure chemical ionization, secondary ion mass spectrometry, spark ionization, thermal ionization, and the like.

In some instances, the enriched fractions will be deposited on a surface for further analysis by matrix-assisted laser desorption/ionization, surface enhanced laser desorption/ionization, immunoblot, and the like.

In some instances, the disclosed methods (as well as the disclosed devices and systems configured to perform said methods) relate to visualizing an analyte in an electrophoretic separation before and during the expulsion of enriched fractions. In some instances, they relate to visualizing an analyte during an enrichment step. In some instances, they relate to visualizing an analyte in a channel between enrichment zones. In some instances, as noted above, the visualization of an analyte can be performed via optical detection, such as ultraviolet light absorbance, visible light absorbance, fluorescence, Fourier transform infrared spectroscopy, Fourier transform near infrared spectroscopy, Raman spectroscopy, optical spectroscopy, and the like.

Devices for Sample Analysis

Some instances described herein relate to devices that can enable the analysis of analyte mixtures, in that they contain one or more enrichment zones and an orifice to expel enriched analyte fractions. In some instances, these devices include at least one layer which is not transmissive to light of a specific wavelength, and at least one layer which is transmissive to that specific wavelength. One or more portions of the layer which is not transmissive to light can define the one or more enrichment zones, such that the enrichment zones serve as optical slits.

In some instances, an analyte mixture can be loaded into a device through a tube or capillary connecting the device to an autosampler. In some embodiments, an analyte mixture can be loaded directly into a reservoir on the device.

In some instances, an orifice through which at least a portion of a sample can be expelled from a device is countersunk and/or shielded from air flow. In some instances, this orifice is not electrically conductive. As used herein, countersunk should be understood to mean that a portion of a substrate defines a recess containing the orifice, irrespective of the geometry of the sides or chamfers of the recess. Similarly stated, countersunk should be understood to include counterbores, conical and/or frustoconical countersinks, hemispherical bores, and the like.

Some instances described herein relate to an apparatus, such as a microfluidic device that includes a substrate constructed of an opaque material (e.g., soda lime glass, which is opaque to ultraviolet light). The substrate can define a microfluidic separation channel. Similarly stated, the microfluidic separation channel can be etched or otherwise formed within the substrate. The microfluidic separation channel can have a depth equal to the thickness of the substrate. Similarly stated, the microfluidic separation channel can be etched the full depth of the substrate (e.g., from the top all the way through to the bottom). In this way, the microfluidic separation channel can define an optical slit through the substrate. A transparent layer (e.g., a top layer) can be disposed on a top surface of the substrate, for example, sealing the top surface of the substrate. A transparent layer (e.g., a bottom layer) can also be disposed on a bottom surface of the substrate, such that both the top and the bottom of the microfluidic separation channel are sealed. In some instances, only a portion of the top layer and/or the bottom layer may be transparent. For example, the top layer and/or the bottom layer can define a transparent window in an otherwise opaque material; the window can provide optical access to, for example, the microfluidic separation channel.

Some instances described herein relate to an apparatus, such as a microfluidic device that includes a substrate. The substrate can define one or more enrichment zones or channels. For example, the substrate can define a first enrichment zone containing a media configured to bind to an analyte. Such a first enrichment zone can be suitable to separate an analyte mixture chromatographically. The apparatus can further include two electrodes electrically coupled to opposite end portions of a second enrichment zone. Such a second enrichment zone can be suitable to separate an analyte mixture electrophoretically. The second enrichment zone can intersect the first enrichment zone such that after a fraction of an analyte is separated, concentrated, and/or enriched in the first enrichment zone, it can be further separated, concentrated, and/or enriched in the second enrichment zone. The device can also include a recessed orifice. The orifice can be an outlet of the second enrichment channel and can be disposed on a countersunk or otherwise recessed surface of the substrate. The apparatus can be configured to expel a portion of an analyte mixture from the orifice via ESI. The recess can provide a stable environment for formation of a Taylor cone associated with ESI and/or can be configured to accept an inlet port of a mass spectrometer.

Figure 1B:
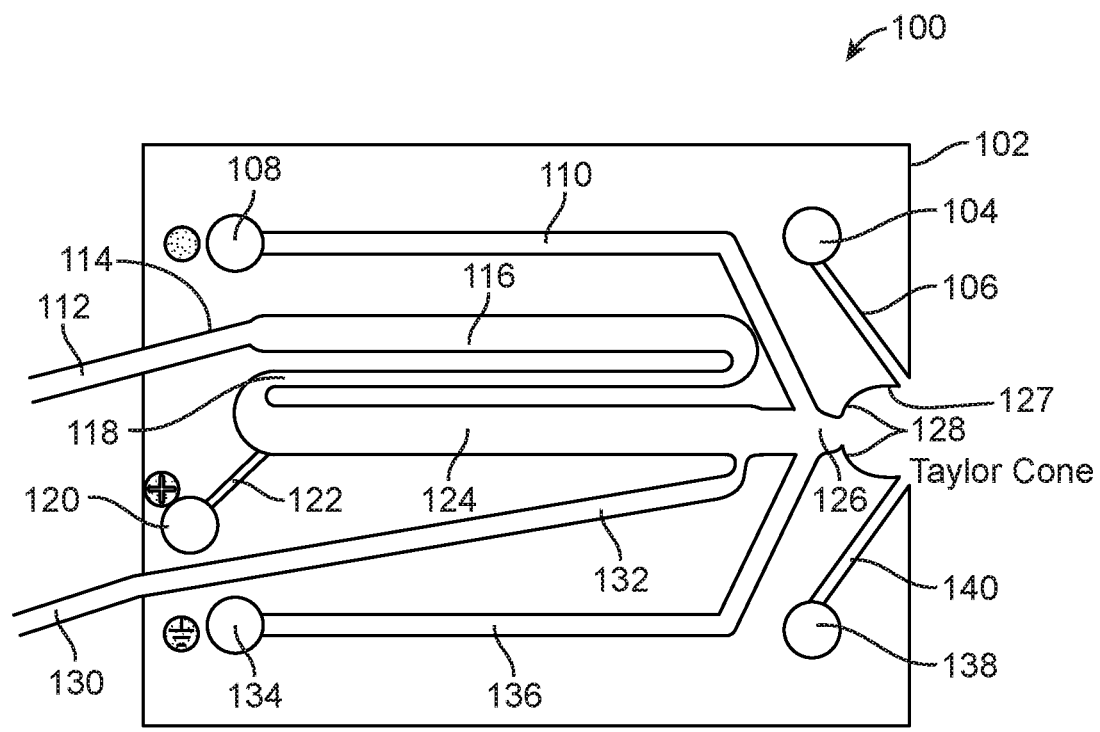

FIGS. 1A and 1B provide schematic illustrations of a device for two-dimensional separation and ESI of an automatically loaded sample, according to an embodiment. A microfluidic network, 100, is defined by a substrate 102. The substrate is manufactured out of material which is compatible with the enrichment steps being performed. For example, chemical compatibility, pH stability, temperature, transparency at various wavelengths of light, mechanical strength, and the like are considered in connection with selection of material.

Substrate 102 may be manufactured out of glass, quartz, fused silica, plastic, polycarbonate, polyfluorotetraethylene (PFTE), polydimethylsiloxane (PDMS), silicon, polyfluorinated polyethylene, polymethacrylate, cyclic olefin copolymer, cyclic olefin polymer, polyether ether ketone and/or any other suitable material. Mixtures of materials can be utilized if different properties are desired in different layers of a planar substrate and/or any other suitable material. Mixtures of materials can be utilized if different properties are desired in different layers of a planar substrate.

Channels 106, 110, 114, 116, 118, 124 122, 126,132, 136 and 140 form the microfluidic network 100 and are fabricated into substrate 102. Similarly stated, the substrate 102 defines channels 106, 110, 114, 116, 118, 124 122, 126,132, 136 and/or 140.

Channels may be fabricated in the substrate through any channel fabrication method such as, for example, photolithographic etching, molding, machining, additive (3D) printing, and the like.

Analyte mixtures and external reagents can be loaded through tube/conduit 112, and excess reagent/waste can be removed through tube/conduit 130.

Tubes 112 and 130 can be manufactured out of any material compatible with the assay being performed, including, for example, fused silica, fused silica capillary tubes, silicone tubing, and/or PFTE tubing.

Channels 116 and 124 can be used to separate and/or enrich an analyte and/or a portion (e.g., a fraction) of an analyte. Channels 116 and/or 124 can be used to perform chromatographic separations (e.g., reversed-phase, immunoprecipitation, ion exchange, size exclusion, ligand affinity, dye affinity, hydrophobic interaction chromatography, hydrophilic interaction chromatography, pH gradient ion exchange, affinity, capillary electrokinetic chromatography, micellar electrokinetic chromatography, high performance liquid chromatography (HPLC), amino acid analysis-HPLC, ultra performance liquid chromatography, peptide mapping HPLC, field flow fractionation—multi angle light scattering) or electrophoretic separations (e.g., isoelectric focusing, capillary gel electrophoresis, capillary zone electrophoresis, isotachophoresis, capillary electrokinetic chromatography, micellar electrokinetic chromatography, flow counterbalanced capillary electrophoresis, electric field gradient focusing, dynamic field gradient focusing). For example, channel 116 can be derivatized or packed with material to perform a first enrichment step.

The material disposed into channel 116 and/or 124 can be selected to capture analytes based on, for example, hydrophobicity (reversed-phase), immunoaffinity (immunoprecipitation), affinity (efficacy), size (size exclusion chromatography), charge (ion exchange) or by other forms of liquid chromatography.

Many different methods can be used to dispose the enrichment material within channels 116 and/or 124. The walls can be directly derivatized with, for example, covalently bound or adsorbed molecules, or beads, glass particles, sol-gel or the like can be derivatized and loaded into these channels.

After sample is loaded into channel 116 wash solution and then elution reagent can be introduced through tube 112 and channel 114.

The elution process will depend on the enrichment method performed in channel 116. A suitable eluent can be selected to elute a fraction of the bound analyte. Some enrichment options may not require an elution step (e.g., size exclusion chromatography, electrophoretic separations, etc.)

The eluent or flow-through would then flow through channel 118 into channel 124. Channel 124 could be used to perform either a chromatographic or electrophoretic enrichment step.

Electrophoretic separations can be performed in channel 124 by using a power supply to apply an electric field between reservoir 108 and reservoir 120. Similarly stated, the device 100 can include electrodes in electrical contact with reservoir 108 and/or reservoir 120. The electrical ground of the power supply can be connected to the electrical ground of a mass spectrometer to provide continuity in the electric field from channel 124 to the mass spectrometer.

Any capillary electrophoresis (CE) electrophoretic method can be performed in channel 124—IEF, isotachophoresis (ITP), capillary gel electrophoresis (CGE), capillary zone electrophoresis (CZE), and the like. Alternately, non-electrophoretic enrichment methods can be performed in the channel 124.

In the case of IEF or ITP, concentrated purified sample bands would be mobilized by pressure, chemical or electrical means towards confluence 126. Sheath solution from reservoirs 108 and 134 could serve as sheath and catholyte.

The sheath/catholyte can be any basic solution compatible with the electrophoretic separation and mass spectrometry (MeOH/N$_4$OH/H$_2$O for example). Anolyte can be any acidic solution (e.g., phosphoric acid 10 mM).

Alternately, the electric field could be reversed and catholyte (NaOH) could be loaded in reservoir 120, and anolyte could be used as the sheath solution in reservoirs 108 and 134.

The confluence 126 is where the enriched analyte fraction mixes with the sheath solution. As the analyte fractions in channel 124 are mobilized, solution will be pushed through confluence 126 out to orifice 128.

In the case of chemical mobilization, the sheath liquid can provide the acidic or basic mobilizer (such as ammonium, acetic acid, formic acid, etc.) which can disrupt an IEF pH gradient, thereby mobilizing the sample bands. By loading this mobilizer solution in reservoir 108, the mobilizer would be electrophoretically driven into channel 124. By applying pressure to reservoir 108, the mobilizer solution can flow through confluence 126 and out orifice 128. The mobilized sample bands would migrate out of channel 124 electrophoretically, then enter the pressure driven flow of the mobilizer solution in confluence 126.

The orifice 128 can be disposed within a recess defined by surface 127 of substrate 102. For example, surface 127 can be a countersunk ESI surface. For example, as shown in FIG. 1, the enriched analyte solution, being electrically grounded through well 108, can form a Taylor cone emanating from orifice 128, which is disposed entirely within a recess defined by surface 127. The orifice 128 and/or surface 127 can be oriented toward a mass spectrometer inlet, which can have a voltage potential difference relative to well 108. As spray breaks off from the cone structure toward the mass spectrometer, it can be flanked by nebulizing gas provided through nebulizing gas wells 104 and 138 via channels 106 and 140 before it leaves the substrate 102. The nebulizing gas can be any inert or non-reactive gas (e.g., Argon, Nitrogen, and the like).

Additionally, using a sheath liquid and/or nebulizing gas can allow for the use of an ion depleting step as the last "on-device" step. The sheath liquid allows for replenishment of ion potential lost during an IEF charge assay concentrating step prior to ESI, and nebulization provides the sample in a fine mist for the off line analysis.

By generating the Taylor cone on surface 127, the cone is created in a stable pocket or recess and is protected from disturbing air currents. Additionally, the conical geometry surrounding the countersunk orifice has a naturally expanding contact surface that will accommodate a wider range of Taylor cone radial cross sections, allowing for a wider range of flow rates into the mass spectrometer.

Orifice 128 can be positioned in proximity to an inlet port of a mass spectrometer. In some instances, the surface 127 can be configured such that an inlet port of a mass spectrometer can be disposed within a recess defined by the surface 127.

FIG. 2 a schematic exploded view of a device 212 having three layers, according to an embodiment. FIG. 2A shows a top layer 202 of device 212, according to an embodiment. FIG. 2B shows a middle layer 206 of device 212, according to an embodiment. FIG. 2C shows a bottom layer 210 of device 212, according to an embodiment. FIG. 2D shows the device 212 as assembled, according to an embodiment. Each of the three layers 202, 206, 210 may be made of any material compatible with the assays the device 212 is intended to perform.

In some embodiments, layer 202 will be fabricated from a material which is transparent to a specific wavelength, or wavelength range, of light. As used herein, "transparent" should be understood to mean that a substantial majority light having a specific wavelength or range of wavelengths is transmitted through the material. A transparent material can also be understood to mean the material has sufficient transmittance to allow the amount of light on one side of the material to be quantified by a detector on the other side. In some embodiments, a wavelength range of interest will include the middle ultraviolet range (e.g., 200 nm-300 nm), and materials such as, for example, glass, quartz, fused silica and UV-transparent plastics such as polycarbonates, polyfluorinated polyethylene, polymethacrylate, cyclic olefin polymer, cyclic olefin copolymer, and other UV-transparent materials can be used as transparent materials. In some embodiments, the light spectrum of interest will be expanded beyond the visible spectrum (e.g., 200-900 nm).

Through-holes, 204, are fabricated in layer 202 to allow pressure and electrical interface to a channel network in a lower layer (e.g., layer 208) from outside the device.

Figure 2A:
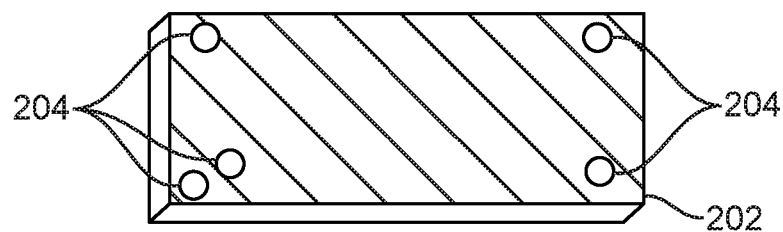
FIGS. 2A-D provide a schematic exploded view of a microfluidic device comprising three layers, according to one aspect of this disclosure.
Figure 2B:
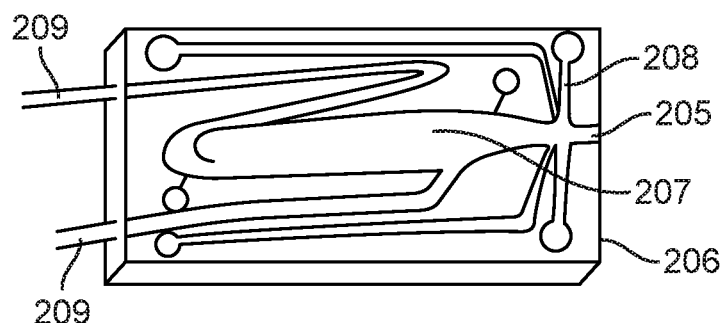

FIG. 2B shows the internal middle layer 206 of device 212 containing the channel network 208. The channel network is designed to interface with the through-holes fabricated in the top layer 202. The channel network 208 contains inlet and outlet tubes/conduits 209, and orifice 205 for expelling enriched analyte fractions, and a viewable enrichment zone 207. Enrichment zone 207 is fabricated so its depth is the full thickness of the layer 206. In other embodiments, zone 207 can be less than the full thickness of layer 206.

In some embodiments, layer 206 will be fabricated from a material which is opaque and/or not transparent to a specific wavelength, or wavelength range, of light. As used herein, "opaque" should be understood to mean that a substantial majority light having a specific wavelength or range of wavelengths is not transmitted through the material (e.g., reflected, absorbed, and/or scattered by the material). A material that is not transparent can also be understood to mean the material has insufficient transmittance to allow the amount of light on one side of the material to be quantified by a detector on the other side, and will effectively block this light except in the regions where the zone in the channel network is as deep as the full thickness of layer 206.

Figure 2C:
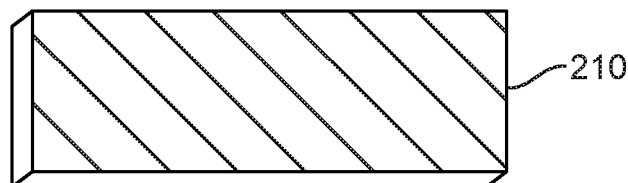

FIG. 2C shows a bottom layer 210 of device 212. Bottom layer 210 can be, for example, a solid substrate. In some embodiments, bottom layer 210 can be fabricated from a material with the same transmittance as layer 202.

Figure 2D:
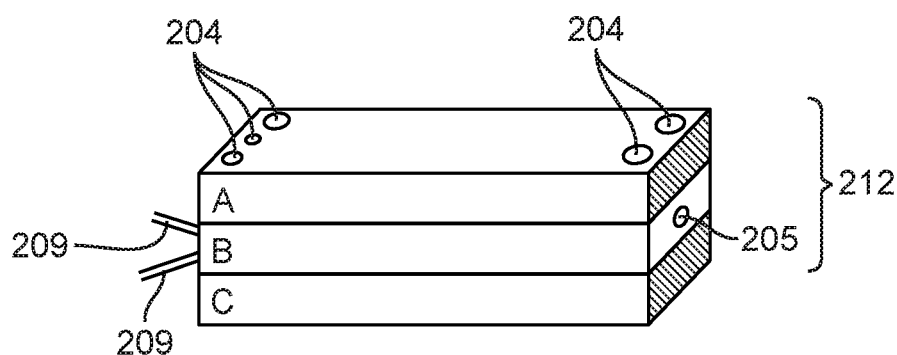

FIG. 2D shows the device 212 including top layer 202, the middle layer 206, and the bottom layer 210, as assembled, according to an embodiment. Inlet and outlet tubes 209, reservoirs 204 and orifice 205 can still be accessed after the device 210 is assembled. In some embodiments, the entire top layer 202 and/or the entire bottom layer 210 can be transparent. In other embodiments, a portion of the top layer 202 and/or a portion of the bottom layer 210 can be opaque with another portion of the top layer 202 and/or the bottom layer 210 being transparent. For example, the top layer 210 and/or the bottom layer 210 can define an optical window that aligns with at least a portion of the enrichment zone 207 when the device 212 is assembled.

Figure 3A:
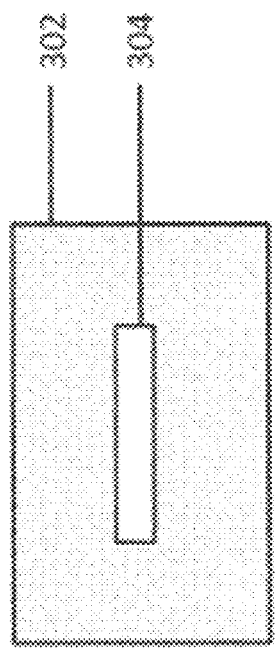
FIGS. 3A-B provide a schematic illustration of a transparent window integrated with a separation channel within a microfluidic device (FIG. 3A), and of a light path through the microfluidic device (FIG. 3B), according to one aspect of this disclosure.
Figure 3B:
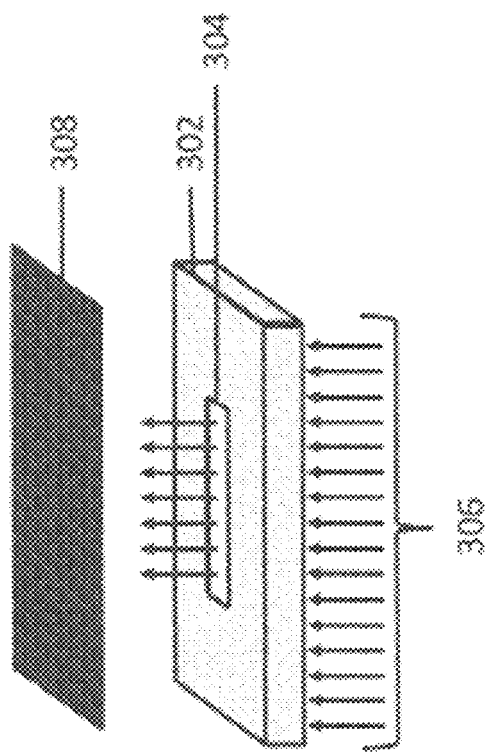

FIG. 3 is a schematic of a light path through a microfluidic device 302, according to an embodiment. FIG. 3A shows a top view of the microfluidic device 302. FIG. 3B shows the microfluidic device 302 positioned between a light source 306 and a detector 308. The detector 308 is positioned to measure light passing through the device 302. While not illustrated in FIG. 3, the microfluidic device 302 can have a similar channel structure as described in FIGS. 1 and 2, but the channel structure is not shown for ease of reference. In some embodiments, a portion of top surface of the microfluidic device 302 is opaque and completely or substantially obscures light projected from the light source 306 from reaching the detector 308. The portion of the opaque top surface substantially prevents the transmission of light through the device at those portions where detection of sample properties is not desired. For example, the microfluidic device 302 in some embodiments is not opaque (e.g., allows some light to pass through) over one or more channel region(s) 304, as the channel 304 transverses the entire thickness of a non-transparent layer.

In some embodiments, this transparent channel region(s) 304, can be an enrichment zone, where optical detection can be used to detect analyte, monitor the progress of the enrichment and/or monitor enriched analyte fraction(s) as they are expelled from the device. In some embodiments, changes in the amount of light passing through transparent channel 304 will be used to measure the absorbance of the analyte fractions while they are in this channel. Thus, in some embodiments, channel region(s) 304 define an optical slit, such that the light source 306 positioned on one side of the microfluidic device 302 effectively illuminates the detector 308 only through the transparent channel region(s) 304. In this way, stray light (e.g., light that does not pass thorough the transparent channel regions(s) and/or a sample) can be effectively blocked from the detector 308, which can reduce noise and improve the ability of the detector 308 to observe sample within the transparent channel region(s) 304. In some embodiments, the transparent channel regions(s) 304 will be between two enrichment zones, and can be used to detect analyte fractions as they are eluted from the upstream enrichment zone.

Figure 6:
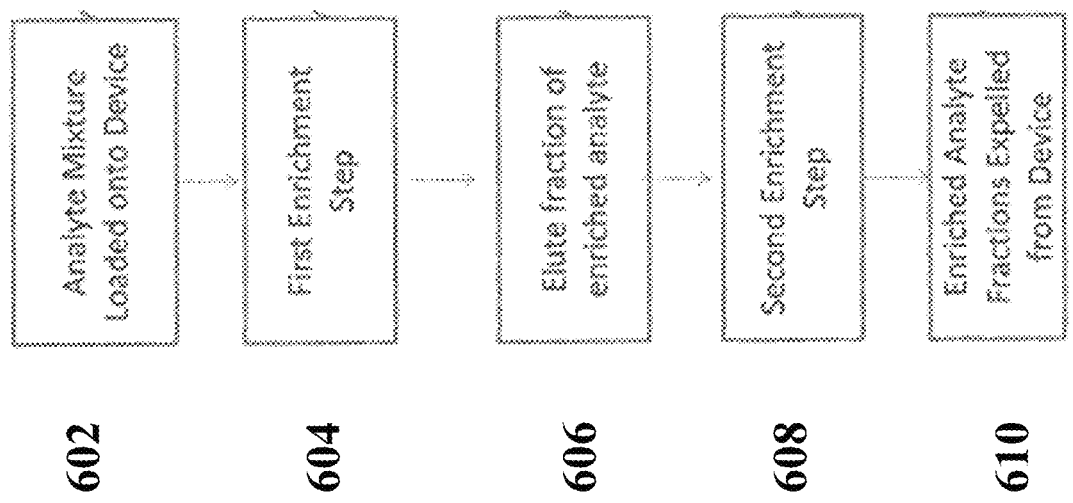
FIG. 6 provides a flowchart of an exemplary method for analyte characterization.

FIG. 6 illustrates a method of analyte mixture enrichment according to one aspect of the present disclosure. The method includes loading and/or introducing an analyte mixture onto a microfluidic device, at 602. The microfluidic device can be similar to the microfluidic devices described above with reference to FIGS. 1-3. In some instances, the analyte mixture can be, for example, glycans, carbohydrates, DNA, RNA, intact proteins, digested proteins, peptides, metabolites, vaccines, viruses and small molecules. In some instances, the analyte mixture can be a mixture of proteins, such as a lysate of cultured cells, cell-based therapeutics, or tumor or other tissue derived cells, recombinant proteins, including biologic pharmaceuticals, blood derived cells, perfusion or a protein mixture from any other source. The analyte mixture may be loaded directly onto the device, or may be loaded onto an autosampler for serial analysis of multiple mixtures.

The microfluidic device can include a first separation channel and/or enrichment zone. In some embodiments, the first separation channel and/or enrichment zone can be configured for chromatographic separation. For example, the first separation channel and/or enrichment zone can contain a media configured to bind an analyte from the analyte mixture and/or otherwise effect a chromatographic separation. At 604, a first enrichment can be performed; for example, a chromatographic separation can be performed in the first separation channel and/or enrichment zone. In some embodiments, such as embodiments in which the analyte mixture is a protein mixture, the first enrichment, at 604, can simplify the protein mixture. The first enrichment, at 604, can be based on any discernable quality of the analyte.

This enriched analyte fraction is then eluted, at 606. For example, an eluent can be injected into the microfluidic device to mobilize the enriched analyte fraction from media disposed within the first separation channel and/or enrichment zone. In some embodiments, the enrichment and/or mobilization of the enriched analyte fraction can be imaged. For example, as discussed above, the first separation channel and/or enrichment zone can define an optical slit. Light can be projected onto the microfluidic device and a detector can detect light passing through the first separation channel and/or enrichment zone. The sample, or a portion thereof can be detected via absorbance and/or fluorescence imaging techniques.

The microfluidic device can include a second separation channel and/or enrichment zone. In some embodiments, the second separation channel and/or enrichment zone can be configured for electrophoretic separation. At 608, a second enrichment can be performed, for example, on the eluate. For example, an electric field and/or electric potential can be applied across the second separation channel and/or enrichment zone.

In some instances, the second enrichment can be initiated, at 608, when a fraction of the analyte mixture is disposed at an intersection of the first separation channel and/or enrichment zone and the second separation channel and/or enrichment zone. For example, the first separation channel and/or enrichment zone can be monitored (e.g., imaged) and a an electric potential, and/or electric filed can be applied when a fraction of interest reaches the intersection.

In some instances, the second enrichment, at 608, can provide fractions enriched based on charge characteristics (charge isoforms). Such enrichments can include, for example, gel isoelectric focusing, isoelectric focusing with mobilization, isoelectric focusing with whole column imaging, ion exchange chromatography, pH gradient exchange chromatography, isotachophoresis, capillary zone electrophoresis, capillary gel electrophoresis or other enrichment techniques that are, for example, charge-based.

Although the first enrichment, at 604, has been described as a chromatographic enrichment and the second enrichment, at 608, has been described as electrophoretic, it should be understood the any suitable enrichment can be performed in any suitable sequence. For example, the first enrichment, at 604, and the second enrichment, at 608, can both be chromatographic or both be electrophoretic. As another example, the first enrichment, at 604, can be electrophoretic, and the second enrichment, at 608, can be chromatographic.

In some instances, one or more enrichments can provide fractions enriched based on hydrophobic changes, such as oxidation. Such enrichments can include, for example, reversed-phase chromatography, hydrophobic interaction chromatography, hydrophilic interaction chromatography, or other enrichment techniques that are, for example, hydrophobicity-based.

In some instances, one or more enrichments can will provide fractions enriched based on post-translational modifications, glycoforms including galactosylation, fucosylation, sialylation, mannose derivatives and other glycosylations, as well as glycation, oxidation, reduction, phosphorylation, sulphanation, disulfide bond formation, deamidiation, acylation, pegylation, cleavage, antibody-drug conjugation (ADC), protein-drug conjugation, C-terminal lysine processing, other naturally and non-naturally occurring post-translational modifications and other chemical and structural modifications introduced after translation of the protein, and the like. Such enrichments can include, for example, binding assays and the like.

In some instances, one or more enrichments can provide fractions enriched based on hydrophobic changes, such as oxidation. Such enrichments can include, for example, reversed-phase chromatography, hydrophobic interaction chromatography, hydrophilic interaction chromatography, or other enrichment techniques that are hydrophobicity-based.

In some instances, one or more enrichments can provide fractions enriched based on primary amino acid sequence, such as caused by mutation, amino acid substitution during manufacture and the like. Such enrichments can include, for example, separating by charge isoforms, hydrophobic changes, or other enrichment techniques that can distinguish between primary amino acid sequence differences.

In some instances, one or more enrichments can provide fractions enriched based on efficacy. Such enrichments can include, for example, bioassays, enzyme inhibition assays, enzyme activation assays, competition assays, fluorescence polarization assays, scintillation proximity assays, or other enrichment techniques that are efficacy-based and the like.

In some instances, one or more enrichments can provide fractions enriched based on affinity. Such enrichments can include, for example, solution phase binding to target, binding to bead based targets, surface bound target, immunoprecipitation, protein A binding, protein G binding and the like.

In some instances, one or more enrichments can provide fractions enriched based on mass or size. Such enrichments can include, for example, poly acrylamide gel electrophoresis, capillary gel electrophoresis, size exclusion chromatography, gel permeation chromatography, or other enrichment techniques that are mass-based.

In some instances, the analyte mixture will go through more than two enrichment before being expelled from the device.

At 610, an enriched analyte fraction can be expelled from the device. In some embodiments, the enriched analyte fraction can be expelled via electrospray ionization. Enriching the analyte fraction, at 608, can concentrate the analyte fractions before they are expelled from the microfluidic device.

In some instances the analyte fractions are expelled, at 610, using an ionization technique, such as electrospray ionization, atmospheric pressure chemical ionization, and the like.

In some instances, the analyte fractions are expelled, at 610, using electrokinetic or hydrodynamic forces.

In some instances, the enriched protein fractions are expelled, at 610, from the device in a manner coupled to a mass spectrometer.

Mass of an analyte expelled from the microfluidic device (e.g., a biologic or biosimilar) can be measured, for example, through time-of-flight mass spectrometry, quadrupole mass spectrometry, Ion trap or orbitrap mass spectrometry, distance-of-flight mass spectrometry, Fourier transform ion cyclotron resonance, resonance mass measurement, and nanomechanical mass spectrometry.

In some instances pI markers are used to map pI ranges in the visualized IEF channel (e.g., the first separation channel and/or enrichment zone and/or the second separation channel and/or enrichment zone). In some embodiments, pI markers or ampholytes can be used to determine the pI of the analyte by their presence in downstream mass spectrometry data.

In some instances, IEF can be monitored during the mobilization and ESI. In this way, mass spectrometry data can be correlated to peaks in the IEF, which can maintain and/or improve peak resolution.

In some instances, the analyte mixture and/or a portion thereof can be mobilized within the microfluidic device using pressure source. In some instances, mobilization is done with hydrostatic pressure. In some instances, mobilization is chemical mobilization. In some instances, mobilization is electrokinetic mobilization.

Figure 8:
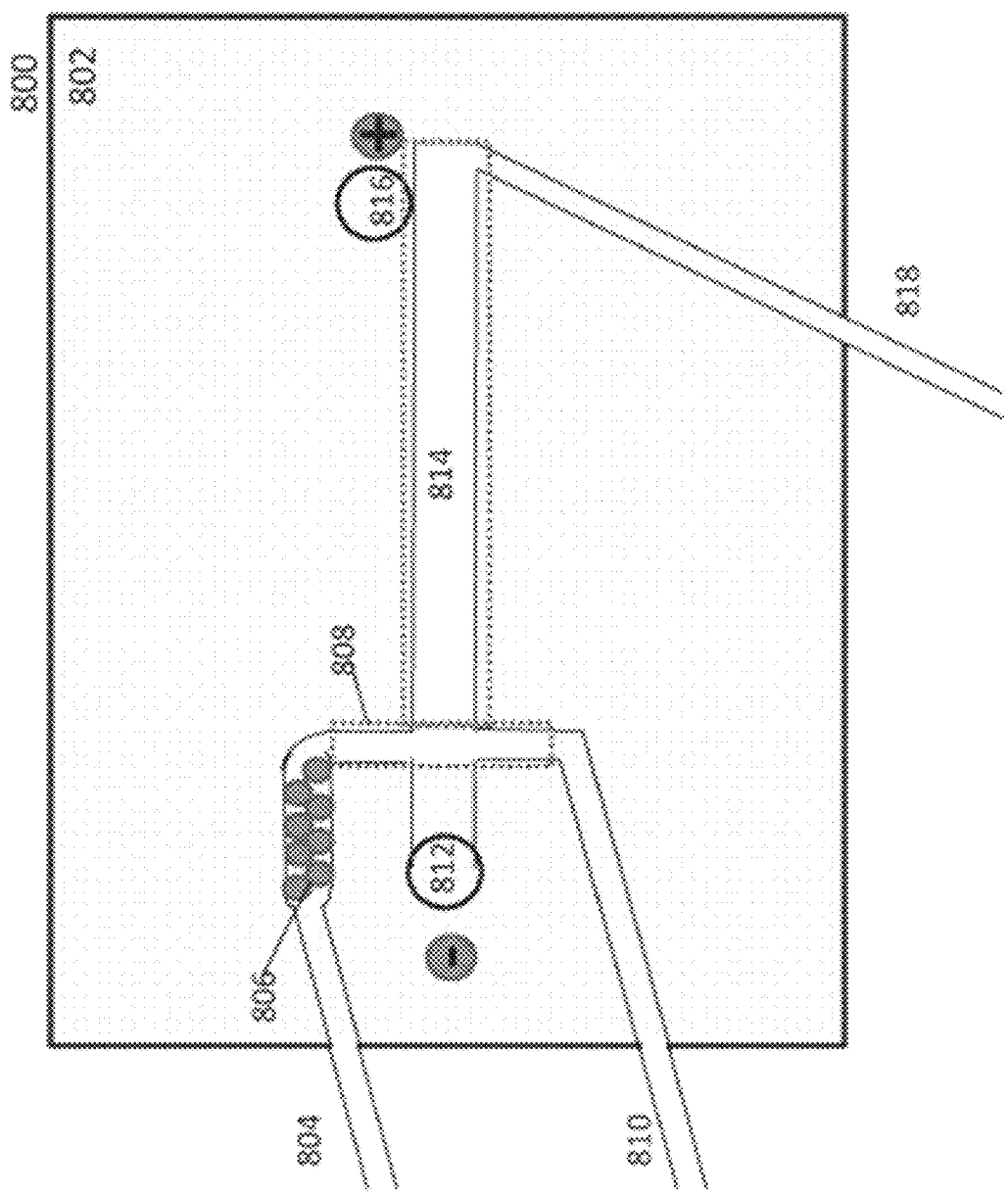
FIG. 8 provides a schematic illustration of a microfluidic device, according to one aspect of this disclosure.

FIG. 8 is a schematic of a microfluidic device, according to one aspect of the present disclosure. A microfluidic network, 800, is disposed in and/or defined by a substrate, 802. The substrate is manufactured out of material which is compatible with the enrichment steps being performed. For example, chemical compatibility, pH stability, temperature, transparency at various wavelengths of light, mechanical strength, and the like may be of concern when selecting the material Substrate 802 may be manufactured out of glass, quartz, fused silica, plastic, polycarbonate, PFTE, PDMS, silicon, polyfluorinated polyethylene, polymethacrylate, cyclic olefin copolymer, cyclic olefin polymer, polyether ether ketone and/or any other suitable material. Mixtures of materials can be utilized if different properties are desired in different layers of a planar substrate.

Channels 806, 808, 810, 811, 817, 814, form a channel network and are fabricated into (e.g., defined by) substrate 802.

Channels may be fabricated in the substrate through any channel fabrication method such as photolithographic etching, molding, machining, additive (3D) printing, and the like.

Analyte mixtures and external reagents can be loaded through tube 804, and excess reagent/waste can be removed through tube 810 and 818.

Tubes 804 and 810 818 can be manufactured out of any material compatible with the assay being performed, including fused silica, fused silica capillary tubes, silicone tubing, PFTE tubing, and the like.

Channels 806 and 814 can be designated as separation/enrichment zones. Either of channel 806 and/or 814 can be used to perform chromatographic separations (reversed phase, immunoprecipitation, ion exchange, size exclusion, ligand affinity, dye affinity, hydrophobic interaction, affinity, capillary electrokinetic chromatography, micellar electrokinetic chromatography and/or the like) or electrophoretic separations (isoelectric focusing, capillary gel electrophoresis, capillary zone electrophoresis, isotachophoresis, capillary electrokinetic chromatography, micellar electrokinetic chromatography, flow counterbalanced capillary electrophoresis, electric field gradient focusing, dynamic field gradient focusing, and/or the like). For example, channel 806 can be derivatized or packed with material to perform a first enrichment step, represented by darker circles in channel 806.

The material disposed into channel 806 can be selected to capture analytes based on hydrophobicity (reversed phase), affinity (efficacy), size (size exclusion chromatography), charge (ion exchange), immunoaffinity (immunoprecipitation), protein-protein interaction, DNA-protein interaction, aptamer-base capture, small molecule-base capture or by other forms of liquid chromatography and the like.

Many different methods can be used to dispose the enrichment material within channel 806 and/or 814. The walls can be directly derivatized with covalently bound or adsorbed molecules, or beads, glass particles, sol-gel or the like can be derivatized and loaded into these channels, or channels can be packed with a sieving material such as— linear polymer solutions such as linear polyacrylamide (LPA), polyvinylpyrrolidone (PVP), polyethylene oxide (PEO), dextran, and the like, cross-linked polymer solutions such as polyacrylamide and the like, matrices for liquid chromatography, or other materials.

Chemically-reactive solutions may be added depending on the particular assay performed. In some cases, derivatization of material may occur after it is loaded into channel 806 (or channel 814), by adding molecules which will adsorb or covalently bond to the loaded material, or can chemically cross link reactive elements to the material. For example, material coated with an antibody-binding molecule such as protein A, protein G, epoxy or the like, could be disposed into channel 806. Subsequent rinsing with an antibody solution would leave the material coated with antibody and able to participate in immunoaffinity capture. In some cases, the antibody may be mixed with a target analyte or lysate so that the antibody can bind its target in free solution before being coated onto the material.

After enrichment materials are loaded onto device, sample is loaded via tube 804 into channel 806. Subsequently, wash solutions and elution reagents can be introduced through tube 804 to channel 806.

In some cases, detection reagents will be added to bind to captured material. Numerous labeling reagents are available that can covalently attach detection moieties such as fluorophores, chromophores or other detection molecules to the target proteins at terminal ends of the polypeptide, and by attachment to amino acid side chains such as lysine, cysteine and other amino acid moieties. Covalently-bound detection moieties allow for the protein to be detected through fluorescence excitation, chromophoric assay, or other indirect means. In some cases, the target protein can remain unlabeled and detected through native absorbance at 220 nm, 280 nm or any other wavelength at which the protein will absorb light, or native fluorescence. In some cases, the protein will be detected using non-covalently bound fluorogenic, chromogenic, fluorescent or chromophoric labels, such as SYPRO® ruby, Coomassie blue and the like.

In some cases, detection reagents will be added directly to channel 814 to aid detection.

The elution process will depend on the enrichment method performed in channel 806. It will be selected to elute at least a fraction of the bound analyte. In some cases, this can be accomplished with a combination of heat and sodium dodecyl sulfate (SDS), or other detergents, glycine, urea, or any other method which will induce the release of the captured analyte. Some enrichment options may not require a direct elution step (e.g. size exclusion chromatography). In some cases, elution will be followed by denaturation.

The eluent would then flow through channel 808 into the next separation/enrichment zone, channel 814. Channel 814 could be used to perform either a chromatographic or electrophoretic enrichment step.

Electrophoretic separations can be performed in channel 814 by using a power supply to apply an electric field between reservoir 812 and reservoir 816. When eluate from channel 806 passes through the intersection of channels 808 and 814, the electric field can be enabled, loading analyte into channel 814. In some case, the analyte will be negatively charged, such as in the standard gel electrophoresis mode where protein analyte is saturated with a negatively charged detergent like SDS. However, the polarity of channel 814 can easily be reversed to accommodate systems where for example, a protein analyte is saturated with a positively charged detergent such as cetyl trimethylammonium bromide (CTAB) or the like. In other cases, a protein analyte may be coated with a neutral detergent, or no detergent—such as in native gel electrophoresis. In this case, polarity will be selected based on the anticipated charge of the protein target in the buffer system selected, so that the protein analyte will migrate into channel 814.

Any CE electrophoretic method can be performed in channel 814—IEF, ITP, CGE, CZE, and the like. Alternately, non-electrophoretic enrichment methods can be performed in the channel.

Analyte in channel 814 can be viewed by whole column imaging, partial column imaging, and/or by single point detection.

In some cases, the enrichment material in channels 806, 814 or both may be removed and replenished with fresh material so that the device can be used on another analyte sample. In some cases, a channel design such as FIG. 8 may be repeated multiple times on a device, so that more than one analyte sample may be analyzed in parallel.

Microfluidic device design and fabrication: In some instances of the disclosed methods, devices, and systems, the separation of analytes from a mixture and, optionally, their subsequent analysis using ESI-MS or other analytical instrument may be performed using a microfluidic device designed to integrate one or more sample preparation steps (e.g., filtration, pre-concentration, or extraction steps, and the like) and/or separation steps (e.g., as outlined above) with an electrospray ionization step.

In some instances, the disclosed microfluidic device may comprise one or more sample or reagent ports (also referred to as inlet ports, sample wells, or reagent wells), one or more waste ports (also referred to as outlet ports), one or more fluid channels connecting said inlet an outlet ports with each other or with intermediate fluid channels (e.g., separation channels), or any combination thereof. In some embodiments, the disclosed microfluidic devices may further comprise one or more reaction chambers or mixing chambers, one or more microfabricated valves, one or more microfabricated pumps, one or more vent structures, one or more membranes (e.g., filtration membranes), one or more microcolumn structures (e.g., fluid channels or modified fluid channels that have been packed with a chromatographic separation medium), or any combination thereof.

Any of a variety of fluid actuation mechanisms known to those of skill in the art may used to control fluid flow of samples and reagents through the device. Examples of suitable fluid actuation mechanisms for use in the disclosed methods, devices, and systems include, but are not limited to, application of positive or negative pressure to one or more inlet ports or outlet ports, gravitational or centrifugal forces, electrokinetic forces, electrowetting forces, or any combination thereof. In some embodiments, positive or negative pressure may be applied directly, e.g., through the use of mechanical actuators or pistons that are coupled to the inlet and/or outlet ports to actuate flow of the sample or reagents through the fluidic channels. In some embodiments, the mechanical actuators or pistons may exert force on a flexible membrane or septum that is used to seal the inlet and/or outlet ports. In some embodiments, positive or negative pressure may be applied indirectly, e.g., through the use of a pressurized gas lines or vacuum lines connected with one or more inlet and/or outlet ports. In some embodiment, pumps, e.g., programmable syringe pumps, HPLC pumps, or peristaltic pumps, connected with one or more inlet and/or outlet ports may be used to drive fluid flow. In some embodiments, electrokinetic forces and/or electrowetting forces may be applied through the use of electric field and control of surface properties within the device. Electric fields may be applied by means of electrodes inserted into one or more inlet and/or outlet ports, or by means of electrodes integrated into one or more fluid channels within the device. The electrodes may be connected with one or more DC or AC power supplies for controlling voltages and/or currents within the device.

In general, the inlet ports, outlet ports, fluid channels, or other components of the disclosed microfluidic devices, including the main body of the device, may be fabricated using any of a variety of materials, including, but not limited to glass, fused-silica, silicon, polycarbonate, polymethylmethacrylate, cyclic olefin copolymer (COC) or cyclic olefin polymer (COP), polydimethylsiloxane (PDMS), or other elastomeric materials. Suitable fabrication techniques will generally depend on the choice of material, and vice versa. Examples include, but are not limited to, CNC machining, photolithography and chemical etching, laser photoablation, injection molding, hot embossing, die cutting, 3D printing, and the like. In some embodiments, the microfluidic device may comprise a layered structure in which, for example, a fluidics layer comprising fluid channels is sandwiched between an upper layer and/or a lower layer to seal the channels. The upper layer and/or lower layer may comprise openings that align with fluid channels in the fluidics layer to create inlet and/or outlet ports, etc. Two or more device layers may be clamped together to form a device which may be disassembled, or may be permanently bonded. Suitable bonding techniques will generally depend on the choice of materials used to fabricate the layers. Examples include, but are not limited to, anodic bonding, thermal bonding, laser welding, or the use of UV-curable adhesives.

In some embodiments, all or a portion of the inlet ports, outlet ports, or fluid channels within the microfluidic device may comprise a surface coating used to modify the electroosmotic flow properties (e.g., HPC or PVA coatings) and/or hydrophobicity/hydrophilicity properties (e.g., polyethylene glycol (PEG) coatings) of the inlet port, outlet port, or fluid channel walls.

The inlet and/or outlet ports of the disclosed devices can be fabricated in a variety of shapes and sizes. Appropriate inlet and/or outlet port geometries include, but are not limited to, cylindrical, elliptical, cubic, conical, hemispherical, rectangular, or polyhedral (e.g., three dimensional geometries comprised of several planar faces, for example, rectangular cuboid, hexagonal columns, octagonal columns, inverted triangular pyramids, inverted square pyramids, inverted pentagonal pyramids, inverted hexagonal pyramids, or inverted truncated pyramids), or any combination thereof.

Inlet and/or outlet port dimensions may be characterized in terms of an average diameter and depth. As used herein, the average diameter of the inlet or outlet port refers to the largest circle that can be inscribed within the planar cross-section of the inlet and/or outlet port geometry. In some embodiments of the present disclosure, the average diameter of the inlet and/or outlet ports may range from about 0.5 mm to about 10 mm. In some embodiments, the average diameter of the inlet and/or outlet ports may be at least 0.5 mm, at least 1 mm, at least 2 mm, at least 4 mm, at least 8 mm, or at least 10 mm. In some embodiments, the average diameter may be at most 10 mm, at most 8 mm, at most 6 mm, at most 4 mm, at most 2 mm, at most 1 mm, or at most 0.5 mm. Any of the lower and upper values described in this paragraph may be combined to form a range included within the present disclosure, for example, in some embodiments the average diameter may range from about 2 mm to about 8 mm. Those of skill in the art will recognize that the average diameter of the inlet and/or outlet ports have any value within this range, e.g., about 5.5 mm.

In some embodiments, the depth of the inlet and/or outlet ports (e.g., the sample or reagent wells) may range from about 5 µm to about 500 µm. In some embodiments, the depth may be at least 5 µm, at least 10 µm, at least 25 µm, at least 50 µm, at least 75 µm, at least 100 µm, at least 200 µm, at least 300 µm, at least 400 µm, or at least 500 µm. In some embodiments, the depth may be at most 500 µm, at most 400 µm, at most 300 µm, at most 200 µm, at most 100 µm, at most 50 µm, at most 25 µm, at most 10 µm, or at most 5 µm. Any of the lower and upper values described in this paragraph may be combined to form a range included within the present disclosure, for example, in some embodiments the depth of the inlet and/or outlet ports may range from about 50 µm to about 200 µm. Those of skill in the art will recognize that the depth may have any value within this range, e.g., about 130 µm.

In some embodiments, the fluid channels of the disclosed devices may have any of a variety of cross-sectional geometries, such as square, rectangular, circular, and the like. In general the cross-sectional geometry of the fluid channels will be dependent on the fabrication technique used to create them, and vice versa. In some embodiments, a cross-sectional dimension of the fluid channels (e.g., the height, the width, or an average diameter for a fluid channel of non-rectangular cross-section, where the average diameter is defined as the diameter of the largest circle that can be inscribed within the cross-sectional geometry of the fluid channel) may range from about 5 µm to about 500 µm. In some embodiments, a dimension the fluid channel may be at least 5 µm, at least 10 µm, at least 25 µm, at least 50 µm, at least 75 µm, at least 100 µm, at least 200 µm, at least 300 µm, at least 400 µm, or at least 500 µm. In some embodiments, a dimension of the fluid channel may be at most 500 µm, at most 400 µm, at most 300 µm, at most 200 µm, at most 100 µm, at most 50 µm, at most 25 µm, at most 10 µm, or at most 5 µm. Any of the lower and upper values described in this paragraph may be combined to form a range included within the present disclosure, for example, in some embodiments a dimension of the fluid channel may range from about 75 µm to about 300 µm. Those of skill in the art will recognize that the dimension may have any value within this range, e.g., about 95 µm. In some embodiments, a depth of the fluid channel may be equal to that for the inlet and/or outlet ports of the device.

In some instances of the disclosed devices, an intersection between a mobilization channel and a separation channel may comprise an angle ranging from about 10 degrees to about 90 degrees. In some instances, the angle between the mobilization channel and the separation channel may be at least 10 degrees, at least 20 degrees, at least 30 degrees, at least 40 degrees, at least 50 degrees, at least 60 degrees, at least 70 degrees, at least 80 degrees, or at least 90 degrees.

Systems for Sample Analysis

The sample analysis systems of the present disclosure may comprise: (i) one or more autoloaders or other fluid handling instruments for injecting samples into the disclosed devices, (ii) one or more of the disclosed devices for performing separation of analytes, (iii) one or more fluid pumps (or fluidics controllers), (iv) one or more high voltage power supplies (or electric field/current controllers), (v) one or more imaging systems (or "modules", "units", etc.), (vi) one or more mass spectrometers or other analytical instruments, and (vii) one or more processors, controllers, or computers, or any combination thereof. In some instances, the one or more processors, controllers, or computers may be configured to run software comprising encoded instructions for automating the sample loading process, controlling fluid flow velocities within the device by means of applied pressure and/or electric fields (including for performing separation and/or mobilization reactions), controlling the image acquisition process, performing semi-automated or fully-automated image processing, controlling the synchronization between the operation of the microfluidic device and a mass spectrometer or other downstream analytical instrument, controlling data acquisition by a mass spectrometer or other downstream analytical instrument, and date processing, storage, and display, or any combination thereof.

Imaging hardware: Any of a variety of imaging systems or system components may be utilized for the purpose of implementing the disclosed methods, devices, and systems. Examples include, but are not limited to, one or more light sources (e.g., light emitting diodes (LEDs), diode lasers, fiber lasers, gas lasers, halogen lamps, arc lamps, etc.), condenser lenses, objective lenses, mirrors, filters, beam splitters, prisms, image sensors (e.g., CCD image sensors or cameras, CMOS image sensors or cameras), and the like, or any combination thereof. Depending on the imaging mode utilized, the light source and image sensor may be positioned on opposite sides of the microfluidic device, e.g., so that absorbance-based images may be acquired. In some instances, the light source and image sensor may be positioned on the same side of the microfluidic device, e.g., so that epifluorescence images may be acquired.

Images may be acquired continuously during the separation and/or mobilization steps, or may be acquired at random or specified time intervals. In some instances, a series of one or more images are acquired continuously or at random or specified time intervals. In some instances, a series of short exposure images (e.g., 10-20 images) are acquired on a fast (e.g., millisecond timescale) and are then averaged to provide a "single image" having improved signal-to-noise ratio. In some instances, a "single image" is acquired every 1 second, 5 seconds, 10 seconds, 20 seconds, 30 seconds, or at longer time intervals. In some instances, In some instances, the series of one or more images may comprise video images.

Image processing software: In some instances, as noted above, the system may comprise processors, controllers, or computers configured to run image processing software for detecting the presence of analyte peaks, determining the positions of pI markers or separated analyte bands, for determining peak shapes, or changes in any of these parameters over time. Any of a variety of image processing algorithms known to those of skill in the art may be utilized for image pre-processing or image processing in implementing the disclosed methods and systems. Examples include, but are not limited to, Canny edge detection methods, Canny-Deriche edge detection methods, first-order gradient edge detection methods (e.g., the Sobel operator), second order differential edge detection methods, phase congruency (phase coherence) edge detection methods, other image segmentation algorithms (e.g., intensity thresholding, intensity clustering methods, intensity histogram-based methods, etc.), feature and pattern recognition algorithms (e.g., the generalized Hough transform for detecting arbitrary shapes, the circular Hough transform, etc.), and mathematical analysis algorithms (e.g., Fourier transform, fast Fourier transform, wavelet analysis, auto-correlation, etc.), or any combination thereof.

Processors and computer systems: One or more processors or computers may be employed to implement the methods disclosed herein. The one or more processors may comprise a hardware processor such as a central processing unit (CPU), a graphic processing unit (GPU), a general-purpose processing unit, or computing platform. The one or more processors may be comprised of any of a variety of suitable integrated circuits (e.g., application specific integrated circuits (ASICs) designed specifically for implementing deep learning network architectures, or field-programmable gate arrays (FPGAs) to accelerate compute time, etc., and/or to facilitate deployment), microprocessors, emerging next-generation microprocessor designs (e.g., memristor-based processors), logic devices and the like. Although the disclosure is described with reference to a processor, other types of integrated circuits and logic devices may also be applicable. The processor may have any suitable data operation capability. For example, the processor may perform 512 bit, 256 bit, 128 bit, 64 bit, 32 bit, or 16 bit data operations. The one or more processors may be single core or multi core processors, or a plurality of processors configured for parallel processing.

Applications

The disclosed methods, devices, and systems have potential application in a variety of fields including, but not limited to, proteomics research, cellular research, drug discovery and development, and clinical diagnostics. For example, the improved reproducibility and quantitation that may be achieved for separation-based ESI-MS analysis of analyte samples using the disclosed methods may be of great benefit for the characterization of biologic and biosimilar pharmaceuticals during development and/or manufacturing.

Biologics and biosimilars are a class of drugs which include, for example, recombinant proteins, antibodies, live virus vaccines, human plasma-derived proteins, cell-based medicines, naturally-sourced proteins, antibody-drug conjugates, protein-drug conjugates and other protein drugs. The FDA and other regulatory agencies require the use of a stepwise approach to demonstrating biosimilarity, which may include a comparison of the proposed product and a reference product with respect to structure, function, animal toxicity, human pharmacokinetics (PK) and pharmacodynamics (PD), clinical immunogenicity, and clinical safety and effectiveness (see "Scientific Considerations in Demonstrating Biosimilarity to a Reference Product: Guidance for Industry", U.S. Department of Health and Human Services, Food and Drug Administration, April 2015). Examples of the structural characterization data that may be required for protein products include primary structure (i.e., amino acid sequence), secondary structure (i.e., the degree of folding to form alpha helix or beta sheet structures), tertiary structure (i.e., the three dimensional shape of the protein produced by folding of the polypetide backbone and secondary structural domains), and quaternary structure (e.g., the number of subunits required to form an active protein complex, or the protein's aggregation state)). In many cases, this information may not be available without employing laborious, time-intensive, and costly techniques such as x-ray crystallography. Thus there is a need for experimental techniques that allow for convenient, real-time, and relatively high-throughput characterization of protein structure for the purposes of establishing biosimilarity between candidate biological drugs and reference drugs.

In some instances, the disclosed methods, devices, and systems may be used to provide structural comparison data for biological drug candidates (e.g., monoclonal antibodies (mAb)) and reference biological drugs for the purpose of establishing biosimilarity. For example, in some instances, isoelectric point data and/or mass spectrometry data for a drug candidate and a reference drug may provide important evidence in support of a demonstration of biosimilarity. In some embodiments, isoelectric point data and/or mass spectrometry data for a drug candidate and a reference drug that have both been treated with a site-specific protease under identical reaction conditions may provide important evidence in support of a demonstration of biosimilarity. In some embodiments, the disclosed methods, devices, and systems may be used to monitor a biologic drug manufacturing process (e.g., to monitor bioreactor processes in real time) to ensure the quality and consistency of the product by analyzing samples drawn at different points in the production process, or samples drawn from different production runs.

EXAMPLES

These examples are provided for illustrative purposes only and not to limit the scope of the claims provided herein.

Example 1—Characterize Protein Charge on Chip Before Mass Spectrometry (MS)

Figure 4A:
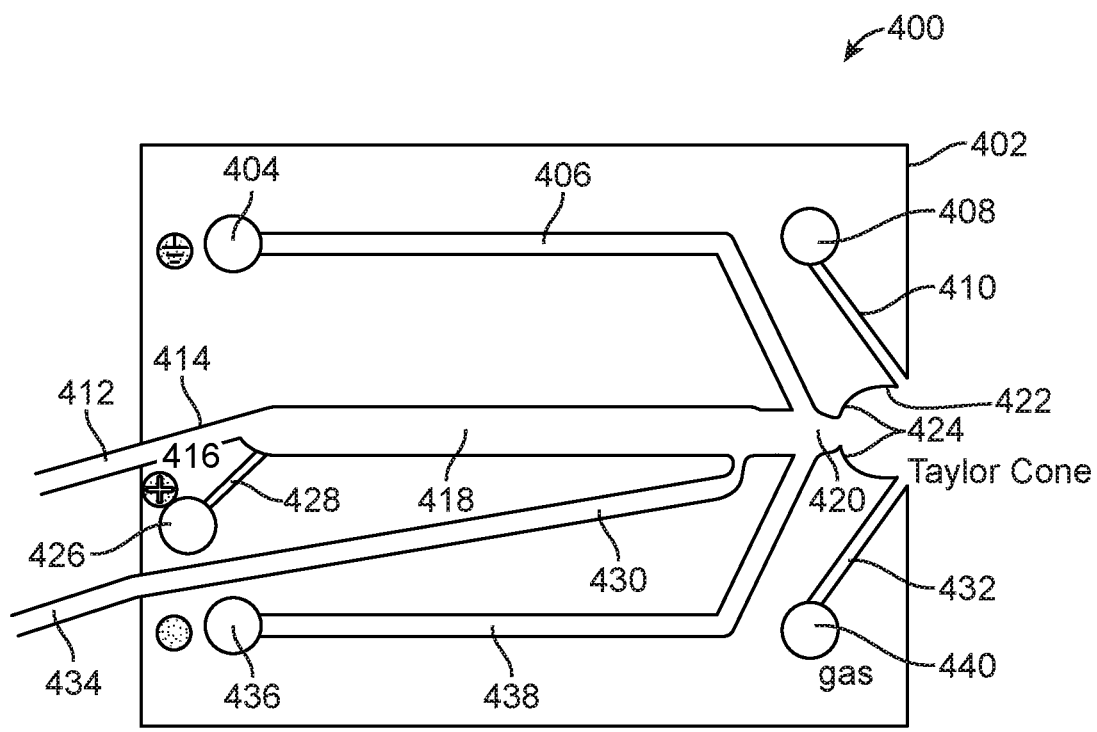
FIGS. 4A and 4B provide schematic illustrations of a microfluidic device for performing isoelectric focusing (IEF) and subsequent ESI of an automatically loaded sample, according to one aspect of this disclosure.
Figure 4B:
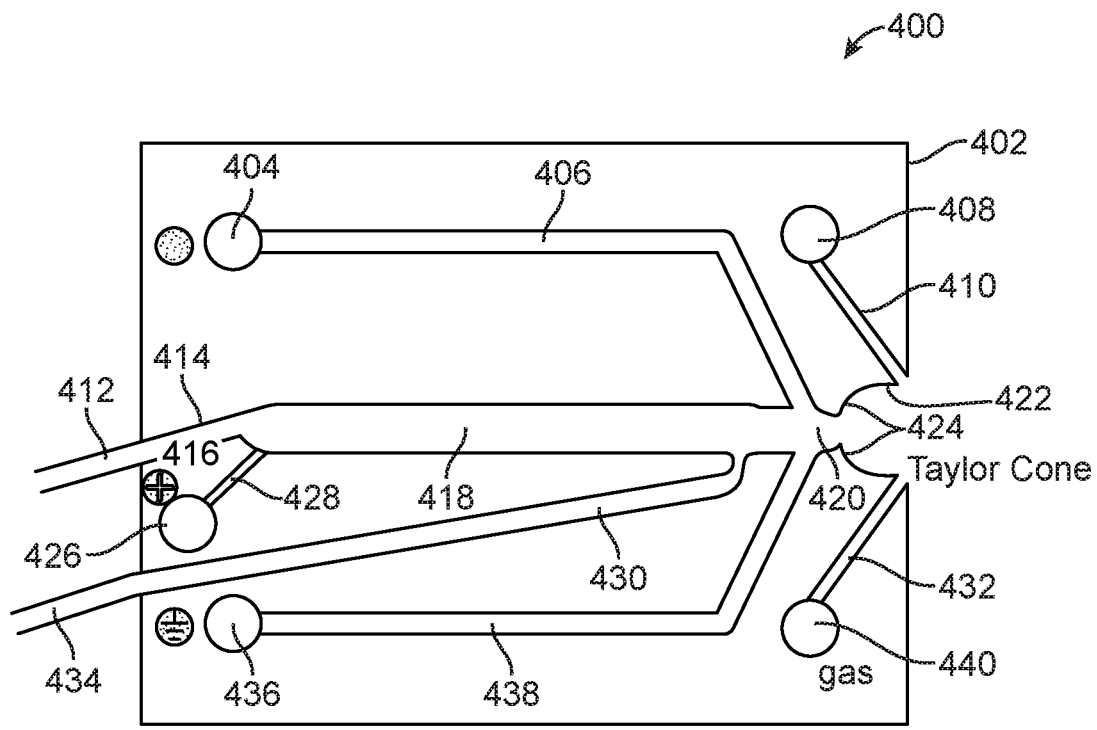

For this example, the channel network shown in FIGS. 4A and 4B is fabricated from a plate of soda lime glass, which has very low transmission of 280 nm light using a standard photolithographic etching technique. The device comprises sample inlet channel 414 connected to inlet 412, enrichment channel 418, and mobilization channel 438. Anode 416 is placed in electrical contact with anolyte well 426. The depth of the enrichment channel 418 is the same as the thickness of the glass layer 402, i.e., the enrichment channel 418 passes all the way from the top to bottom of this glass plate 402. The device 400 can be illuminated by a light source disposed on one side of device 400 and imaged by a detector on disposed on an opposite side of device 400. Because substrate 402 is opaque, but enrichment channel 418 defines an optical slit, the substrate 402 can block light that does not pass through the enrichment channel 418, blocking stray light and improving resolution of the imaging process.

The glass layer 402 is sandwiched between two fused silica plates, which are transmissive (e.g., transparent) to 280 nm light. As in FIG. 2, the top plate contains through holes for the instrument and user to interface with the channel network, while the bottom plate is solid. The 3 plates are bonded together at 520° C. for 30 minutes. The inlet and outlet tubing is manufactured from cleaved capillary (100 μm ID, polymicro), bonded to the channel network.

The device is mounted on an instrument containing a nitrogen gas source, heater, positive pressure pump (e.g., Parker, T5-1IC-03-1EEP), electrophoresis power supply (Gamm High Voltage, MC30) terminating in two platinum-iridium electrodes (e.g., Sigma-Aldrich, 357383), UV light source (e.g., LED, qphotonics, UVTOP280), CCD camera (e.g., ThorLabs, 340UV-GE) and an autosampler for loading samples onto the device. The power supply shares a common earth ground with the mass spectrometer. The instrument is controlled through software (e.g., labView).

Protein samples are pre-mixed with ampholyte pH gradient and pI markers before placing into vials and loading onto the autosampler. They are serially loaded from an autosampler via the inlet 412 onto the microfluidic device 400 through the enrichment channel 418 and out of the device to waste 430 through the outlet 434.

The sheath/catholyte fluid (50% MeOH, $N_4OH/H_2O$) is loaded onto the two catholyte wells 404, 436, anolyte (10 mM $H_3PO_4$) onto the anolyte well 426, and the source of heated nitrogen gas is attached to the two gas wells 408, 440.

After all reagents are loaded, an electric field of +600V/cm is applied from anolyte well 426 to catholyte wells 404, 436 by connecting the electrodes to the anolyte well 426 and catholyte wells 404, 436 to initiate isoelectric focusing. The UV light source is aligned under the enrichment channel 418, and the camera is placed above the enrichment channel 418 to measure the light that passes through the enrichment channel 418, thereby detecting the focusing proteins by means of their absorbance. The glass plate 402 being constructed of soda-lime glass, acts to block any stray light from the camera, so light not passing through the enrichment channel 418 is inhibited from reaching the camera, increasing sensitivity of the measurement.

Images of the focusing proteins can be captured continuously and/or periodically during IEF. When focusing is complete, low pressure will be applied from the inlet 412, mobilizing the pH gradient toward the orifice 424. The electric field can be maintained at this time to maintain the high resolution IEF separation. Continuing to image the enrichment channel 418 during the ESI process can be used to determine the pI of each protein as it is expelled from the orifice 424.

As the enriched protein fraction moves from the enrichment channel 418 into the confluence 420, it will mix with the sheath fluid, which will put the protein fraction in a mass spectrometry compatible solution, and restore charge to the focused protein (IEF drives proteins to an uncharged state), improving the ionization.

The enriched protein fraction then continues on to the orifice 424, which can be defined by a countersunk surface 422 of the glass plate 402. The enriched protein fraction can creates a Taylor cone once caught in the electric field between the sheath fluid well ground and mass spectrometer negative pole.

As solution continues to push at the Taylor cone from the enrichment channel 418, small droplets of fluid will be expelled from the Taylor cone and fly towards the mass spectrometer inlet. Nitrogen gas (e.g., at 150° C.) can flow from the gas wells 408, 440, down gas channels 410, 432 and form nitrogen gas jets which flank the Taylor cone which can convert droplets emanating from the Taylor cone to a fine mist before leaving the microfluidic device, which can aid detection in the mass spectrometer. Adjusting pressure from the inlet 412 can adapt Taylor cone size as needed to improve detection in mass spectrometer.

Example 2—Reversed-Phase->IEF->MS

Example 2 can be similar to example 1 but is described with reference to FIGS. 1A and 1B. The channel 116 can be a first enrichment zone loaded with sol-gel derivatized with C18. After loading protein, a volume of eluent (MeCN/$H_2O$ with IEF ampholytes and standards) can be loaded into channel 116 to elute the least hydrophobic proteins trapped on the sol gel. The eluate is directed to channel 124, which can be a second enrichment zone where IEF, UV absorbance monitoring and finally ESI take place as described in example 1. Once the ESI of the first eluate is complete, a volume of higher MeCN concentration is used to elute the next lowest hydrophobic protein fraction.

Example 3—Efficacy->IEF->MS

Example 3 can be similar to example 2, but biologic drug target derivatized beads can be loaded into channel 116 and used to capture protein. Affinity of reaction is characterized through elution by solution phase target (competitive), salt, pH, or the like.

Example 4—Reversed-Phase->Capillary Zone Electrophoresis->MS

Figure 5A:
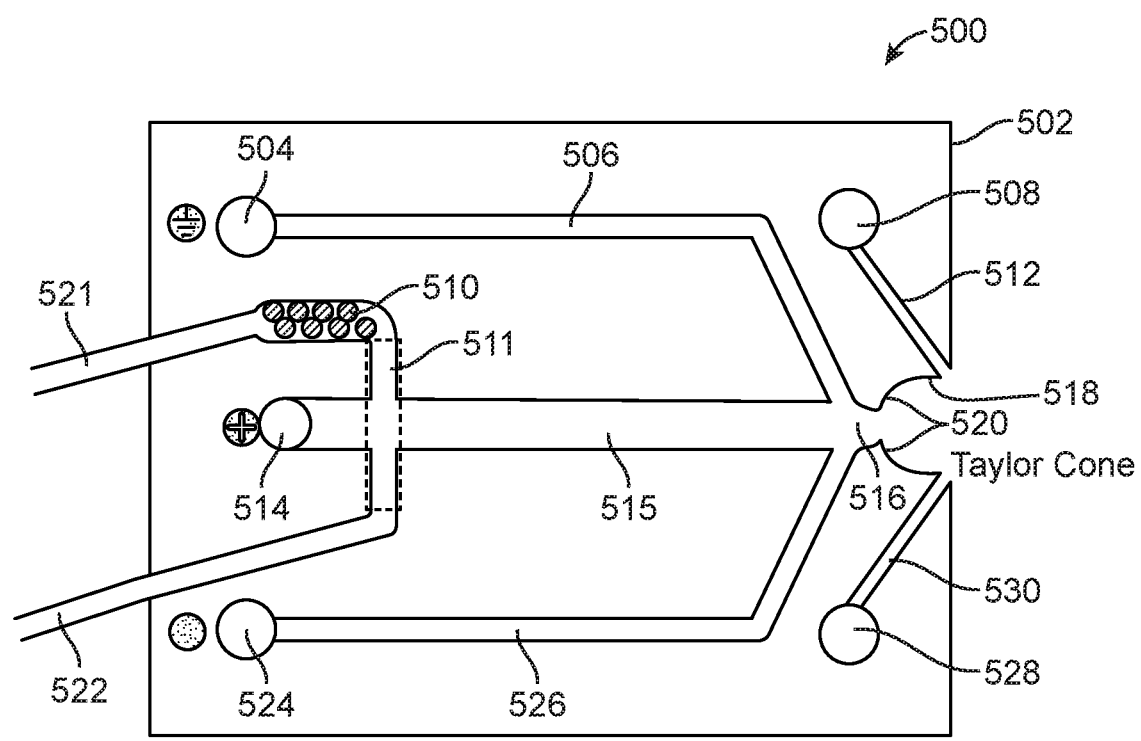
FIGS. 5A and 5B provide schematic illustrations of a microfluidic device, according to one aspect of this disclosure.
Figure 5B:
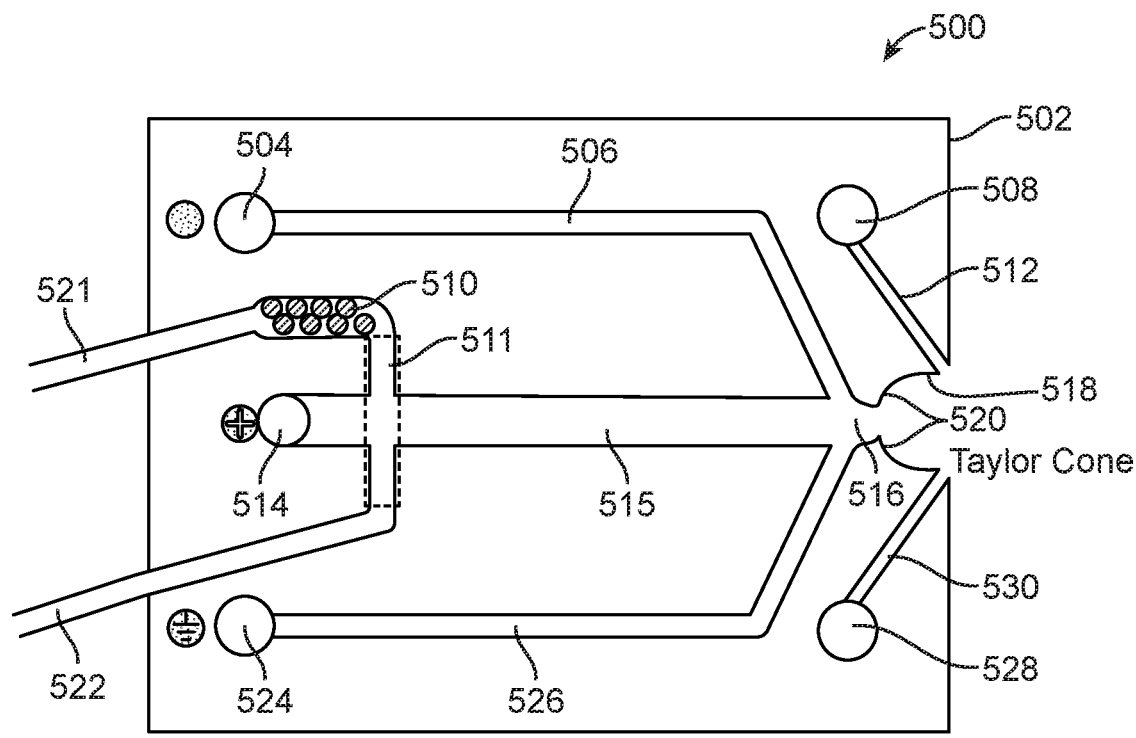

Example 4 can be similar to example 2 but is described with reference to FIGS. 5A and 5B. A protein mixture can be loaded through inlet 521 and pass through to enrichment zone 510, which can contain beads derivatized with C18 for reversed-phase chromatography. During loading, fluid passes through the zone 510, through viewing region 511 and out outlet 522 to waste. Viewing region 510 transverses an internal layer made of soda-lime glass, which is opaque to 280 nm UV light, while the top and bottom layers are made of fused silica, which are transparent to 280 nm light.

A 280 nm light source is positioned below viewing region 511 and a CCD detector is placed above viewing region 511.

A solution of 20% MeCN/H$_2$O is loaded through inlet 521 through enrichment zone 510. This solution will elute a fraction enriched for the least hydrophobic proteins in the mixture. Viewing region 511 is monitored for the absorbance of the enriched protein fraction at 280 nm as it moves from enrichment zone 510 to the outlet 522. When the fraction is positioned at the intersection of enrichment zone 510 and enrichment zone 515, a power supply is turned on creating an electric field between a positive electrode in reservoir 514 and ground at reservoir 504 (FIG. 5A) or reservoir 524 (FIG. 5B), which are connected to confluence region 516 at the end of enrichment zone 515 by means of channels 506 and 526 respectively. This polarity can easily be reversed by switching the polarity of the power supply. Once the electric field is present, the enriched protein fraction will migrate down enrichment zone 515 separating proteins by capillary zone electrophoresis. The separated proteins will mix with the sheath, electrolyte solution at confluence 516, and form a Taylor cone on surface 518. Nebulizing Nitrogen gas line is connected to the device at ports 508 and 528 and moves through channels 512 and 530 to flank material from the electrospray as it exits the device via orifice 520.

Alternatively, hydrodynamic pressure could be used to load the enriched protein fraction into enrichment zone 515.

Example 5—Immunoprecipitation->Capillary Gel Electrophoresis of Protein Lysates

In this example, a microfluidic channel layer represented by the layout in FIG. 8 is fabricated from a cyclic olefin copolymer. Similarly stated, substrate 802 of microfluidic device 800 defines a channel network. For many applications, for example, if fluorescent detection is employed, microfluidic device 800 could be manufactured using a single material, provided that this material will transmit the wavelength range of light needed to detect the analyte.

Protein A coated beads are loaded into channel 806. These beads are rinsed with a solution of antibody raised against a target of interest, which will bind to the protein A beads. To reduce antibody shedding interfering with analyte detection, the antibody is then covalently cross-linked to the antibody to the bead using commercially available cross-linking reagents, such as Dimethyl pimelimidate (DMP), Bis(sulfo-succinimidyl)suberate (BS3) and the like. After immunoprecipitation beads are prepared and loaded in channel 806, lysate analyte sample can be loaded via tube 804. After analyte is given sufficient time to be captured by immobilized antibody, unbound proteins are washed and cleared to waste via tube 822.

Next, the protein is eluted from the antibody beads so it can be analyzed. Elution is accomplished by loading solution of sodium dodecyl sulfate (SDS) and heating to 50 C for 10 minutes. Once released, the eluted analyte is flowed through channel 808 toward the intersection of channel 808 and 814. When the analyte plug reaches the intersection of channel 808 and 814, an electric field is turned on between a negative pole at reservoir 812 and a positive pole at reservoir 816, causing the negatively charged protein to migrate through a dextran linear polymer solution in channel 814, which has been loaded with the fluorogenic protein dye SYPRO® ruby.

Fluorescently labeled target protein can be visualized during CGE in channel 814 using whole column imaging. Similarly stated, the entirety of channel 814 can be imaged while the SYPRO® ruby dye is excited with 280 nm light and emitted light, at 618 nm, is measured by a detector.

Example 6—Variations of Microfluidic Design Without Mass Spectrometer Interface

In some cases, it will be advantageous to have two designs of a microfluidic layer, that differ by presence or absence of the mass spectrometer interface. Once an analyte is characterized, confirmatory characterization may be done in the absence of the mass spectrometry data. By doing the confirmatory characterization in nearly the same microfluidic design, when an anomaly is identified, it will be simple to transfer the assay back to the chip with the mass spec interface for mass identification. This can eliminate the work otherwise needed to show that the anomaly in the confirmatory data is being analyzed in the mass spectrometry data.

Figure 9:
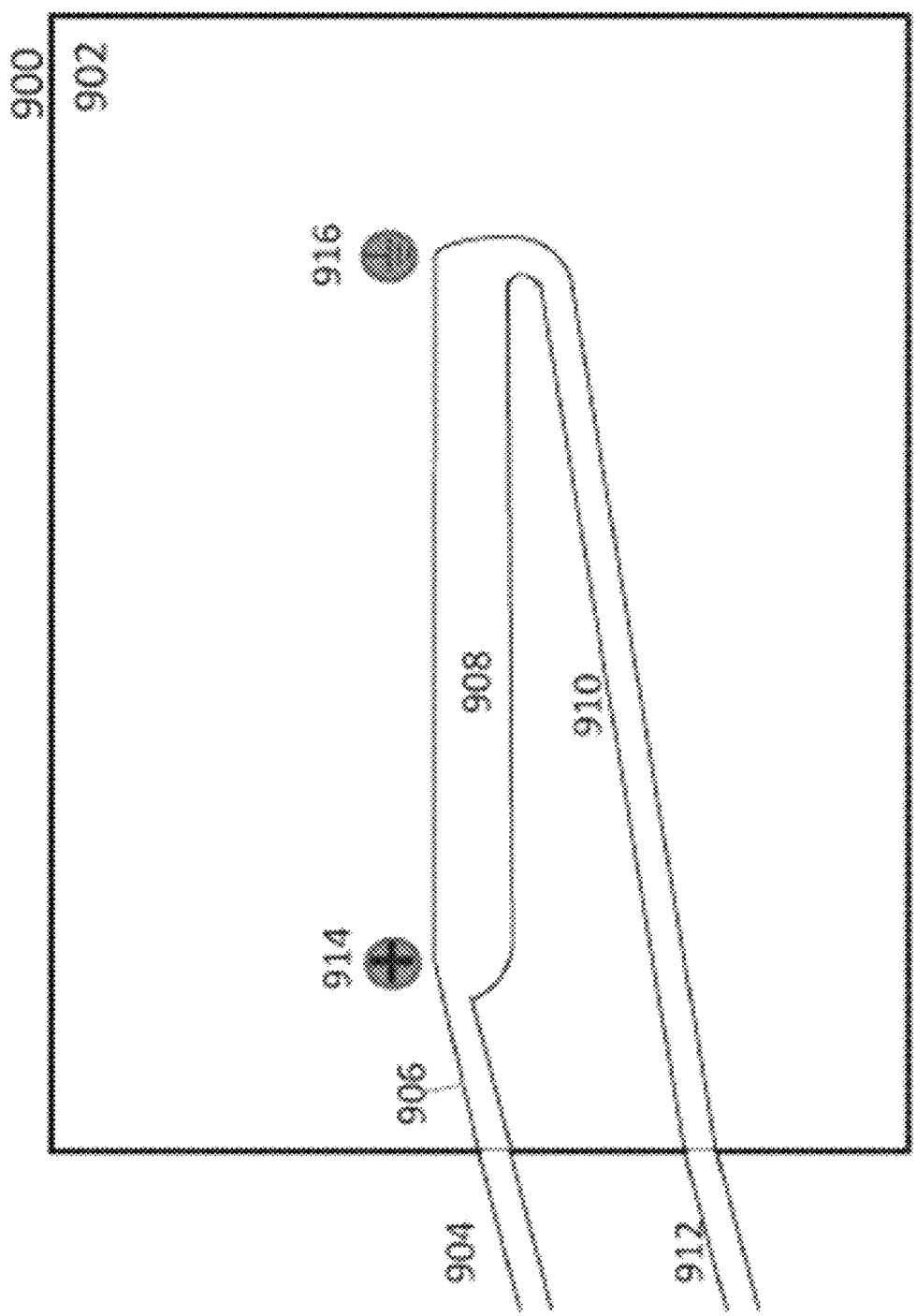
FIG. 9 provides a schematic illustration of a microfluidic device, according to one aspect of this disclosure.

As an example, FIG. 9 shows a microfluidic design similar to microfluidic device 400 shown in FIGS. 4A and 4B, without orifice 424 and countersunk surface 422. Analyte is still introduced to the chip through an inlet 904 and channel 906 to an enrichment channel 908 for analysis by application of an electrical potential difference between an anode (914) and a cathode (916), but after analysis the sample will be flushed out through an outlet channel 910, rather than conducting electrospray ionization at an orifice. This design could be run for general operation, and then at times when mass identification is required, the same enrichment can be performed on the microfluidic device 400, shown in FIGS. 4A and 4B, ensuring identification of the analyte variants see on microfluidic device 900 of FIG. 8.

Example 7—Characterize Protein Charge on Chip Before Mass Spectrometry (MS) Using Chemical Mobilization For this example, the channel network shown in FIGS. 4A and 4B is fabricated from a plate of soda lime glass, which has very low transmission of 280 nm light using a standard photolithographic etching technique. The depth of the enrichment channel 418 is the same as the thickness of the glass layer 402, i.e., the enrichment channel 418 passes all the way from the top to bottom of this glass plate 402. The device 400 can be illuminated by a light source disposed on one side of device 400 and imaged by a detector on disposed on an opposite side of device 400. Because substrate 402 is opaque, but enrichment channel 418 defines an optical slit, the substrate 402 can block light that does not pass through the enrichment channel 418, blocking stray light and improving resolution of the imaging process.

The glass layer 402 is sandwiched between two fused silica plates, which are transmissive (e.g., transparent) to 280 nm light. As in FIG. 2, the top plate contains through holes for the instrument and user to interface with the channel network, while the bottom plate is solid. The 3 plates are bonded together at 520° C. for 30 minutes. The inlet and outlet tubing is manufactured from cleaved capillary (100 μm ID, polymicro), bonded to the channel network.

The device is mounted on an instrument containing a nitrogen gas source, heater, positive pressure pump (e.g., Parker, T5-1IC-03-1EEP), electrophoresis power supply (Gamm High Voltage, MC30) terminating in two platinum-iridium electrodes (e.g., Sigma-Aldrich, 357383), UV light source (e.g., LED, qphotonics, UVTOP280), CCD camera (e.g., ThorLabs, 340UV-GE) and an autosampler for loading samples onto the device. The power supply shares a common earth ground with the mass spectrometer. The instrument is controlled through software (e.g., labView).

Protein samples are pre-mixed with ampholyte pH gradient and pI markers before placing into vials and loading onto the autosampler. They are serially loaded from an autosampler via the inlet 412 onto the microfluidic device 400 through the enrichment channel 418 and out of the device to waste 430 through the outlet 434.

The catholyte fluid (1% $N_4OH$ in $H_2O$) is loaded onto catholyte well 436, anolyte (10 mM $H_3PO_4$) onto the anolyte well 426, mobilizer solution (49% MeOH, 49% $H_2O$, 1% Acetic Acid) is added to well 404, and the source of heated nitrogen gas is attached to the two gas wells 408, 440.

After all reagents are loaded, an electric field of +600V/cm is applied from anolyte well 426 to catholyte well 436 by connecting the electrodes to the anolyte well 426 and catholyte wells 436 to initiate isoelectric focusing. The UV light source is aligned under the enrichment channel 418, and the camera is placed above the enrichment channel 418 to measure the light that passes through the enrichment channel 418, thereby detecting the focusing proteins by means of their absorbance. The glass plate 402, being constructed of soda-lime glass, acts to block any stray light from the camera, so light not passing through the enrichment channel 418 is inhibited from reaching the camera, increasing sensitivity of the measurement.

Images of the focusing proteins can be captured continuously and/or periodically during IEF. When focusing is complete, the electrode connecting catholyte well 436 is disconnected, and an electrode at mobilizer well 404 is used to apply an electric field of 600V/cm from anolyte well 426 to mobilizer well 404. Additionally, pressure will be applied to well 404 to initiate flow off approximately 100 nL/minute from 404 to the orifice at 424.

The acetic acid in the mobilizer solution is drawn by the electric field into the enrichment channel 418, where it ionizes the proteins and ampholytes, disrupting the pH gradient. The ionization of the enriched protein fractions causes them to migrate out of channel 418 into confluence 420. The enriched protein fractions then flow with the mobilizer solution through the confluence 420 and are expelled via the chip orifice 424 by electrospray ionization (ESI). Continuing to image the enrichment channel 418 during the ESI process can be used to determine the pI of each protein as it is expelled from the orifice 424.

As the enriched protein fraction moves from the enrichment channel 418 into the confluence 420, it will mix with the mobilizer solution, which will put the protein fraction in a mass spectrometry compatible solution, and maintain the ionization of the proteins.

The enriched protein fraction then continues on to the orifice 424, which can be defined by a countersunk surface 422 of the glass plate 402. The enriched protein fraction can creates a Taylor cone once caught in the electric field between the sheath fluid well ground and mass spectrometer negative pole.

As solution continues to push at the Taylor cone from the enrichment channel 418, small droplets of fluid will be expelled from the Taylor cone and fly towards the mass spectrometer inlet. Nitrogen gas (e.g., at 150° C.) can flow from the gas wells 408, 440, down gas channels 410, 432 and form nitrogen gas jets which flank the Taylor cone which can convert droplets emanating from the Taylor cone to a fine mist before leaving the microfluidic device, which can aid detection in the mass spectrometer. Adjusting pressure from the inlet 412 can adapt Taylor cone size as needed to improve detection in mass spectrometer.

Figure 10:
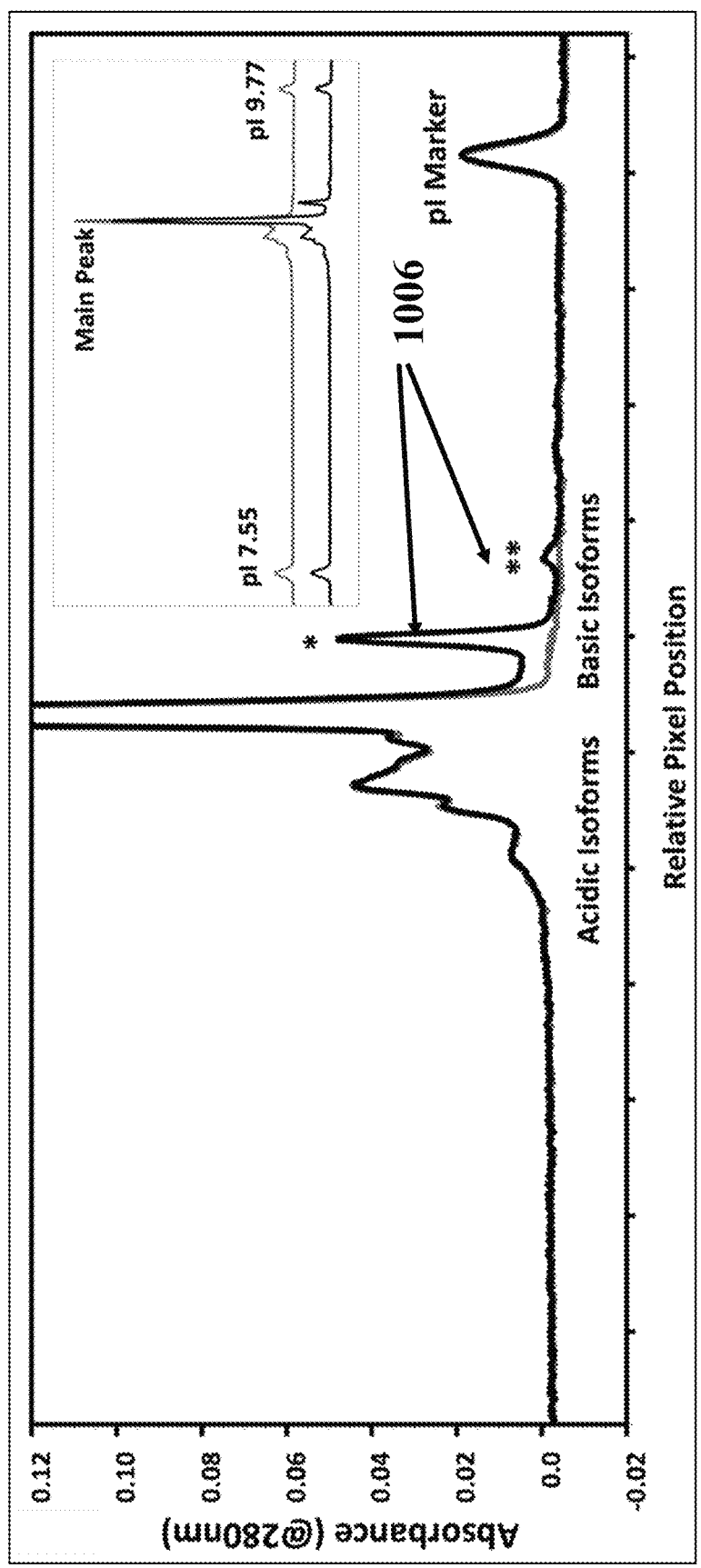
FIG. 10 shows an example of data from a separation of analytes within a sample comprising a mixture of analytes obtained using a commercial instrument.

Example 8—Comparison of IEF Separations Performed on a Commercial Instrument to Those Performed on the Disclosed Devices FIG. 10 provides an example of analyte separation data obtained using a commercial isoelectric focusing instrument (Protein Simple, San Jose, Calif.) to focus a NIST monoclonal antibody (mAb) that comprises two different C-terminal lysine variants (Genentech, *Emerging Technologies for Therapeutic Monoclonal Antibody Characterization*, Volume 2. Biopharmaceutical Characterization: The NISTmAb ACS Symposium Series; American Chemical Society: Washington, D.C., 2015). Absorbance of the protein analyte peaks was measured and plotted as a function of peak position (in image sensor pixels) along the separation axis. Monoclonal antibody isoforms were separated using IEF, and separate based on their respective pIs. Two different basic isoforms corresponding to the two C-terminal lysine variants (1006) of the monoclonal antibody can be observed in the IEF electropherogram.

FIGS. 11A-C provide examples of isoelectric focusing data for separation of the same NIST monoclonal antibody used in the data illustrated in FIG. 10. Isoelectric focusing was performed in the device illustrated in FIGS. 7A and 7B (similar to that shown in FIGS. 4A and 4B and described above, but lacking wells 408 and 440, channels 410 and 432, and recess 422; and comprising a 5 cm long separation/enrichment channel 718 having a 250 µm wide×100 µm deep cross-section; the separation channel was coated with Guarant coating (Alcor Bioseparations, Palo Alto, Calif.)). The device 700 comprises glass or polymer layer 702 that defines the thickness of the separation channel 718, mobilizer well 704 which is in fluid communication with confluence region 724 via channel 706, inlet 712 which is in fluid communication with a proximal end of separation/enrichment channel 718 via channel 714, anolyte well 726 which is in fluid communication with a proximal end of separation/enrichment channel 718 via channel 728, outlet 734 which is in fluid communication with a distal end of separation/enrichment channel 718 via fluid channel 730, catholyte well 736 which is in fluid communication with confluence region 724 via channel 738, and electrospray orifice 722 which, during operation of the device, produces a Taylor cone 720. Application of electric fields between an anode (716), cathode (indicated as ground in FIG. 7A), and mobilization electrode (indicated as ground in FIG. 7B) to perform isoelectric focusing and electrophoretic introduction of a mobilization agent were as described for the corresponding features in the device illustrated in FIGS. 4A and 4B, as described above.

A sample of 250 µg/mL of NIST mAb in 1.5% Pharmalyte 3-10, 1.5% Pharmalyte 8-10.5 (in water) was loaded into the separation channel (1% formic acid used as anolyte; 1% diethylamine used as catholyte (all in water)), and a separation electric field of 300 V/cm was applied for 1 minute (to minimize Joule heating), followed by application of an electric field of 600 V/cm for 6 minutes (following the initial focusing of the sample, the conductivity of the separation channel drops and the electric field may be increased to accelerate the IEF separation). UV absorbance traces were acquired through whole channel imaging of the separation channel. The two C-terminal lysine variants of the NIST mAb are clearly resolved. The reproducibility of the IEF separation as performed using the disclosed microfluidic devices and methods is indicated by comparison of the traces acquired using three different chips (2811 (FIG. 11A), 2808 (FIG. 11B), and 2805 (FIG. 11C)).

Example 9—Linearity of pH Gradients

Figure 7A:
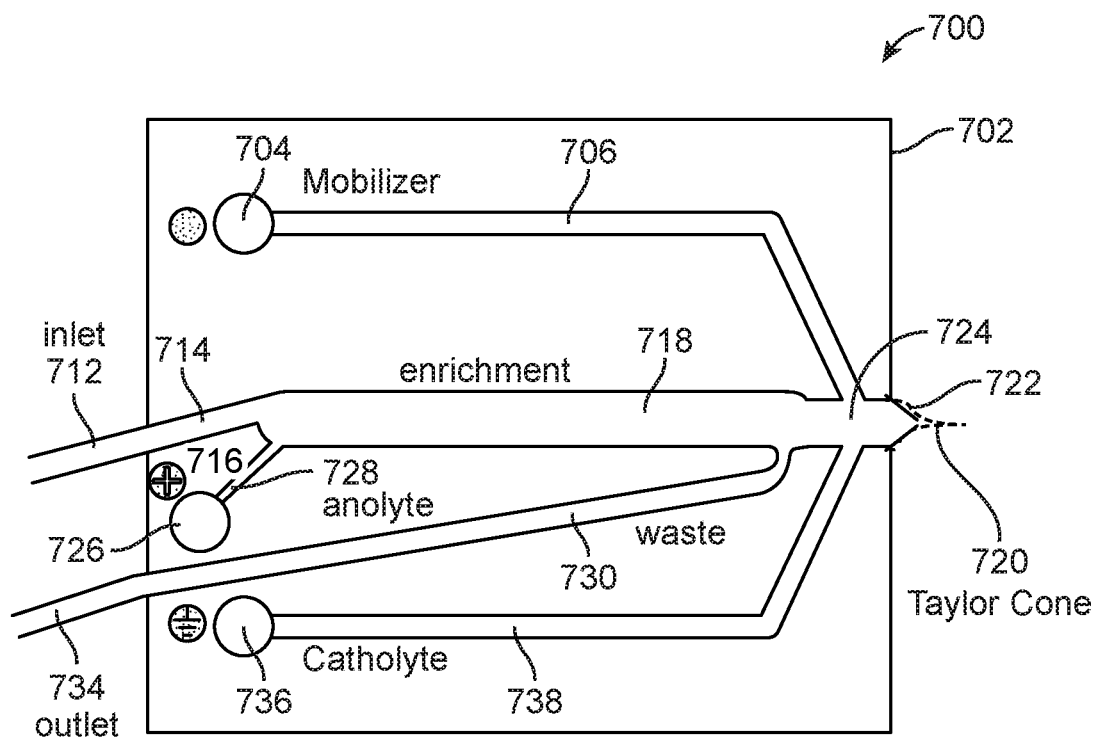
FIGS. 7A and 7B provide schematic illustrations of a microfluidic device, according to one aspect of this disclosure.
Figure 7B:
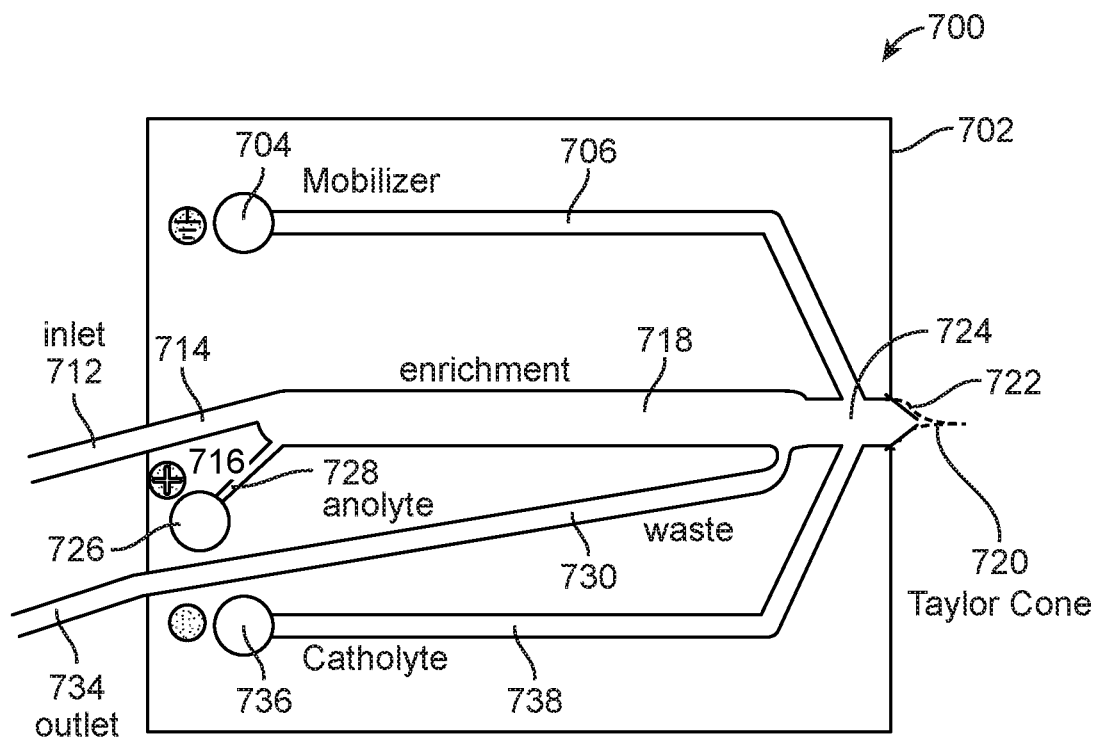
Figure 12:
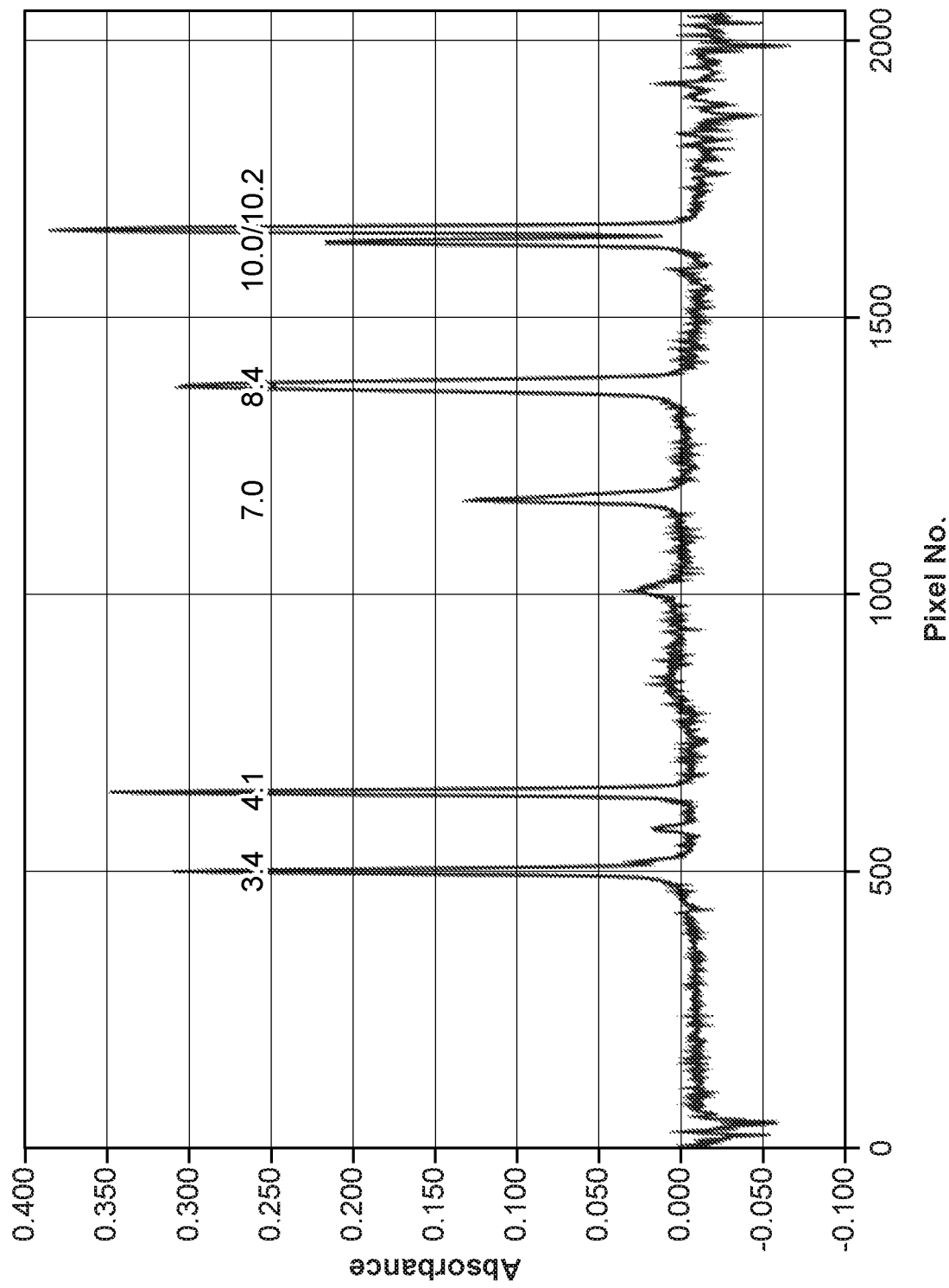
FIG. 12 provides a non-limiting example of isoelectric focusing data for a set of pI markers.

FIG. 12 provides an example of isoelectric focusing data for a separation reaction performed in the microfluidic device illustrated in FIGS. 7A and 7B and described above. A sample comprising pI markers for pH 3.38, 4.05, 7.00, 8.40, 9.99, and 10.17 in 3% Pharmalyte 3-10 (in water) was loaded into the separation channel (1% formic acid used as anolyte; 1% diethylamine used as catholyte (all in water)), and a separation electric field of 300 V/cm was applied for 1 minute, followed by application of an electric field of 600 V/cm for 6 minutes. The UV absorbance trace illustrated in FIG. 12 was acquired through whole channel imaging of the separation channel. The pI markers, including the pH 10.0 and 10.2 markers, are well resolved.

Figure 13:
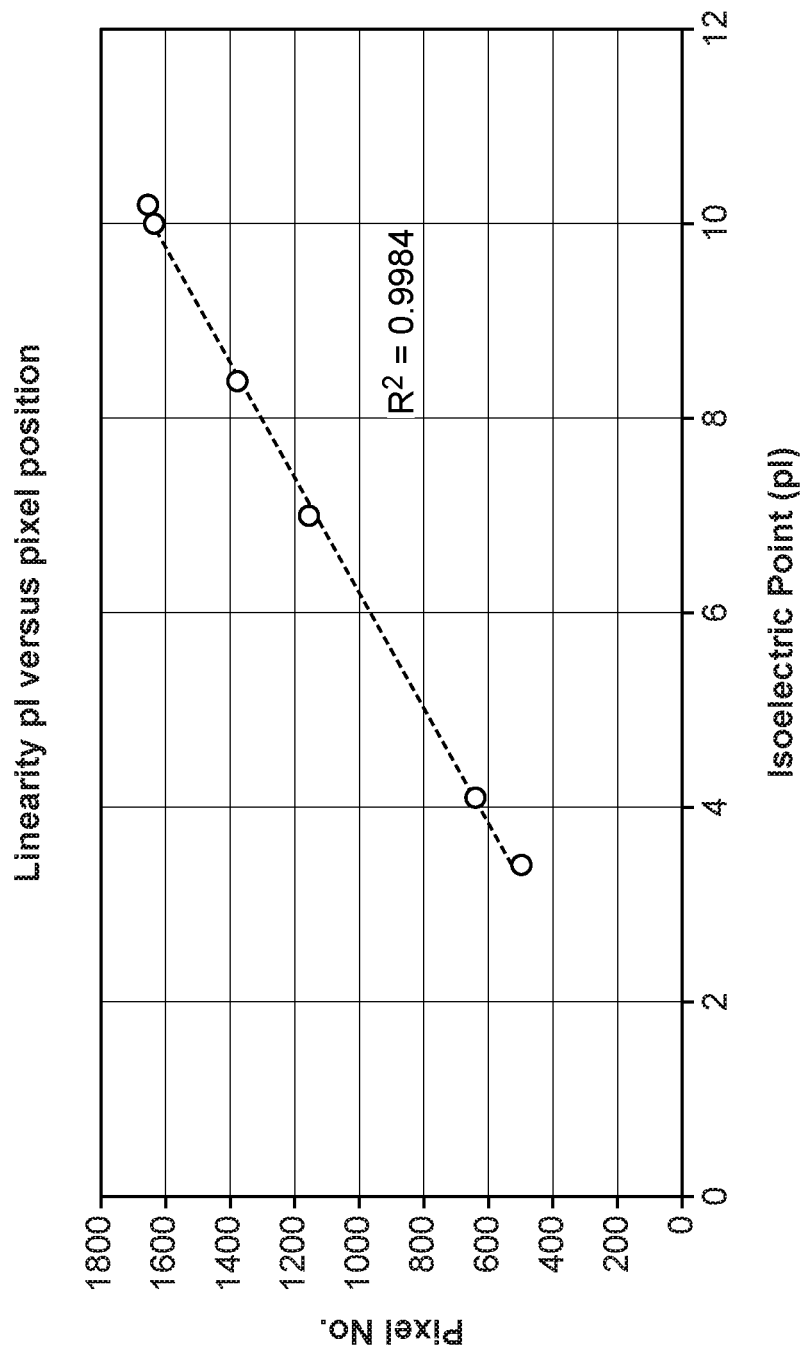
FIG. 13 provides a non-limiting example of a linearity plot (pixel position on the sensor used to image the separation channel versus gradient pH) for the data illustrated in FIG. 12.

FIG. 13 provides a plot of peak position (in terms of image sensor pixels) versus pH for the date shown in FIG. 12. The dashed line indicates the best fit of the experimental data to a straight line, and indicates the extremely high accuracy of the pH gradient that may be achieved using the disclosed devices and methods.

Figure 14:
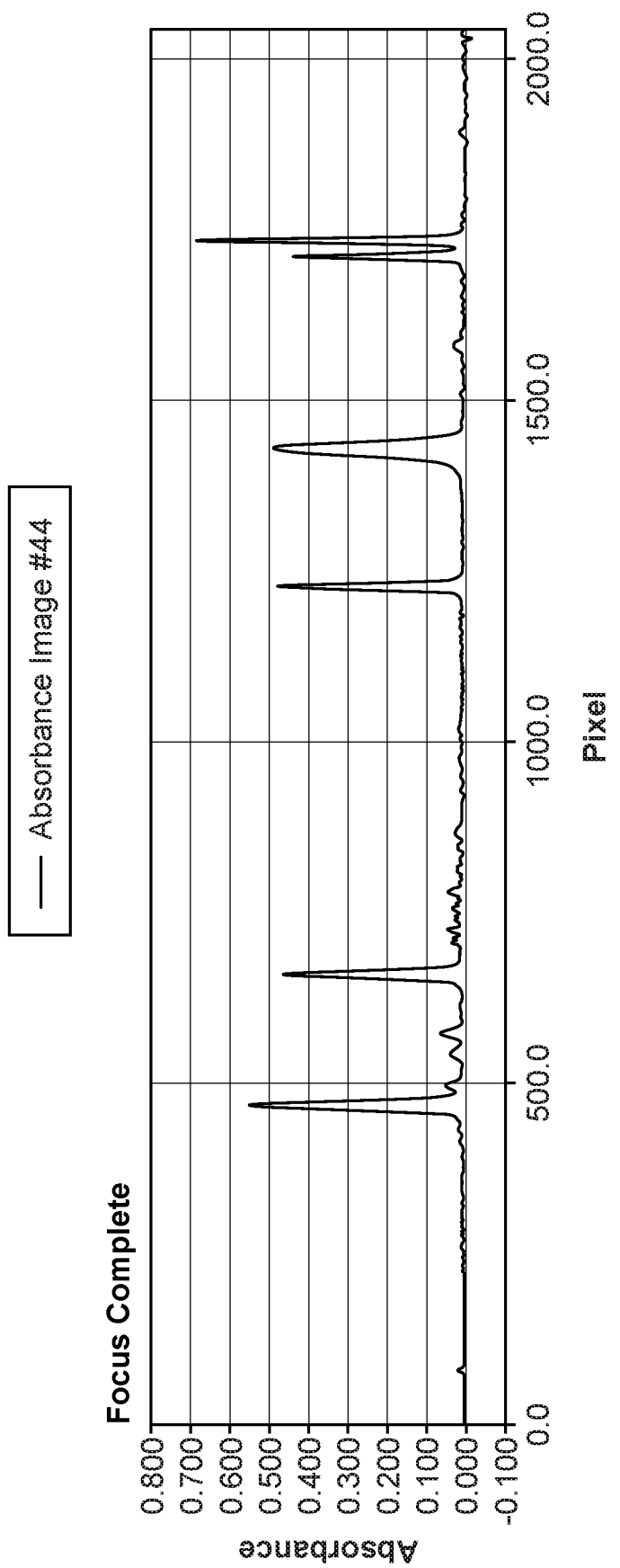
FIG. 14 provides a non-limiting example of isoelectric focusing data after the focusing step is complete.
Figure 15A:
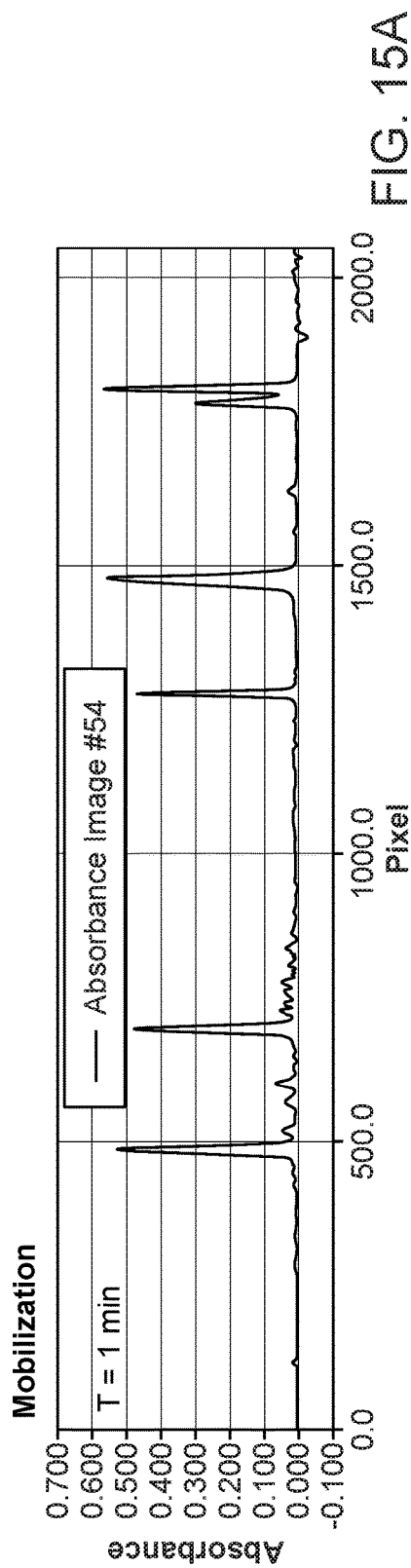
FIGS. 15A-F show non-limiting examples of data for mobilization of a sample following separation of analytes in a mixture of analytes using isoelectric focusing.
Figure 15B:
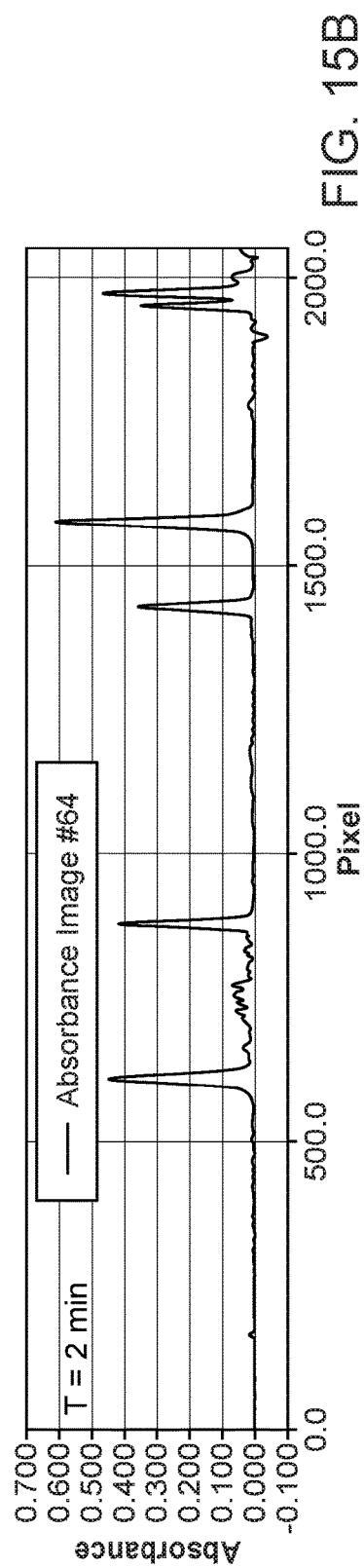
Figure 15C:
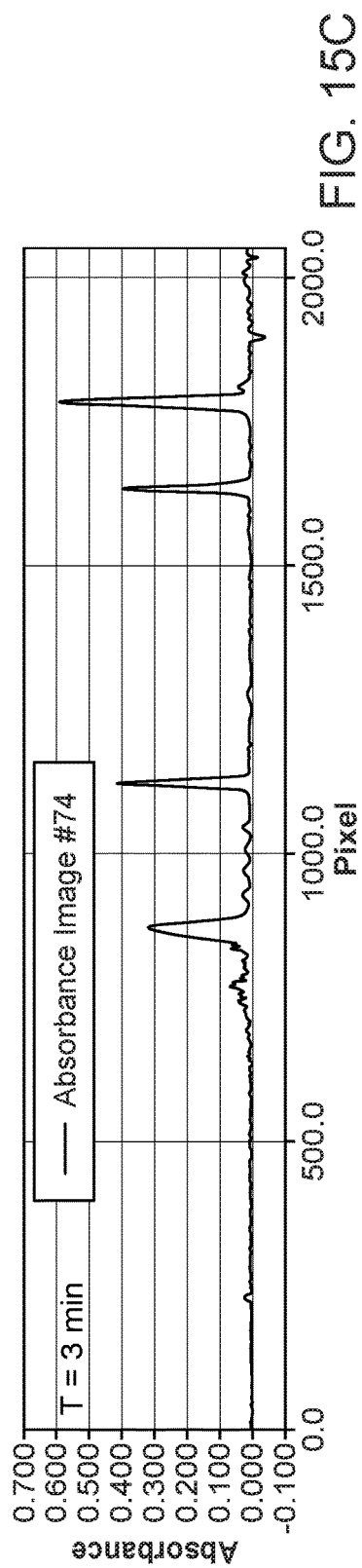
Figure 15D:
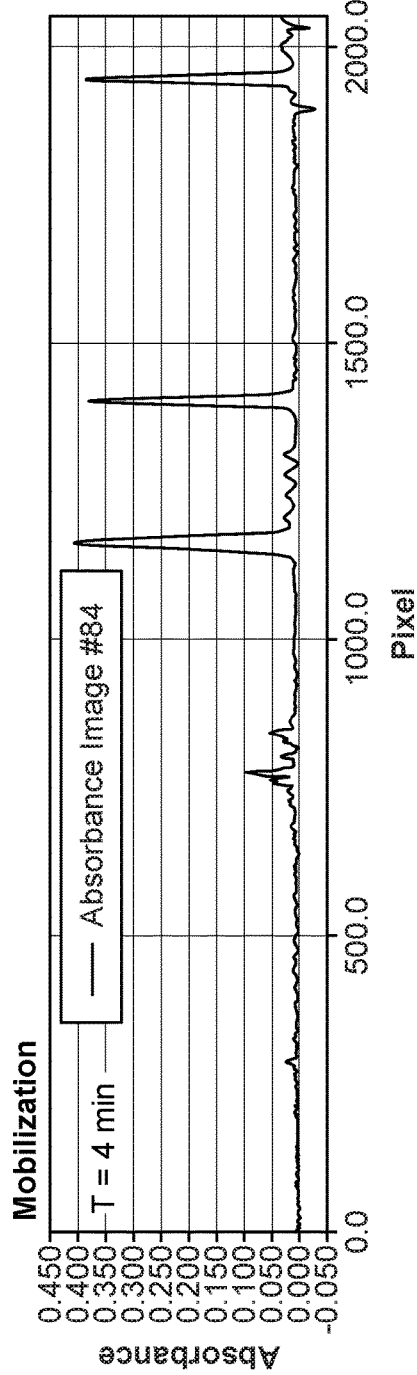
Figure 15E:
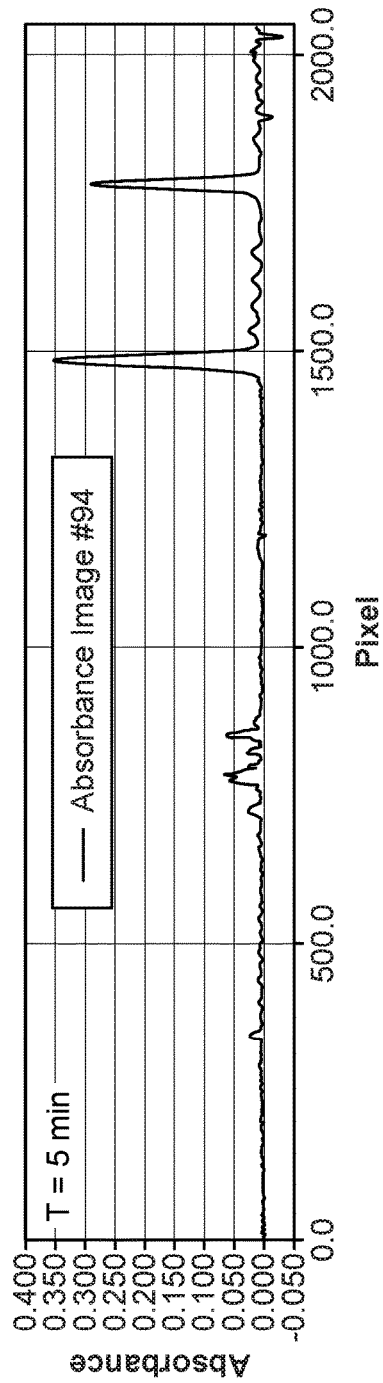
Figure 15F:
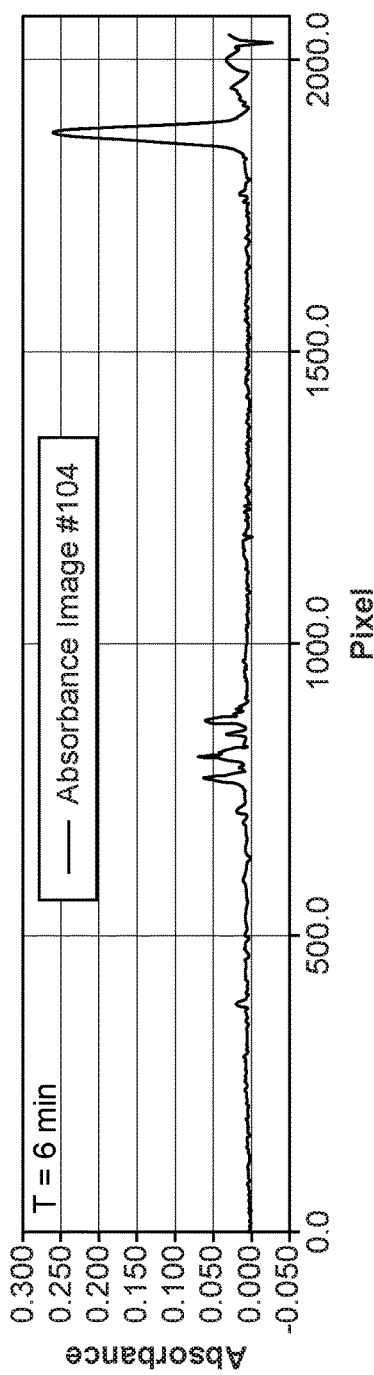

Example 10—Electrophoretic Introduction of a Mobilizing Agent and Improvement in Separation Resolution FIG. 14 shows an example of data for isoelectric focusing of a series of pI standards in a microfluidic device such as the one illustrated in FIGS. 7A and 7B and described above. A sample comprising pI markers for pH 3.38, 4.05, 7.00, 8.40, 9.99, and 10.17 (250 µg/mL each) in 3% Pharmalyte 3-10 (in water) was loaded into the separation channel (1% formic acid used as anolyte; 1% diethylamine used as catholyte; 1% formic acid, 50% isopropyl alcohol used a mobilizer (all in water)), and a separation electric field of 300 V/cm was applied for 1 minute, followed by application of an electric field of 600 V/cm for 6 minutes. The UV absorbance trace illustrated in FIG. 14 was acquired through whole channel imaging of the separation channel.

Following completion of the isoelectric focusing separation, the cathode used to provide the separation electric field was switched off and a cathode in electrical communication with the mobilization channel was turned on to initiate mobilization through electrophoretic introduction of the mobilizer to the separation channel. An electric field (400 V/cm) was applied between the cathode and anode to drive electrophoresis of the mobilizing agent for 5 minutes. FIGS. 15A-F show examples of the UV absorbance traces acquired at 1 minute (FIG. 15A), 2 minutes (FIG. 15B), 3 minutes (FIG. 15C), 4 minutes (FIG. 15D), 5 minutes (FIG. 15E), and 6 minutes (FIG. 15F) after the mobilization field was turned on. As can be seen, there is little or no band-broadening observed in this series of traces, indicating that the on-chip switching of electrodes and use of electrophoretic introduction of the mobilizing agent preserves the separation resolution achieved through IEF even as they are transferred out of the separation channel.

Figure 16A:
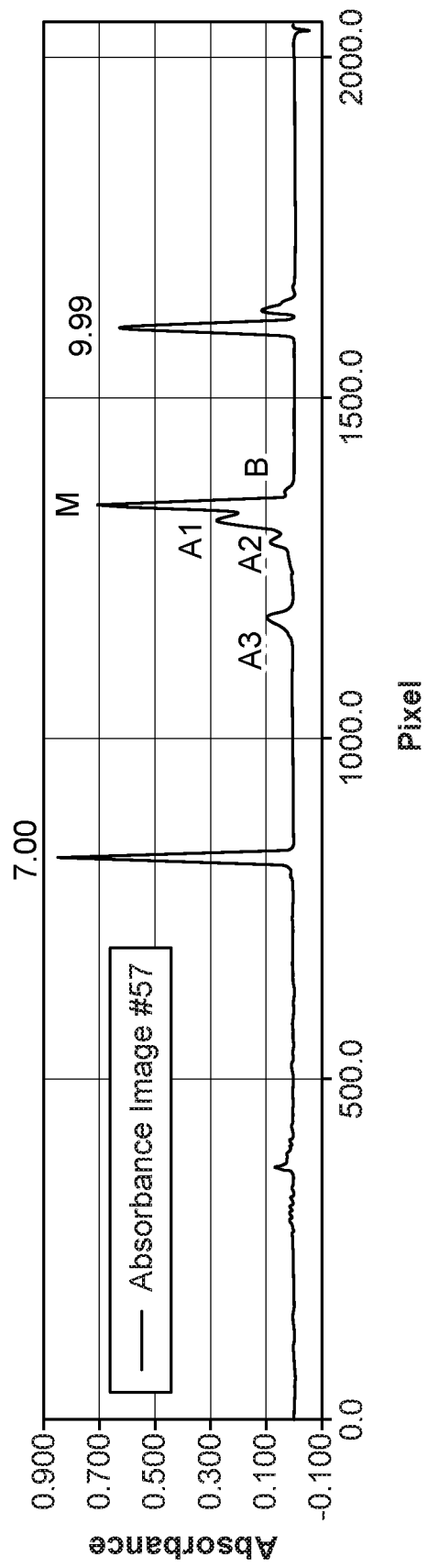
FIGS. 16A-B show non-limiting examples of data for mobilization of a sample following separation of analytes in a mixture of using isoelectric focusing and electrophoretic introduction of the mobilization electrolyte.

FIG. 16A shows an example of data for isoelectric focusing of a sample comprising two pI standards (7.00 and 9.99) and a monoclonal antibody in a microfluidic device such as the one illustrated in FIGS. 7A and 7B and described above. A sample comprising the pH 7.00 and 9.99 pI markers (250 µg/mL each) and 250 µg/mL of Trastuzumab in 1.5% Pharmalyte 3-10, 1.5% Pharmalyte 8-10.5 (in water) was loaded into the separation channel (1% formic acid used as anolyte; 1% diethylamine used as catholyte; 1% formic acid, 50% isopropyl alcohol used a mobilizer (all in water)), and a separation electric field of 300 V/cm was applied for 1 minute, followed by application of an electric field of 600 V/cm for 6 minutes. The UV absorbance trace illustrated in FIG. 16A was acquired through whole channel imaging of the separation channel.

Figure 16B:
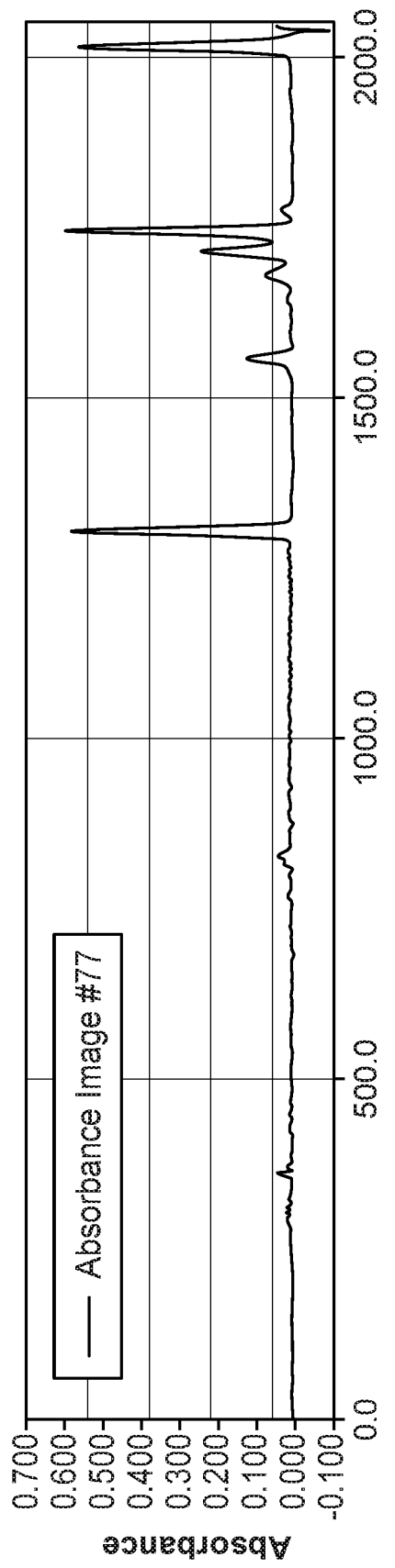

Following completion of the isoelectric focusing separation, the cathode used to provide the separation electric field was switched off and a cathode in electrical communication with the mobilization channel was turned on to initiate mobilization through electrophoretic introduction of the mobilizer to the separation channel. An electric field (400 V/cm) was applied between the cathode and anode to drive electrophoresis of the mobilizing agent for 5 minutes. FIG. 16B shows an example of the UV absorbance traces acquired 5 minutes after initiation of the electrophoretic mobilization step.

The separation resolution for different peak pairs were calculated from the UV absorbance traces shown in FIGS. 16A-B, where the estimated separation resolution was calculated as the difference in migration time for two peaks (in units of pixels) divided by the full baseline peak width (in pixels). This calculation should yield a value of 0.5 for Gaussian peaks that are barely baselined resolved. The resolution data calculated from the UV traces shown in FIGS. 16A-B are summarized in Table 1, and indicate that the use of the disclosed electrophoretic mobilization methods results in measureable improvement in peak resolution as mobilization is being performed.

TABLE 1

Estimates of separation resolution.

| Peak Pair | FIG. 16A (end of focusing) | FIG. 16B (mobilizing) |
|---|---|---|
| A2/A3 | 1.03 | 1.66 |
| A1/A2 | 0.22 | 0.44 |
| M/A1 | 0.33 | 0.40 |
| B/M | 0.36 | 0.47 |

While preferred embodiments of the disclosed methods, devices, and systems have been shown and described herein, it will be obvious to those of skill in the art that such embodiments are provided by way of example only. Numerous variations, changes, and substitutions will now occur to those skilled in the art without departing from the invention. It should be understood that various alternatives to the embodiments of the methods, devices, and systems described herein may be employed in any combination in practicing the invention. It is intended that the following claims define the scope of the invention and that methods and structures within the scope of these claims and their equivalents be covered thereby.

What is claimed is:

1. A method for electrophoretic introduction of a mobilization electrolyte into a separation channel comprising one or more isoelectrically focused analyte bands, the method comprising:
  a) performing isoelectric focusing of a sample comprising one or more analytes within the separation channel by applying a first electric field between a first electrode and a second electrode, thereby separating the sample into one or more isoelectrically focused analyte bands, wherein the first electrode is in electrical contact with a proximal end of the separation channel, and wherein the second electrode is in electrical contact with a distal end of the separation channel; and b) electrophoretically introducing a mobilization electrolyte from a mobilization channel into the separation channel to initiate mobilization of the one or more isoelectrically focused analyte bands, wherein the mobilization channel is distinct from the separation channel and a distal end of the mobilization channel intersects the separation channel at a single point at the distal end of the separation channel, by automatically switching off the first electric field and automatically switching on a second electric field applied between the first electrode and a third electrode that is in electrical contact with a proximal end of the mobilization channel.

2. The method of claim 1, wherein the separation channel is a microchannel in a microfluidic device.

3. The method of claim 1, wherein the separation channel is a capillary.

4. The method of claim 1, wherein the electrophoretic introduction of the mobilization electrolyte leads to improved separation resolution after mobilization compared to that attained at the completion of the isoelectric focusing and prior to the electrophoretic introduction of the mobilization electrolyte.

5. The method of claim 4, wherein the improvement in separation resolution is at least 20%.

6. The method of claim 4, wherein the improvement in separation resolution is at least 40%.

7. The method of claim 4, wherein the improvement in separation resolution is at least 60%.

8. The method of claim 4, wherein the improvement in separation resolution is at least 80%.

9. The method of claim 1, wherein the mobilization electrolyte comprises acetic acid, formic acid, carbonic acid, or any combination thereof.

10. The method of claim 1, wherein the mobilization electrolyte comprises ammonium hydroxide, diethylamine, dimethyl amine, piperidine, or any combination thereof.

11. The method of claim 1, wherein the automatic switching of the first electric field and the second electric field occurs at a user-specified time following initiation of the isoelectric focusing by applying the first electric field.

12. The method of claim 1, wherein the automatic switching of the first electric field and the second electric field is triggered by monitoring a current flowing through the separation channel during the isoelectric focusing and detecting when the current drops below a specified current threshold.

13. The method of claim 1, wherein the one or more isoelectrically focused analyte bands are mobilized towards an electrospray ionization interface with a mass spectrometer.

14. The method of claim 13, wherein a nebulizing gas is used to facilitate electrospray ionization.

15. The method of claim 1, further comprising acquiring images of all or a portion of the separation channel during both the isoelectric focusing in (a) and the mobilization in (b).

16. The method of claim 15, wherein data derived from the images enables more accurate isoelectric point (pI) determinations for the one or more isoelectrically focused analyte bands.

17. The method of claim 15, wherein data derived from the images is used to correlate isoelectric point (pI) data for the one or more isoelectrically focused analyte bands with mass spectrometer data.

18. The method of claim 15, further comprising processing the images, wherein data derived from the processed images is used to trigger the automatic switching of the first electric field and the second electric field.

19. The method of claim 15, wherein the images are processed to monitor the presence or absence of an isoelectrically focused analyte band of the one of more isoelectrically focused analyte bands in the separation channel.

20. The method of claim 19, wherein the first electric field is maintained in an "on" state if no isoelectrically focused analyte band is detected in the separation channel.

21. The method of claim 19, wherein the images are processed to monitor changes in position of the one or more isoelectrically focused analyte bands over time or changes in the width of the one or more isoelectrically focused analyte bands over time.

22. The method of claim 21, wherein an absence of change or a reduction in a rate of change in isoelectrically focused analyte band position or band width for the one or more isoelectrically focused analyte bands over a time period of at least 20 seconds triggers the automatic switching of the first electric field and the second electric field.

23. The method of claim 15, wherein the images are acquired using light transmitted through the separation channel.

24. The method of claim 15, wherein the images are UV absorbance images or fluorescence images.

25. The method of claim 24, wherein the fluorescence images are native fluorescence images.

26. The method of claim 15, wherein the images are acquired at a rate of at least 1 image every 15 seconds.

27. The method of claim 1, wherein the one or more analytes are proteins.

28. The method of claim 27, wherein the proteins are intact proteins.

29. The method of claim 1, wherein the method is implemented by a system used to generate data to establish biosimilarity between a candidate biological drug and a reference biological drug.

* * * * *